(12) United States Patent
Callahan et al.

(10) Patent No.: US 7,479,558 B2
(45) Date of Patent: Jan. 20, 2009

(54) PROCESS FOR PREPARING PYRIDO[2,3-D]PYRIMIDIN-7-ONE AND 3,4-DIHYDROPYRIMIDO[4,5-D]PYRIMIDIN-2(1H)-ONE DERIVATIVES

(75) Inventors: James F. Callahan, King of Prussia, PA (US); Jeffrey C. Boehm, King of Prussia, PA (US); Zehong Wan, King of Prussia, PA (US); Hongxing Yan, King of Prussia, PA (US); Xichen Lin, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 66 days.

(21) Appl. No.: 11/388,375

(22) Filed: Mar. 24, 2006

(65) Prior Publication Data

US 2006/0258687 A1 Nov. 16, 2006

Related U.S. Application Data

(60) Provisional application No. 60/665,154, filed on Mar. 25, 2005.

(51) Int. Cl.
| | | |
|---|---|---|
| C07D 487/04 | (2006.01) | |
| C07D 239/30 | (2006.01) | |
| C07D 413/04 | (2006.01) | |
| C07D 471/04 | (2006.01) | |

(52) U.S. Cl. .................. 544/118; 544/256; 544/117; 544/279; 544/318

(58) Field of Classification Search .......... 544/118, 544/256

See application file for complete search history.

(56) References Cited

U.S. PATENT DOCUMENTS

| | | | |
|---|---|---|---|
| 3,843,663 | A | 10/1974 | Williams et al. |
| 4,560,691 | A | 12/1985 | Lesher et al. |
| 4,886,807 | A | 12/1989 | Kitamura et al. |
| 4,897,395 | A | 1/1990 | Duch et al. |
| 5,304,560 | A | 4/1994 | Shimazaki et al. |
| 5,409,930 | A | 4/1995 | Spada et al. |
| 5,426,110 | A | 6/1995 | Gossett et al. |

(Continued)

FOREIGN PATENT DOCUMENTS

EP 0 278 686 2/1988

(Continued)

OTHER PUBLICATIONS

Martinez-Teipel, et al., J. Combinatorial Chem., 2005, 7(3), 436-448.*

(Continued)

*Primary Examiner*—Mark L. Berch
*Assistant Examiner*—Cecilia M Jaisle
(74) *Attorney, Agent, or Firm*—Dara L. Dinner; Stephen Venetiner; Charles M. Kinzig

(57) ABSTRACT

The present invention is directed to a novel method of preparing of 2,4,8-trisubstituted pyrido[2,3-d]pyrimidin-7-one pharmacophores of Formula (II) or (IIa)

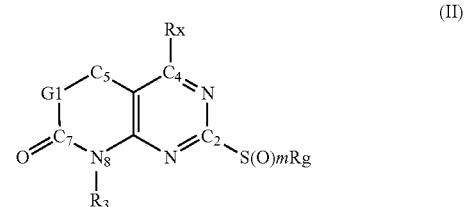

(II)

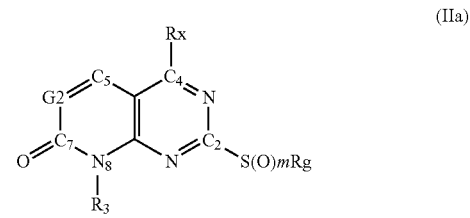

(IIa)

wherein
G1 is $CH_2$ or NH:
G2 is CH or nitrogen;
Rx is chloro, bromo, iodo, or $O-S(O)_2CF_3$;
$R_g$ is a $C_{1-10}$alkyl;
m is 0, or an integer having a value of 1, or 2;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted.

which comprises reacting a compound of the formula:

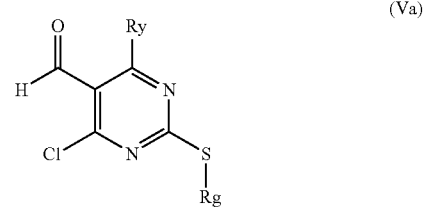

(Va)

wherein
Ry is chloro, bromo, iodo, $O-S(O)_2CF_3$; and
Rg is a $C_{1-10}$ alkyl;
with a olefin forming reagent in a suitable base to yield a compound of Formula (II), or (IIa) wherein m=0 and oxidizing the sulphur as necessary or desired.

69 Claims, No Drawings

U.S. PATENT DOCUMENTS

| | | | |
|---|---|---|---|
| 5,466,692 | A | 11/1995 | Ellingboe |
| 5,547,954 | A | 8/1996 | Henrie, II et al. |
| 5,597,776 | A | 1/1997 | Bratz et al. |
| 5,620,981 | A | 4/1997 | Blankley et al. |
| 5,733,913 | A | 3/1998 | Blankley et al. |
| 5,733,914 | A | 3/1998 | Blankley et al. |
| 5,760,220 | A | 6/1998 | Giguere et al. |
| 5,767,097 | A | 6/1998 | Tam |
| 5,817,670 | A | 10/1998 | Takayama et al. |
| 5,945,422 | A | 8/1999 | Doherty et al. |
| 6,083,948 | A | 7/2000 | Wilde |
| 6,200,977 | B1 | 3/2001 | Cusing et al. |
| 6,277,989 | B1 | 8/2001 | Chakravarty et al. |
| 6,476,031 | B1 | 11/2002 | Chakravarty et al. |
| 6,479,463 | B1 | 11/2002 | Wang et al. |
| 6,492,520 | B1 | 12/2002 | Chen |
| 6,498,163 | B1 | 12/2002 | Boschelli et al. |
| 6,528,508 | B2 | 3/2003 | Salituro et al. |
| 6,528,513 | B2 | 3/2003 | Cusing et al. |
| 6,593,333 | B1 | 7/2003 | Cumming |
| 6,800,626 | B2 | 10/2004 | Salituro et al. |
| 6,809,199 | B2 | 10/2004 | Doherty et al. |
| 6,838,559 | B2 | 1/2005 | Vaccaro et al. |
| 6,875,769 | B2 | 4/2005 | Chen |
| 7,235,551 | B2 | 6/2007 | Adams et al. |
| 2003/0114671 | A1 | 6/2003 | Chen |
| 2004/0009993 | A1 | 1/2004 | Angiolini |
| 2004/0063658 | A1 | 4/2004 | Roberts et al. |
| 2004/0087600 | A1* | 5/2004 | Cai et al. .................. 514/262.1 |
| 2004/0116697 | A1 | 6/2004 | Adams et al. |
| 2004/0142945 | A1 | 7/2004 | Barbosa et al. |
| 2004/0209901 | A1 | 10/2004 | Adams et al. |
| 2004/0224958 | A1 | 11/2004 | Booth et al. |
| 2004/0235847 | A1 | 11/2004 | Quan et al. |
| 2004/0236084 | A1 | 11/2004 | Biwersi et al. |
| 2004/0242604 | A1 | 12/2004 | Bhattacharya et al. |
| 2005/0187217 | A1 | 8/2005 | Wilson et al. |
| 2005/0203109 | A1 | 9/2005 | Adams et al. |
| 2005/0272728 | A1 | 12/2005 | Altenbach et al. |
| 2006/0217401 | A1 | 9/2006 | Boehm et al. |
| 2006/0235029 | A1 | 10/2006 | Boehm et al. |
| 2006/0235030 | A1 | 10/2006 | Callahan et al. |

FOREIGN PATENT DOCUMENTS

| | | |
|---|---|---|
| EP | 0 530 994 | 3/1993 |
| GB | 2 123 830 | 2/1984 |
| JP | 1-261306 | 10/1989 |
| JP | 20000038350 | 8/2000 |
| JP | 2003/127542 | 5/2003 |
| JP | 2004-203751 | 7/2004 |
| WO | WO 92/12154 | 7/1992 |
| WO | WO 94/19350 | 9/1994 |
| WO | WO 95/15952 | 6/1995 |
| WO | WO 95/19774 | 7/1995 |
| WO | WO 95/33750 | 12/1995 |
| WO | WO 97/38992 | 10/1997 |
| WO | WO 98/05661 | 2/1998 |
| WO | WO 98/08846 | 3/1998 |
| WO | WO 98/27098 | 6/1998 |
| WO | WO 98/33798 | 8/1998 |
| WO | WO 99/41253 | 8/1999 |
| WO | WO 99/61444 | 12/1999 |
| WO | WO 99/64400 | 12/1999 |
| WO | WO 00/23444 | 4/2000 |
| WO | WO 00/43374 | 7/2000 |
| WO | WO 01/19828 | 3/2001 |
| WO | WO 01/42243 | 6/2001 |
| WO | WO 01/55147 | 8/2001 |
| WO | WO 01/70741 | 9/2001 |
| WO | WO 02/058695 | 8/2002 |
| WO | WO 02/059083 | 8/2002 |
| WO | WO02/060869 | 8/2002 |
| WO | WO 02/102315 | 12/2002 |
| WO | WO 2005/014558 | 2/2005 |
| WO | WO 2006/021547 A1 * | 2/2006 |

OTHER PUBLICATIONS

U.S. Appl. No. 11/613,517, filed Dec. 20, 2006, Adams et al.
U.S. Appl. No. 11/613,598, filed Dec. 20, 2006, Adams et al.
U.S. Appl. No. 11/839,830, filed Aug. 16, 2007, Adams et al.
U.S. Appl. No. 11/839,833, filed Aug. 16, 2007, Adams et al.
U.S. Appl. No. 11/839,834, filed Aug. 16, 2007, Adams et al.
U.S. Appl. No. 11/908,340, filed Sep. 11, 2007, Boehm et al.
U.S. Appl. No. 11/908,435, filed Sep. 12, 2007, Callahan et al.
U.S. Appl. No. 11/908,440, filed Sep. 12, 2007, Callahan et al.
U.S. Appl. No. 11/908,839, filed Sep. 17, 2007, Callahan et al.
U.S. Appl. No. 11/871,039, filed Oct. 11, 2007, Adams et al.
Adams et al., Progress in Medicinal Chemistry, vol. 38, pp. 2-61 (2001).
Armarego, W., Chem. Soc., Quinazolines, Part IV. (JCS OA9) p. 561 (1962).
Boehm et al., J. Med. Chem. vol. 39, pp. 3929-3937 (1996).
Votta et al., Bone, vol. 15, No. 5, pp. 533-538 (1994).
Bradlerova et al., Chem. Zvesti, vol. 29 (6), pp. 795-802 (1975).
de Silva et al., J. Chem. Soc., vol. 4, pp. 685-690 (1995).
Engel & Steglich, Liebigs Ann. Chem., p. 1916 (1978).
Ferles et al., Collect. Czech. Chem. Commun., 5 (46), pp. 1167-1172 (1981).
Fischer et al., Rec. Trav. Chim. Pays. Bas., vol. 84, p. 439 (1965).
Fulmer et al., J. Heterocycl. Chem., vol. 17 (4), pp. 799-800 (1980).
Gilbert, E., Synthesis, pp. 30-32 (1972).
Han et al., Science, vol. 265, pp. 808-811 (1994).
Hunter et al., Academic Press, San Diego, vol. 200, p. 3 (1991).
Irwin et al., Archives of Internal Medicine, vol. 157 (17), pp. 1981-1987 (1997).
Ishibashi et al., Chem. Pharm. Bull., vol. 37 (8), pp. 2214-2216 (1989).
Johnson et al., PG.A., J.Chem.Soc., Perkin Trans., vol. 1, pp. 895-905 (1996).
Jurkowska-Kowalczyk, R., Chem., vol. 51 (6), pp. 1191-1199 (1977).
Katritzky et al., Synthesis, pp. 45-47 (Jan. 1993).
Kawasaki et al., J. Bio. Chem., vol. 272 (30), pp. 18518-18521 (1997).
Mikailu et al., Zh. Obshch. Khim., vol. 56 (7), pp. 1513-1517 (1986).
Morton et al., Tetrahedron Letters, p. 4123 (1982).
Protecting Groups in Organic Synthesis, 2$^{nd}$ Edition, Greene TW and Wuts PSM, Wiley-Interscience, New York, pp. 10-174 (Hydroxyl and Phenolic) and pp. 309-403 (NH protection) (1991).
Santilli et al., J. Heterocycl Chem., vol. 8, pp. 445-453 (1971).
Snieckus, V., Tetrahedron Letters, vol. 29, p. 2135 (1988).
Hunt, et al., *Bioorganic & Medicinal Chemistry Letters*, vol. 13, pp. 467-470 (2003).
Hare, et al., *J. Med Chem.*, vol. 47 pp. 4731-4740 (2004).
Stille et al., J. Amer. Chem. Soc., vol. 109, p. 5478 (1978).
Strzybny et al., J. Org. Chem., vol. 28, p. 3381 (1963).
Terashimia et al., M., Chem. Pharm. Bull., vol. 11, p. 4755 (1985).
Thompson et al., J. Org. Chem., vol. 49, p. 5237 (1984).
Uno et al., Bull. Chem. Soc. Japan., vol. 69, pp. 1763-1767 (1996).
Vartanyan et al., vol. 40, (9), pp. 552-560 (1987).
Borrel, et al., Coll. Czech. Chem. Commun., 1996, 61(6) pp. 901-909.
Hurlbert, et al., J. Med Chem., 1968, vol. 11, pp. 703-707.
Baker et al., J. Heterocyclic Chem., 1964, vol. 1, pp. 263-270.
Anderson et al., J. Org. Chem., 1977, vol. 42, p. 993.
Schoffstall et al., J. Org. Chem., 1971, 36(16), pp. 2385-2387.
Victory et al., Heterocycles, 1985, 23(5), pp. 1135-1141.
Gallagher et al., Bioorganic and Med Chem, vol. 5(1), pp. 49-64 (1997).
Garigipati, R., Tetrahedron Letters, vol. 31, p. 190 (1989).
Kumada et al., Tetrahedron Letters, vol. 22, p. 5319 (1981).
Lamartina et al., Boll. Chim. Farm. vol. 129 (12), pp. 314-316 (1990).
Victory et al., Heterocycles, 1985, 23(8), pp. 1947-1950.

Victory et al., Afinidad, Mar. 1989, vol. 46, pp. 107-113 (Spanish).

Klotzer et al., Monatsh Chem., 1965, vol. 96, p. 1567.

Rewcastle et al., Journal of Medicinal Chemistry, 1996 39(6), pp. 1823-1835.

Victory et al., J. Heterocycl. Chem, 1988, vol. 25, pp. 245-247.

Nishikawa et al., Chemical Pharm. Bull., 1976, vol. 24(9), pp. 2057-2077.

Carboni et al., *Gazzetta Chimica Italiana*, vol. 97(8) pp. 1262-1273 (1967).

Carboni et al., *Gazzetta Chimica Italiana*, vol. 98(10) pp. 1174-1188 (1968).

Ferrarini et al., *Journal of Heterocyclic Chemistry*, vol. 21(2) pp. 417-419 (1984).

Ferrarini et al., *Journal of Heterocyclic Chemistry*, vol. 34(5) pp. 1501-1510 (1997).

Zavyalov, et al., Khim Farm Zh, vol. 26(3), p. 88 (1992) (With Translation).

* cited by examiner

PROCESS FOR PREPARING PYRIDO[2,3-*D*]PYRIMIDIN-7-ONE AND 3,4-DIHYDROPYRIMIDO[4,5-*D*]PYRIMIDIN-2(1*H*)-ONE DERIVATIVES

RELATED APPLICATIONS

This application claims the benefit of priority from provisional application U.S. Ser. No. 60/665,154, filed 25 Mar. 2005.

FIELD OF THE INVENTION

This invention relates to a novel process to produce pyrido[2,3-d]pyrimidin-7-one containing compounds or 3,4-dihydropyrimido[4,5-d]pyrimidin-2(1H)-one containing compounds.

BACKGROUND OF THE INVENTION

Preparation of 2,4,8-trisubstituted pyrido[2,3-d]pyrimidin-7-one has been demonstrated by a small, but limited, number of methods. In general, these methods either include lengthy synthetic sequence (e.g., more than 5 steps in the longest linear sequence from commercially available starting materials) or are not conducive for use in structure-activity relationship studies [e.g., not amenable to multi-dimensional (>or=2-D) array syntheses]. Doherty, J. B. et al., (Merck, U.S. Pat. No. 6,809,199) discloses an eight-step method to prepare intermediates with structures similar to (II) wherein C4 and N8 have already been substituted with phenyl groups. Mauro, A. et al. (Pharmacia, US 2004/0009993) reported a nine-step method to prepare intermediates with structures similar to (II) wherein C4 is substituted with $C_1$-$C_6$ alkyl or $C_1$-$C_6$ arylalkyl and N8 has been connected with a phenyl group. Adams, J. L. et al. (SmithKline Beecham: WO 02/059083; WO 03/088972; Tetrahedron Letters, 2003, Vol. 44, pages 4567-4570) discloses a four-step method to prepare intermediates with structures similar to (II) wherein the C4 position has already been substituted via a Suzuki cross coupling reaction and N8 is substituted with alkyl or aryl.

However, despite all of these methods there still remains a need for an efficient method to prepare 2,4,8-trisubstituted pyrido[2,3-d]pyridine-7-one that can independently optimize the substituents at C2 and C4.

SUMMARY OF THE INVENTION

The present invention is directed to the novel compounds of Formula (II):

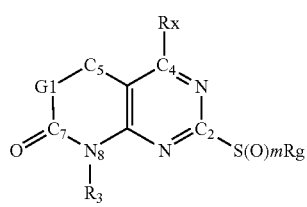

(II)

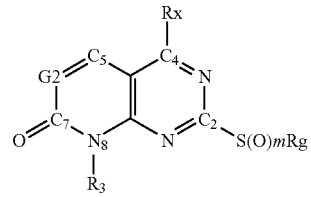

(IIa)

wherein
G1 is $CH_2$ or NH;
G2 is CH or nitrogen;
Rx is chloro, bromo, iodo, or O—S(O)$_2$CF$_3$;
$R_g$ is a $C_{1-10}$ alkyl;
m is 0, or an integer having a value of 1, or 2;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted.

The present invention is also directed to a novel process to make compounds of Formula (II) wherein m=0, which comprises reacting a compound of the formula:

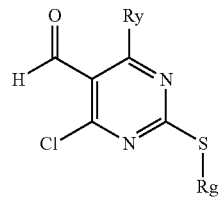

(Va)

wherein
Ry is chloro, bromo, iodo, O—S(O)$_2$CF$_3$; and
Rg is a $C_{1-10}$ alkyl;
with a olefin forming reagent in a suitable base to yield a compound of Formula (II),
wherein G2 is CH, which may optionally be reduced to a compound of Formula (IIa) under standard reducing conditions if desired.

The present invention is also directed to the novel compounds of Formula (V)

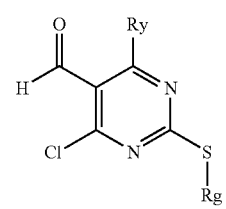

(V)

wherein
Ry is bromo, iodo, O—S(O)$_2$CF$_3$; and
Rg is a $C_{1-10}$ alkyl.

The present invention is also directed to novel compounds of Formula (III):

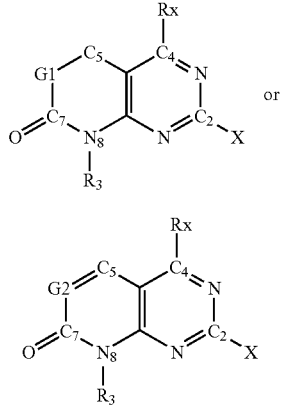

wherein
G1 is CH$_2$ or NH:
G2 is CH or nitrogen;
Rx is chloro, bromo, iodo, or O—S(O)$_2$CF$_3$;
X is R$_2$, OR$_{2'}$, S(O)$_m$R$_{2'}$, (CH$_2$)$_n$N(R$_{11}$)S(O)$_m$R$_{2'}$, (CH$_2$)$_n$N(R$_{11}$)C(O)R$_{2'}$, (CH$_2$)$_n$NR$_4$R$_{14}$ or (CH$_2$)$_n$N(R$_{2'}$)(R$_{2''}$), or N(R$_{10'}$)—R$_h$—NH—C(=N—CN)NR$_q$R$_q{}'$;
X$_1$ is N(R$_{11}$), O, S(O)$_m$, or CR$_{10}$R$_{20}$;
R$_h$ is selected from an optionally substituted C$_{1-10}$ alkyl, —CH$_2$—C(O)—CH$_2$—, —CH$_2$CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$, —CH$_2$—C(O)O—CH$_2$—CH$_2$—, or —CH$_2$—CH$_2$—O—C(O)CH$_2$—;
R$_q$ and R$_q{}'$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties, excluding hydrogen, are optionally substituted, or R$_q$ and R$_q{}'$ together with the nitrogen to which they are attached form a 5 to 7 membered optionally substituted ring, which ring may contain an additional heteroatom selected from oxygen, nitrogen or sulfur;
R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or R$_2$ is the moiety (CR$_{10}$R$_{20}$)$_q$X$_1$(CR$_{10}$R$_{20}$)$_q$C(A$_1$)(A$_2$)(A$_3$), or C(A$_1$)(A$_2$)(A$_3$);
R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;
R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally substituted; or wherein R$_{2''}$ is the moiety (CR$_{10}$R$_{20}$)$_t$X$_1$(CR$_{10}$R$_{20}$)$_q$C(A$_1$)(A$_2$)(A$_3$);

A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;
A$_3$ is hydrogen or is an optionally substituted C$_{1-10}$ alkyl;
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;
R$_4$ and R$_{14}$ are each independently selected from hydrogen, C$_{1-10}$ alkyl, C$_{3-7}$ cycloalkyl, C$_{3-7}$ cycloalkylC$_{1-4}$alkyl, aryl, aryl-C$_{1-4}$ alkyl, heterocyclic, heterocylic C$_{1-4}$ alkyl, heteroaryl or a heteroaryl C$_{1-4}$ alkyl moiety, and wherein each of these moieties, excluding hydrogen, may be optionally substituted; or the R$_4$ and R$_{14}$ together with the nitrogen which they are attached form an optionally substituted heterocyclic ring of 4 to 7 members, which ring optionally contains an additional heteroatom selected from oxygen, sulfur or nitrogen;
R$_{10}$ and R$_{20}$ are independently selected from hydrogen or C$_{1-4}$alkyl;
R$_{10'}$ is independently selected at each occurrence from hydrogen or C$_{1-4}$alkyl;
R$_{11}$ is independently selected from hydrogen or C$_{1-4}$alkyl;
n' is independently selected at each occurrence from 0 or an integer having a value of 1 to 10;
m is independently selected at each occurrence from 0 or an integer having a value of 1 or 2;
q is 0 or an integer having a value of 1 to 10;
q' is 0, or an integer having a value of 1 to 6; or
t is an integer having a value of 2 to 6.

The present invention is also directed to a process for making a compound Formula (III) or (IIa), which comprises reacting a compound of formula (II) or (IIa)

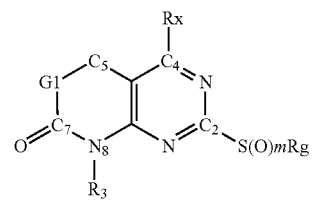

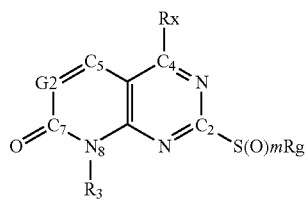

wherein
G1 is CH$_2$ or NH:
G2 is CH or nitrogen;
Rx is chloro, bromo, iodo, or O—S(O)$_2$CF$_3$;
R$_g$ is a C$_{1-10}$ alkyl;
m is an integer having a value of 1, or 2;
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclyl$C_{1-10}$ alkyl moiety, and wherein each of these moieties may be optionally substituted.

with the compound X—Y, wherein X is $R_2$, $OR_{2'}$, $S(O)_mR_{2'}$, $(CH_2)_nN(R_{11})S(O)_mR_{2'}$, $(CH_2)_nN(R_{11})C(O)R_{2'}$, $(CH_2)_nNR_4R_{14}$, or $(CH_2)_nN(R_{2'})(R_{2''})$, or $N(R_{10'})$—$R_h$—NH—C(=N—CN)NRqRq'; and $R_2$, $R_{2'}$, m, n', $R_{11}$, $R_{10'}$, $R_h$ and RqRq' are as defined according to Formula (III) herein; and Y is hydrogen, a metal, a boronic acid derivative, or a trialkyl tin derivative, in an anhydrous organic solvent which does not contain a nucleophile to yield a compound of Formula (III); provided that when Y is hydrogen then
  a) X=$OR_{2'}$, or X is $S(O)_mR_{2'}$ (and m=0); or
  b) X is $(CH_2)_nN(R_{10'})S(O)_mR_{2'}$, $(CH_2)_nN(R_{10'})C(O)R_{2'}$, $(CH_2)_nNR_4R_{14}$, or $(CH_2)_nN(R_{2'})(R_{2''})$ and n'=0; or
  c) X=$R_2$ and $R_2$=$(CR_{10}R_{20})_{q'}X_1(CR_{10}R_{20})_qC(A_1)(A_2)(A_3)$, q'=0, and $X_1$ is $N(R_{10'})$, O, $S(O)_m$ and m=0.
  d) when X is $N(R_{10'})$—$R_h$—NH—C(=N—CN)NRqRq'; and when Y is a metal, such as Li, Mg, or any other appropriate metal or metal complexes; then
  a) X is $R_2$, and $R_2$ is $C_{1-10}$ alkyl, $C_{3-7}$ cycloalkyl, $C_{3-7}$ cycloalkyl$C_{1-10}$ alkyl, aryl, aryl$C_{1-10}$ alkyl, heteroaryl, heteroaryl $C_{1-10}$ alkyl, heterocyclic, or a heterocyclyl$C_{1-10}$ alkyl moiety; and when Y is a boronic acid, $(B(OH)_2)$ or boronic ester derivatives
  a) X=$R_2$, and $R_2$=aryl, or heteroaryl; and when Y is a trialkyl tin derivative, such as $(C_{1-4}$ alkyl$)_3$Sn, then
  a) X=$R_2$, and $R_2$=aryl, or heteroaryl.

DETAILED DESCRIPTION OF THE INVENTION

The present invention is an alternative process for preparation of compounds having a pyrido[2,3-d]pyrimidin-7-one template or a 3,4-dihydropyrimido[4,5-d]pyrimidin-2(1H)-one derivatives.

This novel process provides for facile variation of the C4 position in the both of these templates, and therefore ease of use in the making of a combinatorial array.

The process as will be described herein provides for different ($R_1$) substituents to be introduced at the $C_4$ position of the compounds with the general structure of Formula I, late in a synthetic sequence after the pyrido[2,3-d]pyrimidin-7-one or the 3,4-dihydropyrimido[4,5-d]pyrimidin-2(1H)-one template has already been substituted with a substituent ("X" in Formula I) at the $C_2$ position and with another substituent ("$R_3$" in Formula I) at the $N_8$ position.

Generically the reaction is:

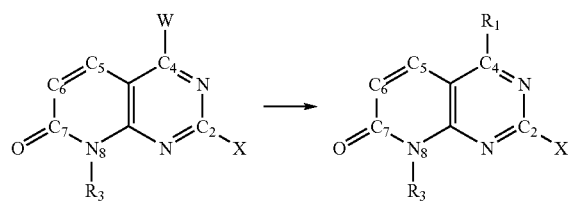

wherein W is a leaving group such as chlorine, bromine, iodine, $OS(O)CF_3$; and $R_1$, $R_3$ and X are as defined in Formula (N).

Compounds of Formula (I) are represented by the structure:

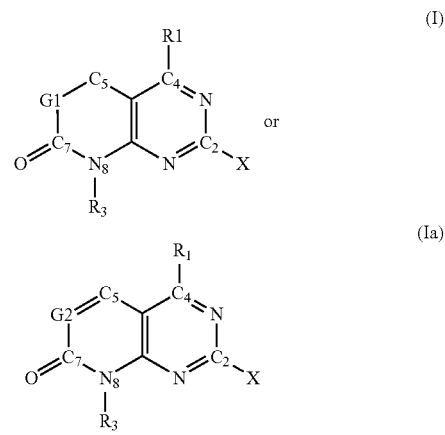

wherein

G1 is $CH_2$, or NH:

G2 is CH or nitrogen;

$R_1$ is an aryl, aryl $C_{2-10}$ alkyl, heteroaryl, heteroaryl $C_{2-10}$ alkyl; aryl $C_{2-10}$ alkenyl, aryl$C_{2-10}$ alkynyl, heteroaryl $C_{2-10}$ alkenyl, heteroaryl $C_{2-10}$ alkynyl, $C_{2-10}$alkenyl, or $C_{2-10}$ alkynyl moiety, which moieties may be optionally substituted;

X is $R_2$, $OR_{2'}$, $S(O)_mR_{2'}$, $(CH_2)_{n'N(R10)'}S(O)_mR_{2'}$, $(CH_2)_nN(R_{10})C(O)R_{2'}$, $(CH_2)_nNR_4R_{14}$, $(CH_2)_nN(R_{2'})(R_{2''})$, or $N(R_{10'})$—$R_h$—NH—C(=N—CN)NRqRq';

$X_1$ is $N(R_{11})$, O, $S(O)_m$, or $CR_{10}R_{20}$;

$R_h$ is selected from an optionally substituted $C_{1-10}$ alkyl, —$CH_2$—C(O)—$CH_2$—, —$CH_2CH_2$—O—$CH_2$—$CH_2$—, —$CH_2$—C(O)N($R_{10'}$)$CH_2$—$CH_2$—, —$CH_2$—N($R_{10'}$)C(O)$CH_2$—, —$CH_2$—CH(O$R_{10'}$)—$CH_2$, —$CH_2$—C(O)O—$CH_2$—$CH_2$—, or —$CH_2$—$CH_2$—O—C(O)$CH_2$—;

$R_q$ and $R_{q'}$ are independently selected at each occurrence from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties, excluding hydrogen, are optionally substituted, or $R_q$ and $R_{q'}$ together with the nitrogen to which they are attached form a 5 to 7 membered optionally substituted ring, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_{q'}X_1(CR_{10}R_{20})_qC(A_1)(A_2)(A_3)$, or $(CR_{10}R_{20})_qC(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally substituted; or wherein $R_{2''}$ is the moiety $(CR_{10}R_{20})_tX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl$C_{1-10}$ alkyl, or a heterocyclyl$C_{1-10}$ alkyl moiety, and wherein each of these moieties may be optionally substituted;

$R_4$ and $R_{14}$ are each independently selected at each occurrence from hydrogen, $C_{1-10}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is independently selected at each occurrence from hydrogen or $C_{1-4}$alkyl;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6;

t is an integer having a value of 2 to 6; or a pharmaceutically acceptable salt, solvate or physiologically functional derivative thereof.

Compounds of Formula (I) having a similar template are described in WO 01/64679, WO 02/059083, and WO 03/088972 whose disclosures are incorporated by reference in their entirety herein.

It should be noted that the difference between compounds of Formula (I) and (Ia), as well as (II) and (IIa), (III) and (IIIa) lie in the unsaturation of the ring at the C5 position and the 6-position of the ring which may be a carbon or a nitrogen. The remaining variables on the ring are the same otherwise, e.g. Rx, R1, R3, etc. for each formula. Unless otherwise specified, the substitution applicable to Formula (I) is also applicable to Formula (Ia), etc.

For all of the formulas herein having an $R_1$ substitutent, $R_1$ is suitably an aryl, aryl $C_{2-10}$ alkyl, heteroaryl, heteroaryl $C_{2-10}$ alkyl; aryl $C_{2-10}$ alkenyl, aryl$C_{2-10}$ alkynyl, heteroaryl $C_{2-10}$ alkenyl, heteroaryl $C_{2-10}$ alkynyl, $C_{2-10}$ alkenyl, or $C_{2-10}$ alkynyl moiety, which moieties may be optionally substituted.

In one embodiment $R_1$ is an optionally substituted aryl, or an optionally substituted heteroaryl ring. Preferably, $R_1$ is an optionally substituted aryl, more preferably an optionally substituted phenyl.

$R_1$ may be substituted one or more times, suitably 1 to 4 times, independently at each occurrence by halogen, $C_{1-4}$ alkyl, halo-substituted-$C_{1-4}$ alkyl, cyano, nitro, aryl, aryl$C_{1-4}$ alkyl, $(CR_{10}R_{20})_{v'}NR_dR_{d'}$, $(CR_{10}R_{20})_{v}C(O)R_{12}$, $SR_5$, $S(O)R_5$, $S(O)_2R_5$, $(CR_{10}R_{20})_{v}OR_{13}$, $(CR_{10}R_{20})_{v}C(Z)NR_4R_{14}$, $(CR_{10}R_{20})_{v}C(Z)OR_8$, $(CR_{10}R_{20})_{v}COR_{a'}$, $(CR_{10}R_{20})_{v}C(O)H$, $ZC(Z)R_{11}$, $N(R_{10'})C(Z)R_{11}$, $N(R_{10'})S(O)_2R_7$, $C(Z)N(R_{10'})(CR_{10}R_{20})_{v}R_b$, $C(Z)O(CR_{10}R_{20})_{v}R_b$, $N(R_{10'})C(Z)(CR_{10}R_{20})_{v}R_b$; $N(R_{10'})C(Z)N(R_{10'})(CR_{10}R_{20})_{v}R_b$; or $N(R_{10'})OC(Z)(CR_{10}R_{20})_{v}R_b$.

Suitably, $R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety, which moieties excluding hydrogen, may all be optionally substituted.

In one embodiment of the invention when the $R_1$ moiety is phenyl, and the phenyl ring is substituted by the moiety $(R_{1''})$ wherein $R_{1''}$ is selected from $C(Z)N(R_{10'})(CR_{10}R_{20})_{v}R_b$, $C(Z)O(CR_{10}R_{20})_{v}R_b$, $N(R_{10'})C(Z)(CR_{10}R_{20})_{v}R_b$, $N(R_{10})C(Z)N(R_{10'})(CR_{10}R_{20})_{v}R_b$, or $N(R_{10})OC(Z)(CR_{10}R_{20})_{v}R_b$. The phenyl ring may also be additionally substituted by the substituent $(R_{1'})g$, wherein g is 0 or an integer having a value of 1, 2, 3, or 4. In one embodiment of the invention, g is 0, 1 or 2. When the $R_1$ moiety is substituted by $R_{1''}$ then these substituents are preferably in the 3- or 4-position of the phenyl ring.

Suitably, the $R_{1'}$ moiety is independently selected at each occurence from halogen, $C_{1-4}$ alkyl, halo-substituted-$C_{1-4}$ alkyl, cyano, nitro, $(CR_{10}R_{20})_{v}NR_dR_{d'}$, $(CR_{10}R_{20})_{v}C(O)R_{12}$, $SR_5$, $S(O)R_5$, $S(O)_2R_5$, or $(CR_{10}R_{20})_{v}OR_{13}$.

In one embodiment of the invention, $R_1$ is substituted by $C(Z)N(R_{10'})(CR_{10}R_{20})_{v}R_b$, or $N(R_{10'})C(Z)(CR_{10}R_{20})_{v}R_b$, and $R_{1'}$ is independently selected at each occurrence from $C_{1-4}$ alkyl, such as methyl, or halogen, such as fluorine or chlorine or bromine, or halo-substituted-$C_{1-4}$ alkyl, such as $CF_3$. In a further embodiment $R_1$ is an aryl moiety, preferably a phenyl ring.

In another embodiment of the invention $R_1$ is substituted by $C(Z)N(R_{10'})(CR_{10}R_{20})_{v}R_{b'}$ and $R_{1'}$ is independently selected at each occurrence from $C_{1-4}$ alkyl, such as methyl, or halogen, such as fluorine, chlorine or bromine.

In one embodiment, $R_{1'}$ is independently selected at each occurrence from halogen, $C_{1-4}$ alkyl, or halo-substituted-$C_{1-4}$ alkyl. In another embodiment, $R_{1'}$ is independently selected at each occurrence from fluorine, chlorine, methyl, or $CF_3$. In a further embodiment $R_1$ is an aryl moiety, preferably a phenyl ring.

In one embodiment, $R_1$ is an aryl moiety, preferably a phenyl ring, optionally substituted one or more times by halogen, $C_{1-4}$ alkyl, or halo-substituted-$C_{1-4}$ alkyl. More preferably, the phenyl ring is substituted in the 2, 4, or 6-position, or di-substituted in the 2,4-position, such as 2-fluoro, 3-fluoro, 4-fluoro, 2,4-difluoro, or 2-methyl-4-fluoro; or tri-substituted in the 2,4,6-position such as 2,4,6-trifluoro.

In another embodiment $R_1$ is an aryl moiety, preferably a phenyl ring, optionally substituted one or more times by halogen, $C_{1-4}$ alkyl, halo-substituted-$C_{1-4}$ alkyl, $SR_5$, $S(O)R_5$, $S(O)_2R_5$, $(CR_{10}R_{20})_{v}OR_{13}$, $(CR_{10}R_{20})_{v}C(Z)NR_4R_{14}$, $C(Z)N(R_{10'})(CR_{10}R_{20})_{v}R_b$, and $(CR_{10}R_{20})_{v}C(Z)OR_8$. In one embodiment, $R_8$ is hydrogen, or $C_{1-4}$ alkyl, $R_{13}$ is hydrogen, or $C_{1-4}$ alkyl, such as methyl; Rb is suitably hydrogen, $C_{1-4}$ alkyl, aryl, or heteroaryl. Preferably, $R_1$ is a phenyl substituted by 2-methoxy, 3-methoxy, 4-methoxy, 2-chloro, 3-chloro, 4-chloro, 2-fluoro, 3-fluoro, 4-fluoro, 4-difluoro, 2,4,6-trifluoro, 3,4-difluoro, 3,5-difluoro, 2-methyl-4-fluoro, 2-methyl-4-chloro, 2-methylsulfanyl, 3-methylsulfanyl, 4-methylsulfanyl, 2-phenyl, 3-phenyl, 4-phenyl, 2-methyl, 3-methyl, 4-methyl, 3-fluoro-4-phenyl, 2-hydroxy, 3-hydroxy, 4-hydroxy, 2-methylsulfonyl, 3-methylsulfonyl, 4-methylsulfonyl, 3-N-cyclopropylamide, 2-methyl-3-fluoro-5-N-cyclopropylamide, 2-C(O)OH, 3-C(O)OH, 4-C(O)OH, 2-methyl-5-C(O)OH, 2-methyl-3-C(O)OH, 2-methyl-4-C(O)OH, 2-methyl-3-F-5-C(O)OH, 4-F-phenyl1-amide, 2-ethyl-5-C(O)OH, 2-ethyl-3-C(O)OH, 2-ethyl-4-C(O)OH, 2-methyl-5-dimethylamide, 2-methyl-4-dimethylamide, 5-dimethylamide, and 4-dimethylamide.

A preferred $R_1$ moiety is 4-methyl-N-1,3-thiazol-2-ylbenzamide, N-(4-fluorophenyl)-4-methylbenzamide, 4-methyl-N-propylbenzamide, 4-methyl-N-isopropylbenzamide, 2-methyl-4-fluorophenyl, or 2-methyl-3-fluorophenyl, and 2-methyl-4-chlorophenyl.

Suitably, when $R_1$ is a heteroaryl moiety, the ring is not attached to the pharmacophore via one of the heteroatoms, such as nitrogen to form a charged ring. For instance, a pyridinyl ring would be attached through a carbon atom to yield a 2-, 3- or 4-pyridyl moiety, which is optionally substituted.

If $R_1$ is substituted by $C(Z)N(R_{10'})(CR_{10}R_{20})_vR_b$, $C(Z)O(CR_{10}R_{20})_vR_b$, or $N(R_{10'})C(Z)(CR_{10}R_{20})_vR_b$; $N(R_{10'})C(Z)N(R_{10'})(CR_{10}R_{20})_vR_b$; $N(R_{10'})OC(Z)(CR_{10}R_{20})_vR_b$; it is preferably in the 4 or 5 position of the ring. If the ring is additionally substituted by $R_{1'}$ and $R_1$ is a phenyl ring, then the additional substituents are present in the ortho position, if a second $R_{1'}$ moiety is also substituted on the ring, then preferably, this second $R_{1'}$ substitution is not in the other ortho position.

Suitably, $R_{a'}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vN(R_{10'})S(O)_2R_7$, or $(CR_{10}R_{20})_vNR_4R_{14}$; and wherein the aryl, arylalkyl, heteroaryl, heteroaryl alkyl may be optionally substituted.

Suitably, $R_d$ and $R_{d'}$ are each independently selected from hydrogen, $C_{1-4}$ alkyl, $C_{3-5}$ cycloalkyl, $C_{3-5}$ cycloalkyl$C_{1-4}$ alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$, and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_4$ and $R_{14}$ cyclized ring are optionally substituted, 1 to 4 times, independently by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; S(O)mRf; C(O)Rj; C(O)ORj; C(O)$NR_4'R_{14'}$, $NR_4C(O)C_{1-4}$alkyl; $S(O)_2NR_4'R_{14'}C_{1-4}$ alkyl; $NR_4'R_{14'}S(O)_2 C_{1-4}$ alkyl; or $NR_4'R_{14'}$.

Suitably $R_{9'}$ is independently selected at each occurrence from hydrogen, or $C_{1-4}$ alkyl.

Suitably, Z is independently at each occurrence selected from oxygen or sulfur.

Suitably, m is independently selected at each occurrence from 0 or an integer having a value of 1 or 2.

Suitably, v is 0 or an integer having a value of 1 to 2.

Suitably, v' is 0 or an integer having a value of 1 or 2.

Suitably, $R_{10}$ and $R_{20}$ are independently selected at each occurrence from hydrogen or $C_{1-4}$ alkyl.

Suitably, $R_{10'}$ is independently selected at each occurrence from hydrogen or $C_{1-4}$ alkyl.

Suitably, $R_{11}$ is independently selected at each occurrence from hydrogen, or $C_{1-4}$ alkyl.

Suitably, $R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or heterocyclyl$C_{1-4}$ alkyl, and wherein these moieties, excluding hydrogen, may be optionally substituted.

Suitably, $R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted and wherein these moieties, excluding hydrogen, may be optionally substituted 1 to 4 times by halogen; halosubstituted $C_{1-4}$ alkyl; $C_{1-4}$ alkyl; hydroxy; hydroxy substituted $C_{1-4}$alkyl; $C_{1-4}$alkoxy; halosubstituted $C_{1-4}$ alkoxy; S(O)m$C_{1-4}$ alkyl; —C(O), C(O)$C_{1-4}$ alkyl; or $NR_{21'}$, $R_{31'}$.

Suitably, $R_{21'}$ and $R_{31'}$ are each independently selected from hydrogen or $C_{1-4}$ alkyl, or $R_{21'}$ and $R_{31'}$ together with the nitrogen to which they are attached cyclize to form a 5 to 7 membered ring which optionally contains an additional heteroatom selected from oxygen, nitrogen or sulfur.

The $R_b$ moieties, excluding hydrogen, may be optionally substituted, one or more times, preferably 1 to 4 times independently at each occurrence by halogen, such as fluorine, chlorine, bromine or iodine; hydroxy; hydroxy substituted $C_{1-10}$alkyl; $C_{1-10}$ alkoxy, such as methoxy or ethoxy; halo-substituted $C_{1-}$ alkoxy; $OR_8$, such as methoxy, ethoxy or phenoxy; $SR_5$, $S(O)R_5$, $S(O)_2R_5$, such as methyl thio, methylsulfinyl or methyl sulfonyl; $C(O)R_j$; $C(O)OR_j$; $C(O)NR_{4''}R_{14''}$; cyano; nitro; $NR_{15}R_{25}$; -Z'-$(CR_{10}R_{20})$s-Z'; $C_{1-10}$alkyl; such as methyl, ethyl, propyl, isopropyl, t-butyl, n-butyl, etc.; $C_{3-7}$cycloalkyl or a $C_{3-7}$cycloalkyl $C_{1-10}$ alkyl group, such as cyclopropyl, or cyclopropyl methyl, or cyclopropyl ethyl, etc.; halosubstituted $C_{1-10}$ alkyl, such $CF_2CF_2H$, $CH_2CF_3$, or $CF_3$; an optionally substituted aryl, such as phenyl, or an optionally substituted aryl $C_{1-10}$alkyl, such as benzyl or phenethyl; an optionally substituted heterocyclic or heterocyclic $C_{1-10}$alkyl, or an optionally substituted heteroaryl or heteroaryl $C_{1-10}$alkyl, and wherein these aryl, heteroaryl, and heterocyclic containing moieties may also be substituted one to two times by halogen, hydroxy, hydroxy substituted alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, when $R_b$ is an optionally substituted $C_{1-10}$alkyl, the moiety includes but is not limited to a methyl, ethyl, n-propyl, isopropyl, t-butyl, n-butyl, isobutyl, 1,2-dimethylpropyl, 2,2-dimethylpropyl, heptyl, 2-methylpropyl; a halo-substituted alkyl, such as 2,2,2-trifluroethyl, trifluromethyl, 2-fluoroethyl; a cyano substituted alkyl, such as cyanomethyl, cyanoethyl; an alkoxy, thio or hydroxy substituted alkyl, such as 2-methoxy-ethyl, 2-hydroxy propyl or serinol, or an ethylthioethyl.

In an alternative embodiment, when Rb is an optionally substituted $C_{1-10}$alkyl the moiety is a methyl, ethyl, n-propyl, isopropyl, t-butyl, n-butyl, or 2,2-dimethylpropyl or 2-hydroxy propyl group.

Suitably, when $R_b$ is an optionally substituted heteroaryl, heteroaryl alkyl they are as defined in the definition section, and include but are not limited, to furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

Suitably, when $R_b$ is an optionally substituted heterocyclic, heterocyclic alkyl, they are as defined in the definition section, In one embodiment of the invention, when $R_b$ is an optionally substituted heteroaryl, heteroaryl alkyl, heterocyclic or heterocyclic alkyl, the moiety is a 1,3-thiazol-2-yl, 5-methyl-1,3-thiazol-2-yl, isoquinoline, 3-thiophene, indol-5yl, pyridin-3-yl, pyridine-4-yl, indazolyl, benzothiazolyl, 2-methyl-1,3-benzothiazol-5-yl, pyrazol-3-yl, 4-morpholino, 2-furanyl, 2-furanylmethyl, 2-thienyl, 2-thienylmethyl, tetrahydro-2H-pyran-4yl, tetrahydro-2H-pyran-4yl methyl, tetrahydro-2-furanyl, or tetrahydro-2-furanylmethyl, 1H-imidazol-4-yl or 1H-imidazol-4-ylethyl.

In an alternative embodiment, when Rb is an optionally substituted heteroaryl the moiety is a 1,3-thiazol-2-yl or 5-methyl-1,3-thiazol-2-yl, isoquinolinyl, thiophene, pyridinyl, indazolyl, benzothiazolyl, e.g. 2-methyl-1,3-benzothiazol-5-yl.

In another embodiment, the heteroaryl ring is an optionally substituted thiazolyl, pyridyl, or thiophene ring.

Suitably, when $R_b$ is an optionally substituted aryl or arylalkyl moiety, the aryl containing is unsubstituted or substituted independently at each occurrence one or more times by halogen, alkyl, cyano, $OR_8$, $SR_5$, $S(O)_2R_5$, $C(O)R_j$, $C(O)OR_j$, -Z'-$(CR_{10}R_{20})$s-Z', halosubstituted $C_{1-10}$ alkyl, or an optionally substituted aryl.

In one embodiment, $R_b$ is a phenyl, or napthylene, 2-fluorophenyl, 3-fluorophenyl, 4-fluorophenyl, 2,3-difluorphenyl, 2,4-difluorophenyl, 3,4-difluorophenyl, 3,5-difluorophenyl, 3-chlorophenyl, 4-chlorophenyl, 3-chloro-4-fluorophenyl, 2-methyl phenyl, 3-methylphenyl, 4-methylphenyl, 6-methyl phenyl, 2-methyl phenyl, 3-amino phenyl, 3,4-dimethyl phenyl, 4-methyl-3-fluorophenyl, 4-trifluorophenyl, 4-ethoxyphenyl, 4-methoxyphenyl, 3-cyanophenyl, 4-cyanophenyl, 4-thiomethylphenyl, 4-acetylphenyl, 4-dimethylaminophenyl, benzyl, phenethyl, phenylpropyl, 2,3-difluoro-benzyl, 3,5-difluoro-benzyl, biphenyl, 4'-fluorobiphenyl, 4-sulfonamindo-2-methylphenyl, or 3-phenyloxyphenyl, 4-phenyloxyphenyl, 4-(1-piperidinylsulfonyl)-phenyl, or 3-(aminocarbonyl)phenyl.

In another embodiment, $R_b$ is a phenyl, 2-fluorophenyl, 3-fluorophenyl, 4-fluorophenyl, 2,4-difluorphenyl, 3,4-difluorophenyl, 3,5-difluorophenyl, 3-chlorophenyl, 4-chlorophenyl, 3-chloro-4-fluorophenyl, 4-methyl-3-fluorophenyl, 4-trifluorophenyl, 2-methylphenyl, 3-methylphenyl, 4-ethoxyphenyl, 4-methoxyphenyl, 3-cyanophenyl, 4-cyanophenyl, 4-thiomethylphenyl, 4-acetylphenyl, 4-dimethylaminophenyl, biphenyl, 4'-fluorobiphenyl, 4-sulfonamindo-2-methylphenyl, 3-phenyloxyphenyl, benzyl, or phenethyl.

Suitably, when $R_b$ is an optionally substituted cycloalkyl or cycloalkyl alkyl moiety, the moiety is a cyclopropyl, cyclobutyl, cyclopentyl, cyclohexyl, cyclopropylmethyl, or a cyclopentylmethyl. In another embodiment, $R_b$ is a cyclopropyl or cyclopropylmethyl group.

In another embodiment, $R_b$ is hydrogen, or an optionally substituted alkyl.

In another embodiment, $R_b$ is $C_{1-10}$ alkyl, heteroaryl, or aryl, all optionally substituted.

The moiety -Z'-$(CR_{10}R_{20})$s-Z' forms a cyclic ring, such as a dioxalane ring.

Suitably Z' is independently selected at each occurrence from oxygen, or sulfur.

Suitably, s is independently selected at each occurrence from 0 or an integer having a value of 1, 2, or 3.

For each of the integer variables where appropriate, e.g. n, n', m, q', s, t, or v', etc. they are independently chosen at each occurrence.

Suitably, $R_5$ is independently selected at each occurrence from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2$ $R_5$ being $SO_2H$ and $S(O)R_5$ being SOH.

Suitably, $R_j$ is hydrogen, $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties, excluding hydrogen, may be optionally substituted.

Suitably, $R_j$ is $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety.

Suitably, $R_8$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted independently at each occurrence, 1 to 4 times, by halogen; halosubstituted $C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$alkyl; $C_{1-4}$alkoxy; halosubstituted $C_{1-4}$ alkoxy; $S(O)mC_{1-4}$ alkyl; —C(O), $C(O)C_{1-4}$ alkyl; $NR_{21}R_{31'}$; or an aryl or aryl $C_{1-4}$ alkyl, and wherein these aryl containing moieties may also be substituted one to two times independently at each occurrence, by halogen, hydroxy, hydroxy substituted alkyl, $C_{1-4}$ alkoxy, $S(O)_mC_{1-4}$alkyl, amino, mono & di-substituted $C_{1-4}$ alkylamino, $C_{1-4}$ alkyl, or $CF_3$.

Suitably, $R_{15}$ and $R_{25}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, or aryl-$C_{1-4}$ alkyl, heteroaryl or heteroaryl $C_{1-4}$ alkyl moiety, and wherein these moieties, excluding hydrogen may be optionally substituted; or $R_{15}$ and $R_{25}$ together with the nitrogen which they are attached form an optionally substituted heterocyclic ring of 4 to 7 members, which ring optionally contains an additional heteroatom selected from oxygen, sulfur or $NR_9$; and wherein these moieties are optionally substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; $SR_5$, $S(O)R_5$, $S(O)_2R_5$; $C(O)R_j$; $C(O)OR_j$; $C(O)NR_4R_{14'}$; $NR_4C(O)C_{1-10}$alkyl; $NR_4C(O)$aryl; $NR_4R_{14'}$; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl$C_{1-4}$ alkyl, heteroaryl, or hetero$C_{1-4}$ alkyl, heterocyclic and heterocyclic$C_{1-4}$ alkyl and wherein these aryl, heterocyclic and heteroaryl containing moieties may also be substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & disubstituted $C_{1-4}$ alkyl amino, $C_{1-4}$ alkyl, or $CF_3$.

Suitably, $R_4$ and $R_{14}$ are each independently selected at each occurrence from hydrogen, $C_{1-10}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or heteroaryl $C_{1-4}$ alkyl; or the $R_4$ and $R_{14}$ together with the nitrogen which they are attached form an unsubstituted or substituted heterocyclic ring of 4 to 7 members, which ring optionally contains an additional heteroatom selected from oxygen, sulfur or nitrogen; and wherein the $C_{1-10}$ alkyl, $C_{3-7}$cycloalkyl, $C_{3-7}$cycloalkyl$C_{1-4}$ alkyl, aryl, aryl-$C_{1-4}$ alkyl, heteroaryl and heteroaryl $C_{1-4}$ alkyl moieties, and the $R_4$ and $R_{14}$ cyclized ring are optionally substituted, 1 to 4 times, independently at each occurrence, by halogen; hydroxy; hydroxy substituted $C_{1-10}$alkyl; $C_{1-10}$ alkoxy; halosubstituted $C_{1-10}$ alkoxy; $C_{1-10}$ alkyl; halosubstituted $C_{1-10}$ alkyl; $SR_5$; $S(O)R_5$; $S(O)_2R_5$;

C(O)R$_j$; C(O)OR$_j$; C(O)NR$_4$R$_{14}$; (CR$_{10}$R$_{20}$)$_n$N(R$_{10'}$)C(Z)OR$_7$; (CR$_{10}$R$_{20}$)$_n$N(R$_{10'}$)C(Z)NR$_d$R$_d$; NR$_4$C(O)C$_{1-10}$alkyl; NR$_4$C(O)aryl; NR$_4$R$_{14'}$; cyano; nitro; C$_{3-7}$cycloalkyl; C$_{3-7}$cycloalkyl C$_{1-10}$ alkyl; C$_{1-10}$ alkyl substituted one or more times by an optionally substituted aryl; an unsubstituted or substituted aryl, or arylC$_{1-4}$ alkyl; an unsubstituted or substituted heteroaryl, or heteroaryl C$_{1-4}$ alkyl; an unsubstituted or substituted heterocyclic, or heterocyclic C$_{1-4}$ alkyl, and wherein these aryl, heterocyclic and heteroaryl containing moieties are substituted one to two times independently at each occurrence by halogen; C$_{1-4}$ alkyl, hydroxy; hydroxy substituted C$_{1-4}$ alkyl; C$_{1-4}$ alkoxy; S(O)$_m$alkyl; amino, mono & di-substituted C$_{1-4}$ alkyl amino, or CF$_3$.

Suitably, when R$_4$ and R$_{14}$ together with the nitrogen cyclize to form an optionally substituted ring, such as described above, such rings include, but are not limited to pyrrolidine, piperidine, piperazine, diazepine, azepine, morpholine, and thiomorpholine (including oxidizing the sulfur).

Suitably, R$_{4'}$ and R$_{14'}$ are each independently selected at each occurrence from hydrogen or C$_{1-4}$ alkyl, or R$_{4'}$ and R$_{14'}$ can cyclize together with the nitrogen to which they are attached to form an optionally substituted 5 to 7 membered ring which optionally contains an additional heteroatom from oxygen, sulfur or NR$_{9'}$. Suitably, when R$_{4'}$ and R$_{14'}$ cyclize to form an optionally substituted ring, such rings include, but are not limited to pyrrolidine, piperidine, piperazine, morpholine, and thiomorpholine (including oxidizing the sulfur).

Suitably, R$_{4''}$ and R$_{14''}$ are each independently selected from hydrogen or C$_{1-10}$ alkyl, or R$_{4''}$ and R$_{14'}$ can cyclize together with the nitrogen to which they are attached to form an optionally substituted 5 to 7 membered ring which optionally contains an additional heteroatom selected from oxygen, sulfur or NR$_{9''}$. Suitably, when R$_{4'''}$ and R$_{14}$ cyclize to form an optionally substituted ring, such rings include, but are not limited to pyrrolidine, piperidine, piperazine, diazepine, azepine, morpholine, and thiomorpholine (including oxidizing the sulfur).

Suitably, R$_6$ is independently selected from hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or a heteroarylC$_{1-10}$ alkyl moiety, and wherein these moieties, excluding hydrogen may be optionally substituted independently, one or more times, suitably 1 to 2 times, by halogen; hydroxy; hydroxy substituted C$_{1-10}$alkyl; C$_{1-10}$ alkoxy; halosubstituted C$_{1-10}$ alkoxy; S(O)m alkyl; C(O); NR$_4$R$_{14'}$; C$_{1-10}$ alkyl; C$_{3-7}$cycloalkyl; C$_{3-7}$cycloalkyl C$_{1-10}$ alkyl; halosubstituted C$_{1-10}$ alkyl; an unsubstituted aryl or arylalkyl, or an aryl or arylalkyl substituted one or two times by halogen, hydroxy, hydroxy substituted alkyl, C$_{1-10}$ alkoxy, S(O)$_m$alkyl, amino, mono & di-substituted C$_{1-4}$ alkyl amino, C$_{1-4}$ alkyl, or CF$_3$.

Suitably, R$_9$ is hydrogen, C(Z)R$_6$, optionally substituted C$_{1-10}$ alkyl, optionally substituted aryl or optionally substituted aryl-C$_{1-4}$ alkyl. The alkyl, aryl and arylalkyl moieties may be optionally substituted 1 or 2 times, independently by halogen; hydroxy; hydroxy substituted C$_{1-10}$alkyl; C$_{1-10}$ alkoxy; halosubstituted C$_{1-10}$ alkoxy; S(O)m alkyl; —C(O); NR$_4$R$_{14'}$; C$_{1-10}$ alkyl; C$_{3-7}$cycloalkyl; C$_{3-7}$cycloalkyl C$_{1-10}$ alkyl; halosubstituted C$_{1-10}$ alkyl; an aryl or aryl C$_{1-4}$ alkyl, and wherein these aryl containing moieties may also be substituted one or two times independently by halogen, hydroxy, hydroxy substituted alkyl, C$_{1-10}$ alkoxy, S(O)$_m$C$_{1-4}$ alkyl, amino, mono & di-substituted C$_{1-4}$ alkyl amino, C$_{1-4}$ alkyl, or CF$_3$.

Suitably, R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic, or heterocyclylC$_{1-10}$ alkyl moiety, which moieties may be optionally substituted 1 to 4 times, independently at each occurrence by hydrogen, halogen, nitro, C$_{1-10}$ alkyl, halo-substituted C$_{1-10}$ alkyl, C$_{2-10}$ alkenyl, C$_{2-10}$alkynyl, C$_{3-7}$cycloalkyl, C$_{3-7}$cycloalkylC$_{1-10}$ alkyl, C$_{5-7}$cycloalkenyl, C$_{5-7}$cycloalkenylC$_{1-10}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$N(R$_{10'}$)S(O)$_2$R$_7$, (CR$_{10}$R$_{20}$)$_n$NR$_{16}$R$_{26}$, (CR$_{10}$R$_{20}$)$_n$CN, (CR$_{10}$R$_{20}$)$_n$S(O)$_2$NR$_{16}$R$_{26}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_{16}$R$_{26}$, (CR$_{10}$R$_{20}$)$_n$N(R$_{10'}$)C(Z)R$_6$, (CR$_{10}$R$_{20}$)$_n$N(R$_{10'}$)C(=N(R$_{10'}$))NR$_{16}$R$_{26}$, (CR$_{10}$R$_{20}$)$_n$OC(Z)NR$_{16}$R$_{26}$, (CR$_{10}$R$_{20}$)$_n$N(R$_{10'}$)C(Z)NR$_{16}$R$_{26}$, or (CR$_{10}$R$_{20}$)$_n$N(R$_{10'}$)C(Z)OR$_7$.

In one embodiment, the R$_3$ moieties are optionally substituted 1 to 4 times, independently at each occurrence by halogen, nitro, C$_{1-4}$ alkyl, halo-substituted C$_{1-4}$ alkyl, C$_{2-4}$ alkenyl, C$_{2-4}$alkynyl, C$_{3-6}$cycloalkyl, C$_{3-6}$cycloalkylC$_{1-4}$ alkyl, C$_{5-6}$cycloalkenyl, C$_{5-6}$cycloalkenylC$_{1-4}$ alkyl, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NHS(O)$_2$R$_7$, (CR$_{10}$R$_{20}$)$_n$S(O)$_2$NR$_{16}$R$_{26}$, (CR$_{10}$R$_{20}$)$_n$NR$_{16}$R$_{26}$, (CR$_{10}$OR$_{20}$)$_n$CN, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$N(R$_{10}$')C(Z)R$_6$, or (CR$_{10}$R$_{20}$)$_n$C(Z)NR$_{16}$R$_{26}$.

In one embodiment the R$_3$ moieties are optionally substituted independently, one or more times, suitably 1 to 4 times, independently at each occurrence by halogen, C$_{1-10}$alkyl, (CR$_{10}$R$_{20}$)$_n$OR$_6$, cyano, nitro, (CR$_{10}$R$_{20}$)$_n$NR$_{16}$R$_{26}$, or halo-substituted C$_{1-10}$alkyl. Further to this embodiment, R$_3$ is a phenyl ring, optionally substituted independently, one or more times, suitably 1 to 4 times, independently at each occurrence by halogen, C$_{1-10}$ alkyl, hydroxy, C$_{1-10}$ alkoxy, cyano, nitro, amino, or halosubstituted C$_{1-10}$ alkyl. In another embodiment, the R$_3$ substituents are selected independently from halogen, such as fluorine, chlorine, bromine or iodine, or C$_{1-10}$ alkyl, such as methyl.

In one embodiment the R$_3$ moieties are an optionally substituted C$_{1-10}$ alkyl, optionally substituted C$_{3-7}$cycloalkyl, optionally substituted C$_{3-7}$cycloalkylalkyl, or optionally substituted aryl. In another embodiment, the R$_3$ moiety is an optionally substituted C$_{1-0}$ alkyl, or an optionally substituted aryl. In another embodiment, R$_3$ is an optionally substituted phenyl.

Suitably, in one embodiment when R$_3$ is an aryl moiety, it is an optionally substituted phenyl ring. The phenyl is optionally substituted one or more times, independently at each occurrence, suitably 1 to 4 times by halogen, C$_{1-4}$ alkyl, or halo-substituted-C$_{1-4}$ alkyl. The phenyl ring may be substituted in the 2, 4, or 6-position, or di-substituted in the 2,4-position or 2,6-position, such as 2-fluoro, 4-fluoro, 2,4-difluoro, 2,6-difluoro, or 2-methyl-4-fluoro; or tri-substituted in the 2,4,6-position, such as 2,4,6-trifluoro.

In one embodiment of the invention, the R$_3$ optional substituents are independently selected from halogen, alkyl, hydroxy, alkoxy, cyano, nitro, amino, or halosubstituted alkyl. In another embodiment, the optional substituents are independently selected from halogen, or alkyl.

Suitably, R$_7$ is C$_{1-6}$alkyl, aryl, arylC$_{1-6}$alkyl, heterocyclic, heterocyclylC$_{1-6}$ alkyl, heteroaryl, or heteroarylC$_{1-6}$alkyl; and wherein each of these moieties may be optionally substituted one or two times independently, by halogen; hydroxy; hydroxy substituted C$_{1-10}$alkyl; C$_{1-10}$ alkoxy; halosubstituted C$_{1-10}$ alkoxy; S(O)m alkyl; C(O); NR$_4$R$_{14'}$; C$_{1-10}$ alkyl; C$_{3-7}$cycloalkyl; C$_{3-7}$cycloalkylC$_{1-10}$ alkyl; halosubstituted C$_{1-10}$ alkyl; an aryl or arylalkyl moiety, and wherein these aryl containing moieties may also be substituted one to two times by halogen, hydroxy, hydroxy substituted alkyl, C$_{1-10}$ alkoxy, S(O)$_m$alkyl, amino, mono & di-substituted C$_{1-4}$ alkyl amino, C$_{1-4}$ alkyl, or CF$_3$.

Suitably, $R_{16}$ and $R_{26}$ are each independently selected from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_{9''}$.

Suitably, n is 0 or an integer having a value of 1 to 10, and is independently selected at each occurrence.

Suitably, X is $R_2$, $OR_{2'}$, $S(O)_mR_{2'}$, $(CH_2)_nN(R_{11})S(O)mR_{2'}$, $(CH_2)_nN(R_{11})C(O)R_{2'}$, $(CH_2)_nNR_4R_{14}$, $(CH_2)_nN(R_{2'})(R_{2''})$, or $N(R_{10'})R_hNH\text{—}C(\text{=}N\text{—}CN)NR_qR_{q'}$.

Suitably, n' is independently selected at each occurrence from 0 or an integer having a value of 1 to 10;

Suitably, $R_h$ is selected from an optionally substituted $C_{1-10}$ alkyl, —$CH_2CH_2$—O—$CH_2$—$CH_2$—, —$CH_2$—O—$CH_2$—, —$CH_2$—$C(O)N(R_{10'})CH_2$—$CH_2$—, —$CH_2$—N$(R_{10'})C(O)CH_2$—, —$CH_2$—CH$(OR_{10'})$—$CH_2$—, —$CH_2$—C(O)O—$CH_2$—$CH_2$—, or —$CH_2$—$CH_2$—O—C(O)$CH_2$—.

Suitably, $R_q$ and $R_{q'}$ are independently selected from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties are optionally substituted, or $R_q$ and $R_{q'}$ together with the nitrogen to which they are attached form a 5 to 7 membered optionally substituted ring, which ring may contain an additional heteroatom selected from oxygen, nitrogen or sulphur.

Suitably, $X_1$ is $N(R_{10'})$, O, $S(O)_m$, or $CR_{10}R_{20}$. In one embodiment of the invention, $X_1$ is $N(R_{10'})$, or O.

Suitably, $R_2$ is independently selected from hydrogen, optionally substituted $C_{1-10}$ alkyl, optionally substituted $C_{3-7}$ cycloalkyl, optionally substituted $C_{3-7}$cycloalkylalkyl, optionally substituted aryl, optionally substituted aryl$C_{1-10}$alkyl, optionally substituted heteroaryl, optionally substituted heteroaryl$C_{1-10}$ alkyl, optionally substituted heterocyclic, optionally substituted heterocyclyl$C_{1-10}$alkyl moiety; or $R_2$ is the moiety $(CR_{10}R_{20})_qX_1(CR_{10}R_{20})_qC(A_1)(A_2)(A_3)$, or $(CR_{10}R_{20})_qC(A_1)(A_2)(A_3)$.

Suitably q' is 0, or an integer having a value of 1 to 6.

Suitably q is 0, or an integer having a value of 1 to 10.

The $R_2$ moieties, excluding hydrogen, may be optionally substituted one or more times, preferably 1 to 4 times, independently at each occurrence by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, —C(O), cyano, nitro, aryl, aryl $C_{1-10}$ alkyl, heterocyclic, heterocyclic $C_{1-10}$ alkyl, heteroaryl, heteroaryl $C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_nNR_eR_{e'}C_{1-4}$alkyl $NR_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(\text{=}N(R_{10'}))NR_eR_{e'}$, $(CR_{10}R_{20})_nC(\text{=}NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$.

Suitably, $R_e$ and $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, which moieties may be optionally substituted; or $R_e$ and $R_{e'}$ together with the nitrogen which they are attached form an optionally substituted heterocyclic ring of 4 to 7 members, which ring optionally contains an additional heteroatom selected from oxygen, sulfur or nitrogen; and wherein each of these moieties, including the cyclized ring and excluding hydrogen, may be substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; $C_{1-10}$ alkyl; halosubstituted $C_{1-4}$ alkyl; $S(O)mR_{f'}$; $C(O)R_j$; $C(O)OR_j$; $(CR_{10}R_{20})_nN(R_{10'})C(Z)OR_7$; $(CR_{10}R_{20})_nN(R_{10'})C(Z)NR_dR_{d'}$; $C(O)NR_4R_{14'}$; $NR_4C(O)C_{1-10}$alkyl; $NR_4C(O)$aryl; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl$C_{1-4}$alkyl, heterocyclic, heterocyclic $C_{1-4}$ alkyl, heteroaryl, or hetero $C_{1-4}$ alkyl, and wherein these aryl, heterocyclic or heteroaryl containing moieties may be optionally substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$.

Suitably, $R_{f'}$ is independently selected at each occurrence from hydrogen, $C_{1-10}$alkyl, aryl, aryl $C_{1-10}$alkyl, heteroaryl, heteroaryl $C_{1-10}$alkyl, heterocyclic, heterocyclic $C_{1-10}$alkyl or $NR_4R_{14'}$, and wherein these moieties, excluding hydrogen, and $NR_4R_{14'}$, may be optionally substituted.

In one embodiment of the present invention X is $R_2$, $OR_{2'}$, $(CH_2)_nNR_4R_{14}$, or $(CH_2)_nN(R_{2'})(R_{2''})$. In another embodiment of the present invention, X is $R_2$, and $R_2$ is $(CR_{10}R_{20})_{q'}X_1(CR_{10}R_{20})_qC(A_1)(A_2)(A_3)$, or $(CR_{10}R_{20})_qC(A_1)(A_2)(A_3)$.

When X is $R_2$ and $R_2$ is an optionally substituted heterocyclic or heterocyclic alkyl, the heterocyclic containing moiety is suitably selected from tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

In one embodiment, $R_2$ is an optionally substituted piperidinyl or piperazinyl ring.

In another embodiment, when $R_2$ is an optionally substituted heterocyclic or heterocyclic alkyl ring the ring is substituted one or mores times independently by an optionally substituted heterocyclic, heterocyclic alkyl, aryl, arylalkyl, alkyl, $(CR_{10}R_{20})_nNR_eR_{e'}$, or $(CR_{10}R_{20})_nN(R_{10'})C(Z)OR_7$. The second heterocyclic ring is suitably selected from an optionally substituted tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, diazepine, morpholino or thiomorpholino (including oxidized versions of the sulfur moiety). Suitably, the second heterocyclic ring is selected from morpholino, piperidine, or pyrrolidinyl.

In one embodiment, $R_2$ is a 4-amino-1-piperidinyl, 1,1-dimethylethyl)oxy]-carbonyl}amino)-1-piperidinyl, 4-methyl-1-piperazinyl, 4-ethyl-1-piperazinyl, 4-propyl-1-piperazinyl, 4-butyl-1-piperazinyl, 4-(methylamino)-1-piperidinyl, 1,1-dimethylethyl-4-piperidinyl}methylcarbamate, 4-phenyl-1-piperazinyl, 1,4'-bipiperidin-1'-yl, 4-(1-pyrrolidinyl)-1-piperidinyl, 4-methyl-1,4'-bipiperidin-1'-yl, 4-(4-morpholinyl)-1-piperidinyl, 4-(diphenylmethyl)-1-piperazinyl, or 4-methylhexahydro-1H-1,4-diazepin-1-yl.

Suitably, $R_{2'}$ is independently selected at each occurrence from hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted 1 to 4 times, independently, at each occurrence, by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$cycloalkenyl, $C_{5-7}$ cycloalkenyl$C_{1-10}$ alkyl, halogen, —C(O), cyano, nitro, aryl, aryl $C_{1-10}$ alkyl, heteroaryl, heteroaryl$C_{1-10}$ alkyl, heterocyclic, heterocyclyl$C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}OR_{20})_nNR_eR_{e'}$, $(CR_{10}R_{20})_nNR_eR_{e'}C_{1-4}alkylNR_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$.

In one embodiment, when X is $(CH_2)_nN(R_{2'})(R_{2''})$, one of $R_{2'}$, or $R_{2''}$ is hydrogen, or methyl.

In one embodiment, when $R_{2'}$ is an optionally substituted heterocyclic or heterocyclyl$C_{1-10}$ alkyl the heterocyclic containing moiety is substituted one or more time independently by $C_{1-10}$ alkyl, aryl, heteocyclic, $(CR_{10}R_{20})_nNR_eR_{e'}$, $(CR_{10}R_{20})_nN(R_{10'})C(Z)OR_7$, or $(CR_{10}R_{20})_nC(Z)OR_6$. More specifically, methyl, ethyl, NHC(O)O—CCH$_3$, N(CH$_3$)C(O)O—CCH$_3$, amino, methylamino, dimethylamino, phenyl, piperidine, pyrrolidine, 1-ethylpropyl, 4-methyl-1,4'-bipiperidin-1'-yl, 1,4'-bipiperidin-1'-yl, morpholino.

In one embodiment, when X is $(CH_2)_nN(R_{2'})(R_{2''})$, $R_{2'}$ is an optionally substituted $C_{1-10}$ alkyl, cycloalkyl, heterocyclic, heterocyclyl $C_{1-10}$ alkyl, heteroarylalkyl. Suitably, when $R_{2'}$ is an optionally substituted cycloalkyl it is an cyclohexyl ring. In one embodiment the cyclohexyl ring is optionally substituted one or more times by $(CR_{10}R_{20})_nNR_eR_{e'}$.

Suitably, when $R_{2'}$ is an optionally substituted heterocyclic, or a heterocyclyl$C_{1-10}$ alkyl, the ring is selected from tetrahydropyrrole, tetrahydropyran, tetrahydrofuran, tetrahydrothiophene (including oxidized versions of the sulfur moiety), aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, diazepine, hexahydro-1-H-azepine, morpholino or thiomorpholino (including oxidized versions of the sulfur moiety). Preferably, the ring is a piperidine, piperazine, pyrrolidinyl, 2-oxo-1-pyrrolidinyl, morpholino, hexahydro-1-H-azepine ring. In one embodiment, the rings are substituted one or more times, suitably 1 to 4 times, independently by $C_{1-10}$ alkyl, aryl, arylalkyl, $(CR_{10}R_{20})_nNR_eR_{e'}$, or $(CR_{10}R_{20})_nN(R_{10'})C(Z)OR_7$.

In one embodiment, $(CH_2)_nN(R_{2'})(R_{2''})$ is 1-(phenylmethyl)-4-piperidinamine, 2-[4-(phenylmethyl)-1-piperazinyl]ethylamine, 2-(1-piperidinyl)ethylamine, 2-(1-methyl-2-pyrrolidinyl)ethylamine, 1-[(phenylmethyl)-3-pyrrolidinyl]amine, 3-[(1-pyrrolidinyl)propyl]amine, 3-[(hexahydro-1H-azepin-1-yl)propyl]amine, (1-methyl-4-piperidinyl)amine, 3-[(4-morpholinyl)propyl]amine, 3-[(2-oxo-1-pyrrolidinyl)propyl]-amine, 2-[(4-morpholinyl)ethyl]amine, 2-[(1-pyrrolidinyl)ethyl]-amine, or [(1-ethyl-2-pyrrolidinyl)methyl]amino.

In one embodiment when X is $(CH_2)_nN(R_{2'})(R_{2''})$, and $R_{2'}$ is an optionally substituted $C_{1-10}$ alkyl, the alkyl is substituted one or more times independently by $(CR_{10}R_{20})_nNR_eR_{e'}$, or $(CR_{10}R_{20})_nNR_eR_{e'}C_{1-4}alkylNR_eR_{e'}$. In one embodiement $R_e$ and $R_{e'}$ are independently an optionally substituted $C_{1-4}$ alkyl, such as methyl, ethyl, isopropyl, n-butyl, or t-butyl. Preferably, $(CH_2)_nN(R_{2'})(R_{2''})$ is 3-(dimethylamino)propyl(methyl)amine, 3-(diethylamino)propylamine, propylamine, (2,2-dimethylpropyl)amine, (2-hydroxypropyl)amino, 2-(dimethylamino)ethylamine, 2-(dimethylamino)ethyl(methyl)amine, 3-(dimethylamino)propylamine, 2-(dimethylamino)ethyl(methyl)amine, 3-(diethylamino)propylamine, 2-(methylamino)ethylamine, [(1-methylethyl)amino]ethylamine, 3-(diethylamino)propylamine, 3-(dibutylamino)propylamine, 3-[(1-methylethyl)amino]propylamine, 3-(1,1-dimethylethyl)aminopropylamine, 3-(dimethylamino)-2,2-dimethylpropylamine, 4-(diethylamino)-1-methylbutylamine, or 3-[[3-(dimethylamino)propyl](methyl)amino]propyl(methyl)amine.

Suitably $R_{2''}$ is selected from hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally substituted 1 to 4 times, independently at each occurrence, by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, —C(O), cyano, nitro, aryl, aryl $C_{1-10}$ alkyl, heteroaryl, heteroaryl$C_{1-10}$ alkyl, heterocyclic, heterocyclyl$C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_nNR_eR_{e'}C_{1-4}alkyl$ $NR_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$; or wherein $R_{2''}$ is the moiety $(CR_{10}R_{20})_tX_1(CR_{10}R_{20})_qC(A_1)(A_2)(A_3)$;

Suitably, t is an integer having a value of 2 to 6.

Suitably, q is 0 or an integer having a value of 1 to 10.

Suitably, $A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl.

Suitably, $A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl.

Suitably, $A_3$ is hydrogen or is an optionally substituted $C_{1-10}$ alkyl.

The $A_1$, $A_2$, and $A_3$ $C_{1-10}$ alkyl moieties may optionally substituted one or more times independently at each occurrence, preferably from 1 to 4 times, with halogen, such as chlorine, fluorine, bromine, or iodine; halo-substituted $C_{1-10}$alkyl, such as $CF_3$, or $CHF_2CF_3$; $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl$C_{1-10}$alkyl, $(CR_{10}R_{20})_nOR_6$, $(CR_{10}OR_{20})_nSH$, $(CR_{10}OR_{20})_nS(O)_mR_7$, $(CR_{10}R_{20})_nN(R_{10'})S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nN(R_{10'})C(Z)R_6$, $(CR_{10}R_{20})_nN(R_{10'})C(=N(R_{10'}))NR_4R_{14}$, $(CR_{10}R_{20})_nOC(Z)NR_4R_{14}$, $(CR_{10}R_{20})_nN(R_{10'})C(Z)NR_4R_{14}$, or $(CR_{10}R_{20})_nN(R_{10'})C(Z)OR_7$.

In another embodiment of the present invention, X is $R_2$, and $R_2$ is $(CR_{10}R_{20})_qX_1(CR_{10}R_{20})_qC(A_1)(A_2)(A_3)$, or $(CR_{10}R_{20})_{q'}C(A_1)(A_2)(A_3)$. In a further embodiment, q' is 0.

In another embodiment when $R_2$ is the moiety $(CR_{10}R_{20})_{q'}X_1(CR_{10}R_{20})_qC(A_1)(A_2)(A_3)$, q' is 0, $X_1$ is nitrogen, q is 0 or 1, $A_1$ is an optionally substituted heterocyclic or heterocyclic alkyl, and $A_2$ is an optionally substituted aryl. More specifically, $R_2$ is 2-phenyl-2-(1-pyrrolidinyl)ethyl]amino, or 1-phenyl-2-(1-pyrrolidinyl)ethyl]amino. In another embodiment, $A_1$ is an optionally substituted aryl or arylalkyl, and $A_2$ is an optionally substituted aryl or arylalkyl.

In one embodiment of the invention, one or more of the $A_1$, $A_2$ and $A_3$ moieties are substituted with $(CR_{10}R_{20})_nOR_6$. In another embodiment of the invention, the $R_6$ substituent Fin $(CR_{10}R_{20})_nOR_6$ is hydrogen.

In yet another embodiment of the present invention, X is $R_2$ and $R_2$ is $C(A_1)(A_2)(A_3)$, such as $CH(CH_2OH)_2$, or $C(CH_3)(CH_2OH)_2$; or $X_1(CR_{10}R_{20})qCH(CH_2OH)_2$, or $X_1(CR_{10}R_{20})qC(CH_3)(CH_2OH)_2$; and further wherein $X_1$ is oxygen or nitrogen.

In another embodiment X is $S(O)_mR_{2'}$, $(CH_2)_nNR_4R_{14}$, or $(CH_2)_nN(R_{2'})(R_{2'})$. In yet another embodiment, X is $(CH_2)_nNR_4R_{14}$, or $(CH_2)_nN(R_{2'})(R_{2'})$.

Suitably, when X is $(CH_2)_nNR_4R_{14}$, and $R_4$ and $R_{14}$ are $C_{1-10}$ alkyl, aryl, aryl-$C_{1-4}$ alkyl, heterocyclic, heterocyclic $C_{1-4}$ alkyl, heteroaryl or heteroaryl $C_{1-4}$ alkyl, the $C_{1-4}$ alkyl may be substituted one or more times, independently at each occurrence with $NR_{4'}R_{14'}$; halogen, hydroxy, alkoxy, $C(O)NR_{4'}R_{14'}$; or $NR_{4'}C(O)C_{1-10}$alkyl. Preferably, the $C_{1-4}$ alkyl is substituted with $NR_{4'}R_{14'}$.

In one embodiment at least one of $R_4$ and $R_{14}$ may be hydrogen when $R_4$ and $R_{14}$ are not cyclized. In another embodiment neither $R_4$ nor $R_{14}$ is hydrogen.

In one embodiment when X is $(CH_2)_nNR_4R_{14}$, one of $R_4$ and $R_{14}$ are hydrogen, and the other is an optionally substituted heteroaryl $C_{1-4}$ alkyl. Suitably, the optionally substituted heteroaryl alkyl is an imidazolyl alkyl, such as a 1H-imidazol-2-yl-methyl group.

In one embodiment when X is $(CH_2)_nNR_4R_{14}$ and one of $R_4$ and $R_{14}$ is a heteroaryl $C_{1-4}$ alkyl moiety, then the heteroaryl ring is selected from thienyl, pyrrolyl, oxazolyl, thiazolyl, isoxazolyl, isothiazolyl, imidazolyl, pyrazolyl, triazolyl, pyridazinyl, pyrimidinyl, pyrazinyl, benzoxazolyl, benzimidazolyl, and benzothiazolyl. Suitably, the heteroaryl $C_{1-4}$ alkyl is selected from pyrrolyl, oxazolyl, thiazolyl, isoxazolyl, imidazolyl, benzoxazolyl, benzimidazolyl, and benzothiazolyl.

In another embodiment when X is $(CH_2)_nNR_4R_{14}$ and one of $R_4$ and $R_{14}$ is a heterocyclic $C_{1-4}$ alkyl moiety, then the heterocyclic ring is selected from tetrahydropyrrole, tetrahydropyran, tetrahydrofuran, pyrrolinyl, pyrrolidinyl, imidazolinyl, imidazolidinyl, indolinyl, pyrazolinyl, pyrazolidinyl, piperidinyl, piperazinyl, and morpholino. Suitably, the heterocyclic $C_{1-4}$ alkyl moiety is selected from pyrrolinyl, pyrrolidinyl, piperidinyl, piperazinyl, and morpholino.

In another embodiment when X is $(CH_2)_nNR_4R_{14}$ and $R_4$ and $R_{14}$ together with the nitrogen cyclize to form an optionally substituted ring, such as described above, such rings include, but are not limited to pyrrolidine, piperidine, piperazine, diazepine, and morpholine. In one embodiment when X is $(CH_2)_nNR_4R_{14}$, the $R_4$ and $R_{14}$ substituents cyclize to form a heterocyclic 5 or 6 membered ring, which ring is optionally substituted as defined herein. When the $R_4$ and $R_{14}$ substituents cyclize to form a 4 to 7 membered ring, the optional substitutents are suitably selected from an optionally substituted alkyl, an optionally substituted aryl, an optionally substituted heteroaryl, optionally substituted heterocyclic, $(CR_{10}R_{20})_nN(R_{10'})C(Z)OR_7$, $NR_{4'}R_{14'}$, or a $C_{1-10}$ alkyl substituted one or more times by an optionally substituted aryl. Such substitutents more specifically include phenyl, pyrrolidinyl, morpholino, piperazinyl, 4-methyl-1-piperazinyl, piperidinyl, 2-oxo-2,3-dihydro-1H-benzimidazol-1-yl, 5-chloro-2-oxo-2,3-dihydro-1H-benzimidazol-1-yl, diphenylmethyl, methyl, ethyl, propyl, butyl, amino, methylamino, and dimethylamino.

In one embodiment the X substituent is a 1,4'-bipiperin-1-yl ring which may be optionally substituted such as in 4-methyl-1,4'-bipiperin-1-yl; 4-piperidinylamino, 4-amino-1-piperidinyl, 2,2,6,6-tetramethyl-4-piperidinyl)amino, 4-methyl-1-piperazinyl, (4-morpholinyl)-1-piperidinyl, (4-methyl-1-piperazinyl)-1-piperidinyl, 4-ethyl-1-piperazinyl, (2-oxo-2,3-dihydro-1H-benzimidazol-1-yl)-1-piperidinyl, 5-chloro-(2-oxo-2,3-dihydro-1H-benzimidazol-1-yl)-1-piperidinyl, 4-(1-pyrrolidinyl)-1-piperidinyl, 4-(diphenylmethyl)-1-piperazinyl, 4-methylhexahydro-1H-1,4-diazepin-1-yl, 4-propyl-1-piperazinyl, or 4-butyl-1-piperazinyl.

In another embodiment, when X is $(CH_2)_nN(R_{2'})(R_{2''})$, and $R_{2'}$ is an optionally substituted $C_{1-10}$ alkyl moiety, and the alkyl is substituted by $(CR_{10}R_{20})_nNR_eR_{e'}$, and $R_e$ and $R_{e'}$ are hydrogen, or an optionally substituted $C_{1-10}$ alkyl. Suitably, the X moiety is 3-(diethylamino)propylamino, 3-(dimethylamino)propyl(methyl)amino, 3-(dimethylamino)propyl (methyl)amino, 2-(dimethylamino)ethylamino, 1-methylethyl)amino-propylamino, (1,1-dimethylethyl) aminopropylamino, (1-methylethyl)aminoethylamino, 2-(methylamino)ethylamino, 2-aminoethyl(methyl)amino, or a 2-(dimethylamino)ethyl(methyl)amino.

In another embodiment when X is $(CH_2)_nN(R_{2'})(R_{2''})$, and $R_{2'}$ moiety is an optionally substituted heteroaryl$C_{1-10}$ alkyl, the heteroaryl moiety is suitably an optionally substituted imidazole.

In one embodiment at least one of $R_4$ and $R_{14}$ may be hydrogen when $R_4$ and $R_{14}$ are not cyclized. In another embodiment neither $R_4$ and $R_{14}$ is hydrogen.

In one embodiment $R_3$ is a 2,6-difluoro phenyl, $R_1$ is a phenyl ring substituted by and $R_1$ is selected from $C(Z)N(R_{10'})(CR_{10}R_{20})_vR_b$, or $C(Z)O(CR_{10}R_{20})_vR_b$, or $N(R_{10'})C(Z)(CR_{10}R_{20})_vR_b$ and also substituted by $R_{1'}$ independently selected at each occurrence from hydrogen, fluorine, or methyl; g is 1 or 2. Preferably, $R_1$ is substituted by $C(Z)N(R_{10'})(CR_{10}R_{20})_vR_b$ and $R_{1'}$ independently selected at each occurrence from hydrogen, fluorine, or methyl. In another embodiment, the $R_b$ moiety is selected from thiazolyl, $C_{1-10}$ alkyl or an optionally substituted aryl. In another embodiment the $R_b$ moiety is propyl or 4-fluorophenyl.

In another embodiment, X is suitably selected from (1H-imidazol-2-ylmethyl)amino or 4-methyl-1,4'-bipiperidin-1'-yl, 2,2,6,6-tetramethyl-4-piperidinyl)amino, 4-amino-1-piperidinyl, 3-(diethylamino)propylamino, 3-(dimethylamino) propyl(methyl)amino, 3-(dimethylamino)propyl(methyl) amino, 2-(dimethylamino)ethylamino, 1-methylethyl) amino-propylamino, (1,1-dimethylethyl)aminopropylamino, (1-methylethyl)aminoethylamino, 2-(methylamino)ethylamino, 2-aminoethyl(methyl)amino, or 2-(dimethylamino) ethyl(methyl)amino.

In one embodiment, $R_3$ is a 2,6-difluoro phenyl, $R_1$ is phenyl, $R_{1'}$ is independently selected at each occurrence from hydrogen, fluorine, or methyl; g is 1 or 2; and the phenyl ring is also substituted in the 3- or 4-position by $C(Z)N(R_{10'})(CR_{10}R_{20})_vR_b$, $R_b$ moiety is $C_{1-10}$ alkyl or an optionally substituted aryl, preferably propyl or 4-fluorophenyl, X is $(CH_2)_nN(R_{2'})(R_{2''})$, and n is 0. In another embodiment, X is $(CH_2)_nN(R_{2'})(R_{2''})$, $R_{2''}$ is hydrogen, n is 0, and $R_{2'}$ is an alkyl substituted by $(CR_{10}R_{20})_nNR_eR_{e'}$. In a further embodiment, $R_e$ and $R_{e'}$ are independently selected from an optionally substituted $C_{1-4}$ alkyl, such as methyl, ethyl, isopropyl, n-butyl, or t-butyl, preferably ethyl.

In another embodiment of the present invention, for compounds of Formula (I) the X term may also be the B-Non-Arcyc moiety as disclosed in U.S. Pat. No. 6,809,199 whose disclosure is incorporated by reference herein.

As represented by the disclosure in U.S. Pat. No. 6,809,199, Non-Ar-Cyc is suitably selected from;

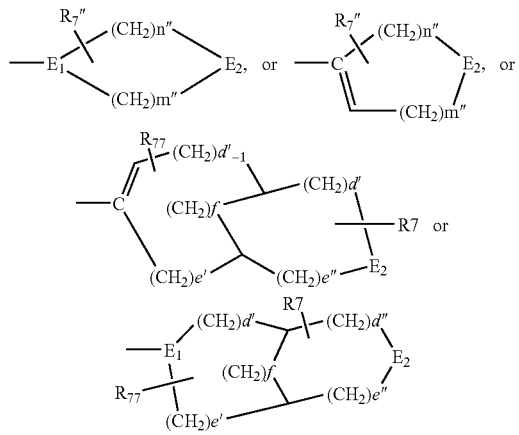

wherein
d is an integer having a value of 1, 2, 3, or 4;
d' is 0, or an integer having a value of 1, 2, or 3;
d" is 0, or an integer having a value of 1, 2, or 3;
e is 0, or is an integer having a value of 1, 2, 3, or 4;
e' is 0, or an integer having a value of 1, 2, or 3;
e" is 0, or an integer having a value of 1, 2, or 3;
f is 0, or is an integer having a value of 1, 2, or 3;
d+e is 2, 3, 4, 5, or 6;
d'+e"=d
e'+e"=m Suitably, $R_{7'}$, $R_{77}$ and $R_{77''}$ are each independently selected from hydrogen, $C_{1-6}$ alkyl-group, $C_{2-6}$ alkenyl-group, $C_{4-6}$ cycloalkyl-$C_{0-6}$ alkyl-group, N($C_{0-4}$ alkyl)($C_{0-4}$ alkyl)-$C_{1-4}$ alkyl-N($C_{0-4}$ alkyl)-group, —N($C_{0-4}$ alkyl)($C_{04}$ alkyl) group, $C_{1-3}$ alkyl-CO—$C_{0-4}$ alkyl-group, $C_{0-6}$ alkyl-O—C(O)—$C_{0-4}$ alkyl-group, $C_{0-6}$alkyl-C(O)—O—$C_{0-4}$alkyl-group, N($C_{0-4}$ alkyl)($C_{0-4}$ alkyl)-($C_{0-4}$ alkyl)C(O)($C_{0-4}$ alkyl)-group, phenyl-$C_{0-4}$ alkyl-group, pyridyl-$C_{0-4}$ alkyl-group, pyrimidinyl-$C_{0-4}$ alkyl-group, pyrazinyl-$C_{0-4}$ alkyl-group, thiophenyl-$C_{0-4}$ alkyl-group, pyrazolyl-$C_{0-4}$ alkyl-group, imidazolyl-$C_{0-4}$alkyl-group, triazolyl-$C_{0-4}$alkyl-group, azetidinyl-$C_{0-4}$ alkyl-group, pyrrolidinyl-$C_{0-4}$ alkyl-group, isoquinolinyl-$C_{0-4}$alkyl-group, indanyl-$C_{0-4}$ alkyl-group, benzothiazolyl-$C_{0-4}$ alkyl-group, any of the groups optionally substituted with 1-6 substituents, each substituent independently being —OH, —N($C_{0-4}$ alkyl)($C_{0-4}$alkyl), $C_{1-4}$alkyl, $C_{1-6}$ alkoxyl, $C_{1-6}$ alkyl-CO—$C_{0-4}$ alkyl-, pyrrolidinyl-$C_{0-4}$ alkyl-, or halogen; or $R_7$ together with a bond from an absent ring hydrogen is =O.

Suitably, B is —$C_{1-6}$alkyl-, —$C_{0-3}$ alkyl-O—$C_{0-3}$alkyl-, —$C_{0-3}$ alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)-CO-$_3$ alkyl-, —$C_{0-3}$ alkyl-NH—SO$_2$—$C_{0-3}$ alkyl-, —$C_{0-3}$ alkyl-, —$C_{0-3}$ alkyl-S—$C_{0-3}$ alkyl-, —$C_{0-3}$ alkyl-SO$_2$—$C_{0-3}$alkyl-, —$C_{0-3}$ alkyl-PH—$C_{0-3}$ alkyl-, $C_{0-3}$ alkyl —C(O)—$C_{0-3}$ alkyl, or a direct bond.

Suitably, $E_1$ is CH, N, or $CR_{66}$; or B and $E_1$ together form a double bond, i.e., —CH=C.

Suitably, $E_2$ is CH$_2$, CHR$_{77}$, C(OH)R$_{77}$ NH, NR$_{77}$, O, S, —S(O)—, or —S(O)$_2$—.

Suitably, $R_{66}$ is independently selected at each occurrence from halogen, $C_{0-4}$ alkyl, —C(O)—O($C_{0-4}$ alkyl), or —C(O)—N($C_{0-4}$ alkyl)-($C_{0-4}$ alkyl).

In an alternative embodiment of this invention, Non-Ary Cyc is:

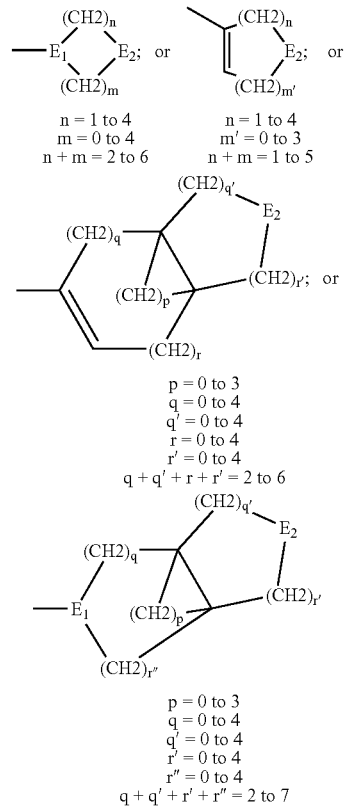

E1 = CH, CR6, N or B-E1 can equal double bond (C=C)

In another embodiment of the present invention, for compound of Formula (I) herein, the X term may also be the X moiety as disclosed in WO 2004/073628, published September 2004, Boehm et al., whose disclosure is incorporated by reference herein.

The term "halo" or "halogens" is used herein to mean the halogens, chloro, fluoro, bromo and iodo.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl, sec-butyl, tert-butyl or t-butyl and hexyl and the like.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl, 1,1-dimethylbut-2-enyl and the like.

As used herein, the term "alkoxy" refers to straight or branched chain alkoxy groups containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

As used herein, the term "cycloalkyl" refers to cyclic radicals, such as a non-aromatic hydrocarbon ring containing a specified number of carbon atoms. For example, $C_{3-7}$cycloalkyl means a non-aromatic ring containing at least three, and at most seven, ring carbon atoms. Representative examples of "cycloalkyl" as used herein include, but are not limited to, cyclopropyl, cyclobutyl, cyclopentyl, cyclohexyl and cycloheptyl and the like.

The term "cycloalkenyl" is used herein to mean cyclic radicals, such as a non-aromatic hydrocarbon ring containing a specified number of carbon atoms preferably of 5 to 7 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl, naphthyl, and indene.

The terms "heteroaryl ring", "heteroaryl moiety", and "heteroaryl" are used herein to mean a monocyclic five- to seven-membered unsaturated hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" shall also used herein to refer to fused aromatic rings comprising at least &&& contain five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

The terms "heterocyclic rings", "heterocyclic moieties", and "heterocyclyl" is used herein to mean a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The terms "heterocyclic rings", "heterocyclic moieties", and "heterocyclyl" shall also refer to fused rings, saturated or partially unsaturated, and wherein one of the rings may be aromatic, or heteroaromatic. Each of the fused rings may have from four to seven ring atoms. Examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

The term "arylalkyl" or "heteroarylalkyl" or "heterocyclicalkyl" is used herein to mean a $C_{1-4}$ alkyl (as defined above) attached to an aryl, heteroaryl or heterocyclic moiety (as also defined above) unless otherwise indicated.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean $C(O)C_{1-10}$ alkyl wherein the alkyl is as defined above.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halo-substituted $C_{1-10}$ alkoxy; S(O)m alkyl, such as methyl thio, methylsulfinyl or methyl sulfonyl; a ketone (—C(O)), or an aldehyde (—C(O)$R_{6'}$), such as $C(O)C_{1-10}$ alkyl or C(O)aryl, wherein $R_{6'}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl (and wherein the $R_{6'}$ moieties, excluding hydrogen, may themselves be optionally substituted 1 or 2 times, independently by halogen; hydroxy; hydroxy substituted alkyl; $C_{1-4}$ alkoxy; $S(O)_m C_{1-4}$ alkyl; amino, mono & di-substituted $C_{1-4}$ alkyl amino; $C_{1-4}$ alkyl, or $CF_3$); $C(O)OR_{6'}$; $NR_4 R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_{4'}R_{14'}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-4}$ alkoxy; $S(O)_m C_{1-4}$ alkyl; amino, mono & di-substituted $C_{1-4}$ alkyl amino; $C_{1-4}$ alkyl, or $CF_3$.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, $5^{th}$ Edition, Vol 1: Principles and Practice, which is incorporated herein by reference to the extent of teaching such derivatives.

In one embodiment of the present invention the pharmaceutically acceptable derivatives are salts, solvates, esters, carbamates and phosphate esters. In another embodiment pharmaceutically acceptable derivatives are salts, solvates and esters. In yet another embodiment, pharmaceutically acceptable derivatives are salts and esters, in particular salts.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Pharmaceutically acceptable salts of compounds of Formula (I) may suitably be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compound of the invention are within the scope of the invention.

Compounds of Formula (II) are represented by the structure:

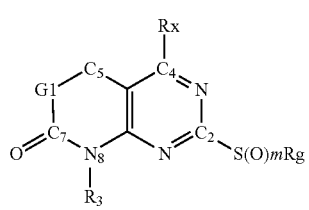

(II)

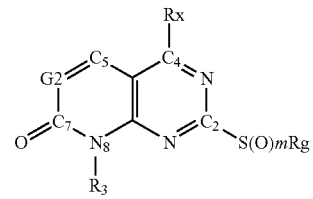

(IIa)

wherein
G1 is $CH_2$ or NH:
G2 is CH or nitrogen;
Rx is chloro, bromo, iodo, or $O—S(O)_2CF_3$;
$R_g$ is a $C_{1-10}$ alkyl;
m is 0, or an integer having a value of 1, or 2;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$alkyl, heteroaryl, heteroaryl$C_{1-10}$ alkyl, heterocyclic or a heterocyclyl$C_{1-10}$ alkyl moiety, and wherein each of these moieties may be optionally substituted.

The optional substituents for the $R_3$ moiety are as defined herein for compounds of Formula (I).

In one embodiment of the invention, Rx is chloro. In another embodiment, Rg is methyl. In a further embodiment, m is 0. In another embodiment m is 1, and $R_3$ is an optionally substituted phenyl (as defined in Formula (I)).

In another embodiment, m is 0, Rg is methyl, Rx is chloro and $R_3$ is an optionally substituted phenyl (as defined in Formula (I)).

Compounds of Formula (III) are represented by the structure:

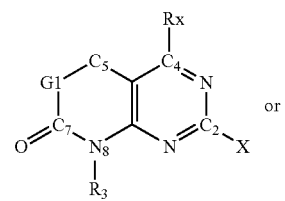

(III)

or

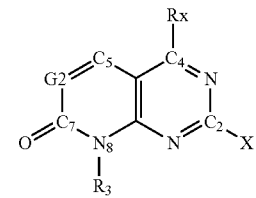

(IIIa)

wherein
G1 is $CH_2$ or NH:
G2 is CH or nitrogen;
Rx is chloro, bromo, iodo, or $O—S(O)_2CF_3$:
X is $R_2$, $OR_{2'}$, $S(O)_mR_{2'}$, $(CH_2)_nN(R_{11})S(O)_mR_{2'}$, $(CH_2)_nN(R_{11})C(O)R_{2'}$, $(CH_2)_nNR_4R_{14}$, or $(CH_2)_nN(R_{2'})(R_{2''})$, or $N(R_{10'})—R_h—NH—C(=N—CN)NRqRq'$;
$X_1$ is $N(R_{11})$, O, $S(O)_m$, or $CR_{10}R_{20}$;
$R_h$ is selected from an optionally substituted $C_{1-10}$ alkyl, $—CH_2—C(O)—CH_2—$, $—CH_2—O—CH_2—$, $—CH_2—C(O)N(R_{10'})CH_2—CH_2—$, $—CH_2—N(R_{10'})C(O)CH_2—$, —CH$_2$—CH(OR$_{10'}$)—CH$_2$, —CH$_2$—C(O)O—CH$_2$—CH$_2$—, or —CH$_2$—CH$_2$—O—C(O)CH$_2$—;

R$_q$ and R$_{q'}$ are independently selected at each occurrence from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety, wherein all of the moieties, excluding hydrogen, are optionally substituted, or R$_q$ and R$_{q'}$ together with the nitrogen to which they are attached form a 5 to 7 membered optionally substituted ring, which ring may contain an additional heteroatom selected from oxygen, nitrogen or sulfur;

R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted; or R$_2$ is the moiety (CR$_{10}$R$_{20}$)$_q$X$_1$(CR$_{10}$R$_{20}$)$_q$C(A$_1$)(A$_2$)(A$_3$), or C(A$_1$)(A$_2$)(A$_3$);

R$_{2'}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein each of these moieties, excluding hydrogen, may be optionally substituted;

R$_{2''}$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, and wherein these moieties, excluding hydrogen, may be optionally substituted; or wherein R$_{2''}$ is the moiety (CR$_{10}$R$_{20}$)$_q$X$_1$(CR$_{10}$R$_{20}$)$_q$C(A$_1$)(A$_2$)(A$_3$);

A$_1$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_2$ is an optionally substituted C$_{1-10}$ alkyl, heterocyclic, heterocyclic C$_{1-10}$ alkyl, heteroaryl, heteroaryl C$_{1-10}$ alkyl, aryl, or aryl C$_{1-10}$ alkyl;

A$_3$ is hydrogen or is an optionally substituted C$_{1-10}$ alkyl;

R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;

R$_4$ and R$_{14}$ are each independently selected from hydrogen, C$_{1-10}$ alkyl, C$_{3-7}$ cycloalkyl, C$_{3-7}$ cycloalkylC$_{1-4}$alkyl, aryl, aryl-C$_{1-4}$ alkyl, heterocyclic, heterocylic C$_{1-4}$ alkyl, heteroaryl or a heteroaryl C$_{1-4}$ alkyl moiety, and wherein each of these moieties, excluding hydrogen, may be optionally substituted; or the R$_4$ and R$_{14}$ together with the nitrogen which they are attached form an optionally substituted heterocyclic ring of 4 to 7 members, which ring optionally contains an additional heteroatom selected from oxygen, sulfur or nitrogen;

R$_{9'}$ is independently selected at each occurrence from hydrogen, or C$_{1-4}$ alkyl;

R$_{10}$ and R$_{20}$ are independently selected from hydrogen or C$_{1-4}$alkyl;

R$_{10'}$ is independently selected at each occurrence from hydrogen or C$_{1-4}$alkyl;

R$_{11}$ is independently selected from hydrogen or C$_{1-4}$alkyl;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6; or t is an integer having a value of 2 to 6.

Suitably, Rx is chloro, bromo, iodo, or O—S(O)$_2$CF$_3$. In an embodiment of the invention, Rx is chloro.

The X term moieties and their substituent groups, etc. are as defined herein for compounds of Formula (I).

Compounds of Formula (IV) are represented by the structure:

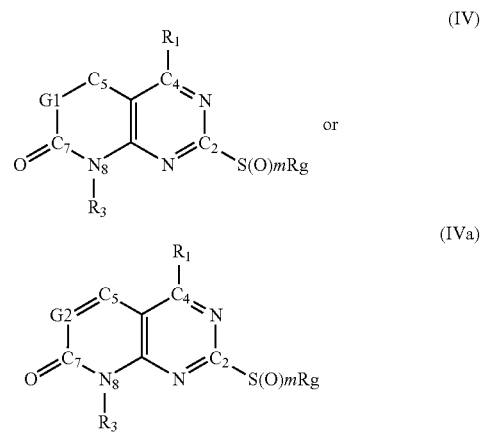

wherein

G1 is CH$_2$ or NH:

G2 is CH or nitrogen;

R$_1$ is an aryl, aryl C$_{2-10}$ alkyl, heteroaryl, heteroaryl C$_{2-10}$ alkyl; aryl C$_{2-10}$ alkenyl, arylC$_{2-10}$ alkynyl, heteroaryl C$_{2-10}$ alkenyl, heteroaryl C$_{2-10}$ alkynyl, C$_{2-10}$alkenyl, or C$_{2-10}$ alkynyl moiety, which moieties may be optionally substituted;

Rg is an optionally substituted C$_{1-10}$ alkyl;

m is 0 or an integer having the value of 1 or 2;

R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted.

Suitably R$_1$ and R$_3$ are substituted as defined herein for compounds of Formula (I). In one embodiment, R$_1$ is an optionally substituted aryl or heteroaryl ring, preferably an optionally substituted aryl.

In another embodiment Rg is methyl. In a further embodiment, m is 0 or 2.

Compounds of Formula (V) are represented by the formula:

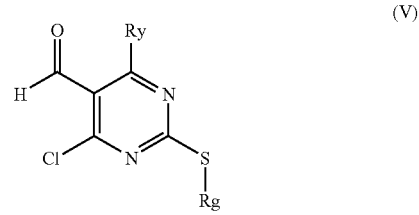

wherein

Ry is chloro, bromo, iodo, O—S(O)$_2$CF$_3$; and

Rg is a C$_{1-10}$ alkyl.

In one embodiment of the invention, Ry is bromo, iodo, or O—S(O)$_2$CF$_3$.

In another embodiment of the invention, Rg is methyl.

The general preparation of analogs around the pyrido[2,3-d]pyrimidin-7-one template is shown in the Schemes, Schemes 1 to 4 below. While a particular formula with particular substituent groups is shown herein, e.g. Rg as methyl, or Rx or LG2 as chloro, the synthesis is applicable to all formulas and all substituent groups as described herein.

The synthesis described herein, Schemes 1 to 4, start with a 4,6-Ry substituted-2-methylsulfanyl-pyrimidine-5-carboxaldehyde (1), such as described in Formula (V). Treatment of 1, Scheme 1, with an optionally substituted aniline in the presence of an olefin forming agent, such as bis(2,2,2-trifluoroethyl)-(methoxycarbonylmethyl)-phosphonate or an acylating agent, such as acetic acid anhydride affords the pyrido[2,3-d]pyrimidin-7-one, 2. Oxidation of 2 with a peracid, such as 3-chloroperoxybenzoic acid (m-CPBA) yields compound 3. This is followed by substitution of 3 in C2 position with a suitable X moiety as described in Formula (I) herein. In this scheme, substitution of the C2 position is demonstrated with serinol to furnish compound 4. Palladium (0) mediated Suzuki cross-coupling affords compound 5. Other cross coupling reactions known in the art may also be suitable for use herein.

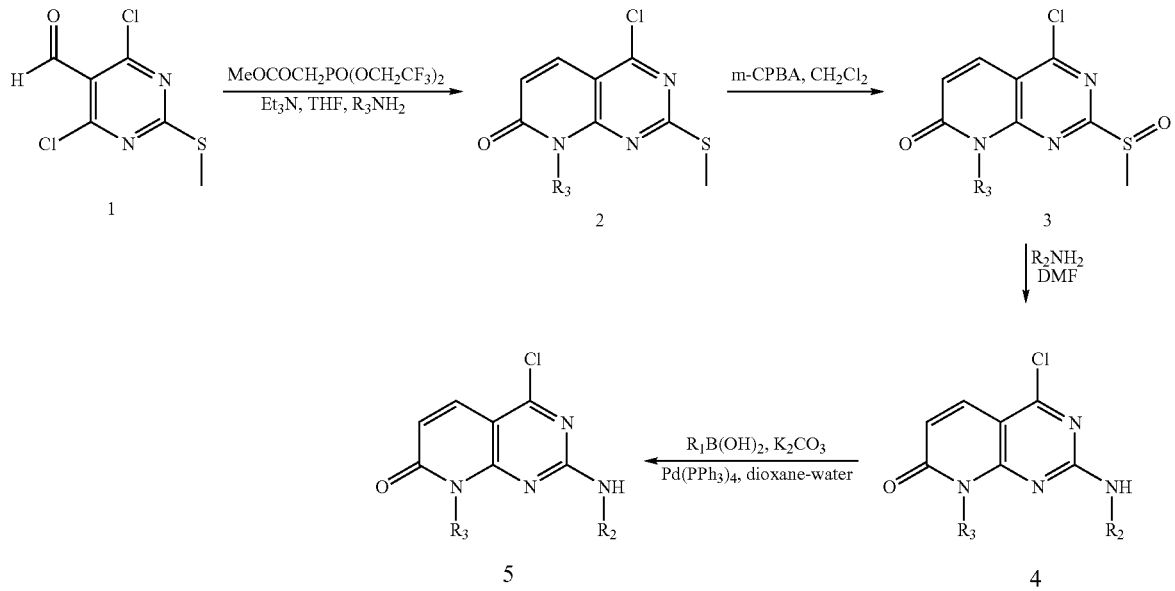

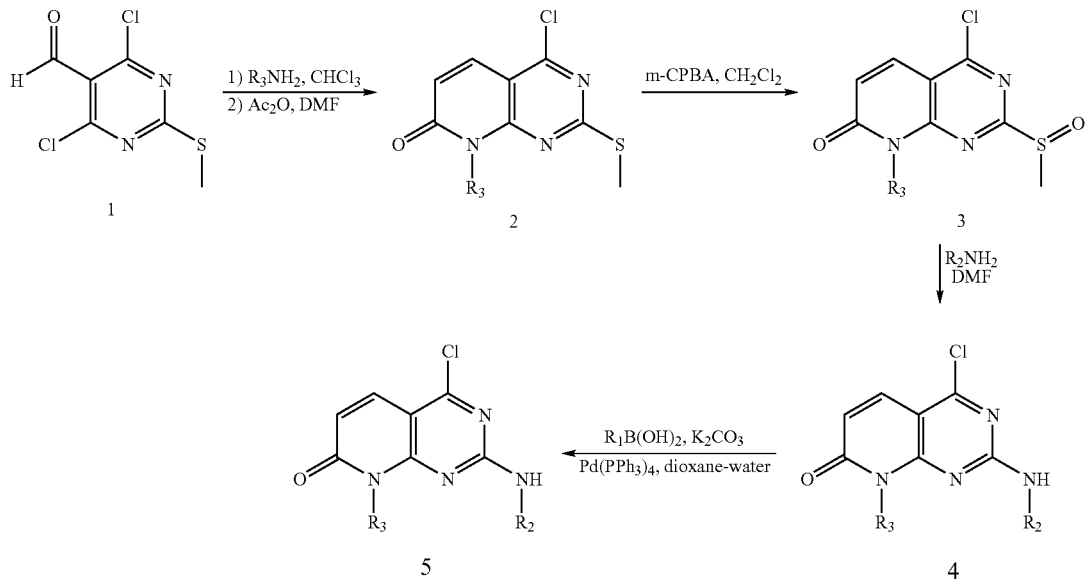

Scheme 3: Route 3

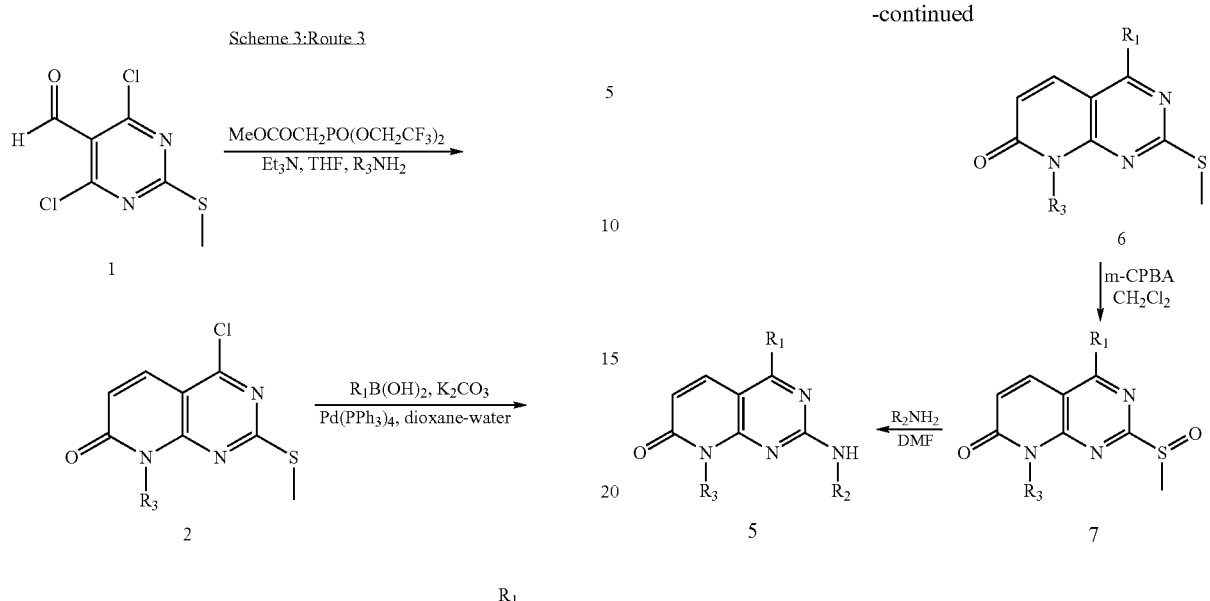

Scheme 4: Route 4

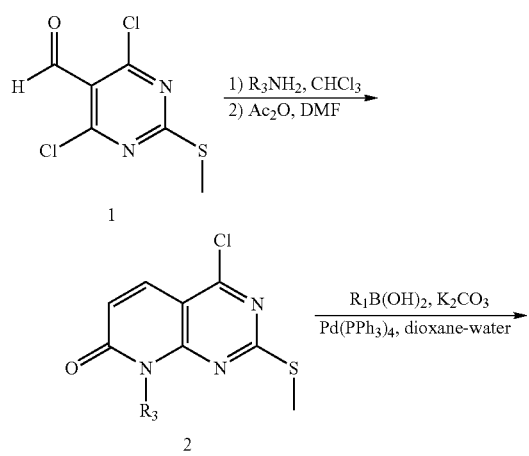

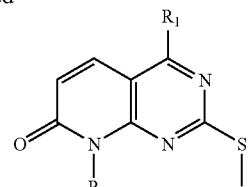

In Routes 1 & 3; Schemes 1 & 3, Compound 1 to Compound 2, while the olefin forming reagent Bis(2,2,2-trifluoroethyl)(methoxycarbonylmethyl)phosphonate is used, alternative cyclization reagents, include, but are not limited to Bis(2,2,2-trifluoroethyl)-(ethoxycarbonylmethyl)phosphonate, Bis(2,2,2-trifluoroethyl)-(isopropoxycarbonylmethyl)phosphonate, (Diethoxy-phosphoryl)-acetic acid methyl ester, (Diisopropoxy-phosphoryl)-acetic acid methyl ester, (Diphenyloxy-phosphoryl)-acetic acid methyl ester, (Diethoxy-phosphoryl)-acetic acid ethyl ester, (Diisopropoxy-phosphoryl)-acetic acid ethyl ester, or (Diphenyloxy-phosphoryl)-acetic acid ethyl ester.

While this reaction as shown in Scheme 1 and Scheme 3 uses triethylamine as a base, suitable alternative bases can include, but are not limited to pyridine, diisopropyl ethyl amine, or pyrrolidone, or combinations thereof.

Further, while the reaction scheme as shown in Scheme 1 and Scheme 3 utilizes tetrahydrofuran as a solvent, it is recognized that suitable alternative organic solvents can be used. Such solvents include, but are not limited to chloroform, methylene chloride, acetonitrile, toluene, DMF, or n-methylpyrrolidine, or combinations thereof.

The reaction temperature of this particular step in the reaction scheme can be varied from room temperature to >100° C., i.e. reflux temperature of the solvent. Alternatively, this reaction process step may be performed under suitable microwave conditions.

In Routes 2 & 4, Schemes 2 & 4, Compound 1 to Compound 2, while the reagent acetic anhydride is shown, this reagent can be replaced with acetyl chloride, or any other suitably acylating reagent.

Further, while the reaction scheme as shown in Scheme 2 and Scheme 4 utilizes chloroform as a solvent, it is recognized that suitable alternative organic solvents can be used. Such solvents include, but are not limited to tetrahydrofuran, methylene chloride, acetonitrile, toluene, DMF, n-methylpyrrolidine, or dioxane, or combinations thereof.

The reaction temperature of this particular step in the reaction scheme can be varied from room temperature to >100° C., i.e. reflux temperature of the solvent. Alternatively, this reaction process step may be performed under suitable microwave conditions.

In Routes 1 & 2; Schemes 1 & 2, Compound 2 to Compound 3, or for Routes 3 & 4, Schemes 3 & 4, Compound 6 to Compound 7, while the oxidizing reagent 3-chloroperoxybenzoic acid (m-cPBA) is used, alternative reagents, include but are not limited to hydrogen peroxide, sodium periodinate, potassium periodinate, Oxone, OsO4, catalytic tertiary amine N-oxide, peracids, such as aryl peracids, i.e. perbenzoic and the aforementioned m-cPBA, or alkylperacids, as such peracetic acid and pertrifluroacetic acid, oxygen, ozone, organic peroxides, peroxide ($H_2O_2$), and inorganic peroxides, potassium and zinc permanganate, potassium persulfate. It is recognized that the peroxide agents can be used in combination with sodium tungstate, acetic acid or sodium hyperchlorite.

It is recognized that the oxidation process may in fact yield Compound 3, or Compound 7, but may also result in the corresponding sulfone, as well as the sulfoxide, or mixtures thereof.

This reaction step, while demonstrated in the schematics with methylene chloride as the solvent, may use alternative organic solvents other than primary amines or alcohols which include, but are not limited to chloroform, acetone, DMF, THF, acetonitrile, dioxane, or DMSO, or combinations thereof. This reaction step may be conducted at about 0° C. to room temperature.

In Routes 1 & 2; Schemes 1 & 2, Compound 3 to Compound 4, or for Route 3 & 4, Schemes 3 & 4, Compound 7 to Compound 5, the reaction solvent of DMF may alternatively be replaced with other suitable anhydrous organic solvents, which does not contain a nucleophile, which include but are not limited to THF, methylene chloride, acetone, acetonitrile, toluene, chloroform, n-methyl-pyrrolidine, or dioxane, or combinations thereof.

This temperature step may be conducted at room temperature to >100° C., i.e. reflux temperature of the solvent. Alternatively, this reaction process step may be performed under suitable microwave conditions.

In Routes 1 & 2, Schemes 1 & 2, Compound 4 to Compound 5, or for Routes 3-4, Schemes 3-4, Compound 2 to Compound 6 wherein Compound 2 or 4 are coupled to arylboronic acids, heteroarylboronic acids or the corresponding boronic acid esters under standard Suzuki coupling conditions. These reaction conditions utilize a palladium catalyst, such as tetrakis(triphenylphosphine)palladium (0),which has been shown to provide good yields of either compound 5 or 6. The reaction conditions may be from room temperature to about 250° C., by heating in an oil bath, or with microwave irradiation. If desired, these Suzuki coupling reactions may be run under microwave conditions.

The aryl or heteroaryl boronic acid or ester intermediates can be synthesized either by the palladium catalyzed coupling of an aryl halide and 4,4,4',4',5,5,5',5'-octamethyl-2,2'-bi-1,3,2-dioxaborolane or the transmetalation of an aryl halide with a Grignard reagent, e.g., isopropylmagnesium bromide followed by a trialkylborate (e.g., triethylborate) in a suitable solvent like THF.

Alternatively, the coupling reaction of 2 or 4 may be performed utilizing aryl or heteroaryl organozinc, organocopper, organotin, or other organometallic reagents known to afford cross-coupling products such as 5 or 6 [See for example: Solberg, J.; Undheim, K. *Acta Chemica Scandinavia* 1989, 62-68, whose disclosure is incorporated by reference herein]. Using the reaction procedures described in the aforementioned WO 02/059083, it has been found that compounds of Formula (III) as described herein, were unable to be synthesized following those procedures. The present invention provides for an alternative method to synthesize compounds of Formula (I) having differing $R_1$ substituents on the C4 position of the pyrido[2,3-d]pyrimidin-7-one pharmacophore. These substituents may be introduced to this position after the pyrido[2,3-d]pyrimide-7-one pharmacophore is substituted with functional groups at the $C_2$ and $N_8$ position. This particular substitution has not previously been available using the reaction conditions as set forth in WO 02/059083.

While it is possible to produce individual compounds using the process illustrated herein, a benefit for these reaction pathways lies in its ability to optimize leads and to make arrays for combinatorial chemistry, with various $R_1$, $R_2$, and $R_3$ substituents.

Another aspect of the invention is a process to make compounds of Formula (I) as defined herein, which comprises reacting a compound of Formula (III), as defined herein with a coupling agent selected from an arylboronic acid, or a heteroarylboronic acid or their corresponding boronic acid esters, with a suitable palladium catalyst to yield a compound of Formula (I). This coupling process takes place under standard Suzuki conditions.

Suitably the arylboronic acids, heteroarylboronic acids, or their corresponding boronic acid esters are $R_1$-boronic acid or an $R_1$-boronic acid ester; e.g. $R_1B(OH)_2$, $R_1B(O-C_{1-4}$ alkyl$)_2$, or

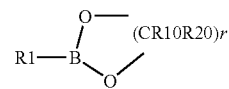

wherein $R_1$, $R_{10}$, and $R_{20}$ is as defined for compounds of Formula (I) herein; and r is an integer having a value of 2 to 6.

The coupling conditions include the use of appropriate solvents. These solvents include, but are not limited to dioxane, THF, DMF, DMSO, NMP, acetone, water, or a combination or a mixture thereof. Preferably, the solvent is THF/$H_2O$, or dioxane/$H_2O$.

The coupling conditions also include the presence of catalytic amount of catalysts and these catalysts include, but not limited to tetrakis(triphenylphosphine)-palladium (0), PdCl2, Pd(OAc)2, (CH3CN)2PdCl2, Pd(dppf)2, or [1,1'-bis(diphenylphosphino)-ferrocene]-dichloropalladium(II).

The coupling reaction may or may not require the presence of a base. Suitable bases include, but are not limited to $NaHCO_3$, $KHCO_3$, $Na_2CO_3$, $K_2CO_3$, KOAc or combination or mixture thereof. Preferably, the base is $K_2CO_3$ and KOAc.

The coupling reaction may or may not require heating. The heating can be carried out with a regular oil bath or microwave irrediations and the temperature can be varied from room temperature to >100° C., i.e. reflux temperature of the solvent. The coupling reaction may or may not require a sealed reaction vessel and the internal pressure can be varied from one atmosphere to 100 atmospheres.

The aryl or heteroaryl boronic acid or ester intermediates containing the $R_1$ moiety, used in the Suzuki coupling reactions may or may not be commercially available and they can be prepared by utilizing proper methods in the literature known to those with appropriate training. Examples of these methods include, but not limited to palladium catalyzed coupling of an aryl halide and 4,4,4',4',5,5,5',5'-octamethyl-2,2'-bi-1,3,2-dioxaborolane or the transmetalation of an aryl halide with a Grignard reagent, e.g., isopropylmagnesium bromide followed by a trialkylborate (e.g., triethylborate) in a suitable solvent. These solvents include, but not limited to CH2Cl2, chloroform, CH3CN, benzene, THF, hexane, ethyl ether, tert-butyl methyl ether, DMSO, DMF, toluene, n-methyl-pyrrolidine, dioxane. The reaction temperature can be varied from −78° C. to >100° C., i.e. reflux temperature of the solvent. Alternatively, this reaction process step may or may not be performed under suitable microwave irradiation conditions. This reaction may or may not require a sealed reaction vessal and the internal pressure can be varied from one atmosphere to 100 atmospheres.

One embodiment of the inventionare the arylboronic acids and esters which are generically referred to as $R_1B(OH)_2$, $R_1B(O—C_{1-4}$ alkyl$)_2$, or

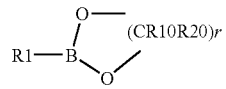

wherein $R_{10}$ and $R_{20}$ are independently selected from hydrogen or $C_{1-4}$ alkyl;

r is an integer having a value of 2 to 6;

$R_1$ is an optionally substituted phenyl, as defined according to Formula (I).

Suitably, the phenyl ring is substituted by one or more times independently at each occurrence by halogen, $C_{1-4}$ alkyl, halo-substituted-$C_{1-4}$ alkyl, cyano, nitro, $(CR_{10}R_{20})_{v'}$ $NR_dR_{d'}$, $(CR_{10}R_{20})_vC(O)R_{12}$, $SR_5$, $S(O)R_5$, $S(O)_2R_5$, or $(CR_{10}R_{20})_vOR_{13}$, $(CR_{10}R_{20})_vC(Z)NR_4R_{14}$, $(CR_{10}R_{20})_vC(Z)OR_8$, $(CR_{10}R_{20})_vCOR_a$, $(CR_{10}R_{20})_vC(O)H$, $SR_5$, $S(O)R_5$, $S(O)_2R_5$, $(CR_{20})_vOR_8$, $ZC(Z)R_{11}$, $N(R_{10'})C(Z)R_{11}$, $N(R_{10'})S(O)_2R_7$, $C(Z)N(R_{10})(CR_{10}R_{20})_vR_b$, $C(Z)O(CR_{10}R_{20})_vR_b$, $N(R_{10})C(Z)(CR_{10}R_{20})_vR_b$; $N(R_{10'})C(Z)N(R_{10'})(CR_{10}R_{20})_vR_b$; or $N(R_{10'})OC(Z)(CR_{10}R_{20})_vR_b$; and wherein $R_a$, is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vN(R_{10'})S(O)_2R_7$, or $(CR_{10}R_{20})_vNR_4R_{14}$; and wherein the aryl, arylalkyl, heteroaryl, heteroaryl alkyl may be optionally substituted;

$R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety, which moieties excluding hydrogen, may all be optionally substituted;

$R_d$ and $R_{d'}$ are each independently selected from hydrogen, $C_{1-4}$ alkyl, $C_{3-5}$ cycloalkyl, $C_{3-5}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$, and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_4$ and $R_{1-4}$ cyclized ring are optionally substituted;

$R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted;

$R_8$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted independently at each occurrence;

$R_{9'}$ is independently selected at each occurrence from hydrogen, or $C_{1-4}$ alkyl;

m is independently selected at each occurrence from 0 or an integer having a value of 1 or 2;

v is independently selected at each occurrence from 0, or an integer having a value of 1 to 2.

v' is independently selected at each occurrence from 0 or an integer having a value of 1 or 2;

$R_4$ and $R_{14}$ are each independently selected at each occurrence from hydrogen, $C_{1-10}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or heteroaryl $C_{1-4}$ alkyl; or the $R_4$ and $R_{14}$ together with the nitrogen which they are attached form an unsubstituted or substituted heterocyclic ring of 4 to 7 members, which ring optionally contains an additional heteroatom selected from oxygen, sulfur or nitrogen; and wherein all of these moieties, excluding hydrogen, are optionally substituted;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form an optionally substituted 5 to 7 membered ring which optionally contains an additional heteroatom selected from oxygen, sulfur or $NR_{9'}$;

$R_5$ is independently selected at each occurrence from hydrogen, $C_{1-4}$ alkyl, $C_{2-4}$ alkenyl, $C_{2-4}$ alkynyl or $NR_4R_{4'}$, excluding the moieties $SR_5$ being $SNR_4R_{14'}$, $S(O)_2R_5$ being $SO_2H$ and $S(O)R_5$ being SOH;

$R_{10}$ and $R_{20}$ are independently selected at each occurrence from hydrogen or $C_{1-4}$ alkyl; $R_{10'}$ is independently selected at each occurrence from hydrogen or $C_{1-4}$ alkyl;

$R_{11}$ is independently selected at each occurrence from hydrogen, or $C_{1-4}$ alkyl;

$R_{12}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or heterocyclyl$C_{1-4}$ alkyl, and wherein these moieties, excluding hydrogen, may be optionally substituted; and $R_{13}$ is independently selected at each occurrence from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted.

In one embodiment, the phenyl ring is substituted by $C(Z)N(R_{10'})(CR_{10}R_{20})_vR_b$, or $N(R_{10'})C(Z)(CR_{10}R_{20})_vR_b$, and optionally another substituent $(R_{1'})g$, and g is 1 or 2. $R_b$ is suitably as defined in Formula (I) herein. Suitably, $R_{1'}$ is independently selected at each occurrence from halogen, $C_{1-4}$ alkyl, halo-substituted-$C_{1-4}$ alkyl, cyano, nitro, $(CR_{10}R_{20})_{v'}$ $NR_dR_{d'}$, $(CR_{10}R_{20})_vC(O)R_{12}$, $SR_5$, $S(O)R_5$, $S(O)_2R_5$, or $(CR_{10}R_{20})_vOR_{13}$. Preferably $R_{1'}$ is independently selected at each occurrence from $C_{1-4}$ alkyl, such as methyl, or halogen, such as fluorine or chlorine or bromine, or halo-substituted-$C_{1-4}$ alkyl, such as $CF_3$.

In one embodiment, the $C(Z)N(R_{10'})(CR_{10}R_{20})_vR_b$, is substituted on the phenyl ring in the 4-position or the 5-position, preferably the 5-position. If an $R_{1'}$ moiety is present, it is preferably in the 2-position, and $R_1$ is independently selected at each occurrence from $C_{1-4}$ alkyl, such as methyl, or halogen, such as fluorine or chlorine or bromine. Preferably the aryl is 4-methyl-N-1,3-thiazol-2-ylbenzamide, N-(4-fluorophenyl)-4-methylbenzamide, or 4-methyl-N-propylbenzamide. In another embodiment the phenyl ring is substituted one or more times, preferably 1 to 4 times by $R_1$, and $R_{1'}$ is independently selected at each occurrence from halogen, $C_{1-4}$ alkyl, halo-substituted-$C_{1-4}$ alkyl, cyano, nitro, $(CR_{10}R_{20})_{v'}$ $NR_dR_{d'}$, $(CR_{10}R_{20})_vC(O)R_{12}$, $SR_5$, $S(O)R_5$, $S(O)_2R_5$, or $(CR_{10}R_{20})_{v'}OR_{13}$. Preferably, the phenyl ring is di-substituted in the 2,4-position. In another embodiment $R_{1'}$ is independently selected at each occurrence from $C_{1-4}$ alkyl, such as methyl, or halogen, such as fluorine or chlorine or bromine, or halo-substituted-$C_{1-4}$ alkyl, such as $CF_3$. Preferably, the aryl is phenyl, 2-methyl-4-fluorophenyl, 2-methylphenyl, 2-chlorophenyl, 2-fluorophenyl, or 2-methyl-3-fluorophenyl.

Another aspect of the invention is another process to make compounds of Formula (I) as defined herein, which comprises reacting a compound of Formula (III), as defined herein utilizing aryl or heteroaryl organozinc, organocopper, organotin, or other organometallic reagents known in the art to afford a cross-coupling product of the desired R1 moiety in the C4 position of the template yielding a compound of Formula (I).

This coupling reaction may be performed utilizing aryl or heteroaryl organozinc (e.g., $R_1$—ZnBr, $R_1$—ZnCl, $R_1$—Zn—$R_1$), organocopper [e.g., $(R_1)_2$—CuLi], organotin (e.g., $R_1$—Sn(CH$_3$)$_3$, $R_1$—Sn(CH$_2$CH$_2$CH$_2$CH$_3$)$_3$], or other organometallic reagents to afford the cross-coupling product. The $R_1$ aryl and heteroaryl moiety is as defined for Formula (I) herein. If the desired aryl or hetero aryl organozinc (e.g., $R_1$—ZnBr, $R_1$—ZnCl, $R_1$—Zn—$R_1$), organocopper [e.g., $(R_1)_2$—CuLi], organotin (e.g., $R_1$—Sn(CH$_3$)$_3$, $R_1$—Sn(CH$_2$CH$_2$CH$_2$CH$_3$)$_3$], or other organometallic reagent is not commercially available, they can readily be prepared by utilizing proper methods, known in the literature.

These types of coupling reactions require the use of appropriate solvents. Such solvents include, but are not limited to dioxane, THF, methylene chloride, chloroform, benzene, hexane, ethyl ether, tert-butyl methyl ether or a combination or a mixture thereof.

The coupling reaction may, or may not, require the presence of catalytic amount of a catalyst. Such catalysts include, but are not limited to tetrakis(triphenylphosphine)palladium (0), PdCl$_2$, Pd(OAc)$_2$, (CH$_3$CN)$_2$PdCl$_2$, Pd(dppf)$_2$.

The reaction temperature can be varied from −78° C. to >100° C., i.e. reflux temperature of the solvent. Alternatively, this reaction process step may be performed under suitable microwave irradiation conditions, if needed. This reaction may, or may not, require a sealed reaction vessel and the internal pressure can be varied from one atmosphere to 100 atmospheres.

Suitably, the $R_1$ moiety is as defined for compounds of Formula (I) herein.

In one embodiment, the $R_1$ moiety is an optionally substituted aryl ring, preferably a phenyl ring. In another embodiment, the phenyl ring is substituted by $C(Z)N(R_{10'})(CR_{10}R_{20})_vR_b$, or $N(R_{10'})C(Z)(CR_{10}R_{20})_vR_b$, and optionally another substituent $(R_{1'})$g, and g is 1 or 2. $R_b$ is suitably as defined in Formula (I) herein. Suitably, $R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_{v'}OR_{13}$. Preferably $R_{1'}$ is independently selected at each occurrence from $C_{1-4}$ alkyl, such as methyl, or halogen, such as fluorine or chlorine or bromine, or halo-substituted-$C_{1-4}$ alkyl, such as $CF_3$.

In one embodiment, the $C(Z)N(R_{10'})(CR_{10}R_{20})_vR_b$, is substituted on the phenyl ring in the 4-position or the 5-position, preferably in the 5-position. If an $R_{1'}$ moiety is present, it is preferably in the 2-position, and $R_{1'}$ is independently selected at each occurrence from $C_{1-4}$ alkyl, such as methyl, or halogen, such as fluorine or chlorine or bromine. Preferably the aryl is 4-methyl-N-1,3-thiazol-2-ylbenzamide, N-(4-fluorophenyl)-4-methylbenzamide, or 4-methyl-N-propylbenzamide.

In another embodiment the phenyl ring is substituted one or more times, preferably 1 to 4 times by $R_{1'}$ and $R_{1'}$ is independently selected at each occurrence from halogen, $C_{1-4}$ alkyl, halo-substituted-$C_{1-4}$ alkyl, cyano, nitro, $(CR_{10}R_{20})_vNR_dR_{d'}$, $(CR_{10}R_{20})_vC(O)R_{12}$, $SR_5$, $S(O)R_5$, $S(O)_2R_5$, or $(CR_{10}R_{20})_{v'}OR_{13}$. Preferably, the phenyl ring is di-substituted in the 2,4-position.

In another embodiment $R_{1'}$ is independently selected at each occurrence from $C_{1-4}$ alkyl, such as methyl, or halogen, such as fluorine or chlorine or bromine, or halo-substituted-$C_{1-4}$ alkyl, such as $CF_3$. Preferably, the aryl moiety is a 2-methyl-4-fluorophenyl.

Additional methods to produce compounds of Formula (II), wherein G1 is NH, are shown in Scheme 5 below.

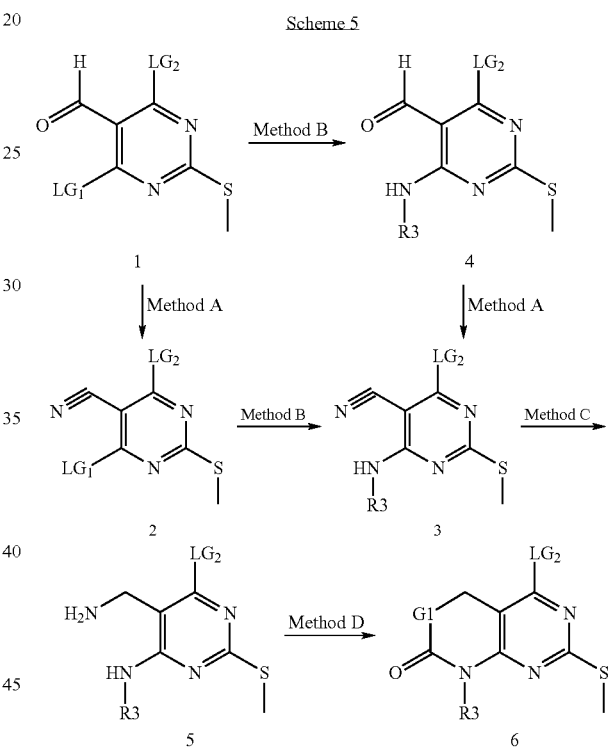

Scheme 5

Method A is for conversion of 1 to 2. Examples of the methods include, but are not limited to condensation with NH$_2$OH followed by treatment with thionyl chloride (SOCl$_2$) [e.g., Santilli et al., *J. Heterocycl. Chem.* (1971), 445-53] or oxidation of —CHO group to —COOH followed by formation of a primary amide (—CONH$_2$) and treatment with POCl$_3$. Suitable Method A can also be utilized to furnish the conversion of 4 to 3—Scheme 5.

Leaving groups (LG, described as Leaving group 1 (LG1) & LG2) in 1 (or 2), or elsewhere, can be independently selected from —Cl, —Br, —I, or —OTf and these groups can be installed through the transformation of another functional group (e.g. —OH) by following the methods well known in the art (e.g., treatment of the —OH compound with POCl$_3$).

Method B is for selective displacement of suitable aldehyde 1 or nitrile 2 with an amine (R$_3$—NH$_2$). This type of displacement may be achieved using triethylamine and the desired amine R$_3$NH$_2$ in chloroform at room temperature for 10 minutes. The reaction was very effective for a range of alkyl amines (78-95% yield). For aryl or heteroaryl amines, elevated temperatures (reflux), longer reaction time (24 hours) and presence of NaH (or Na) may be necessary for reaction completion. Use of the base could be omitted when 3 or more equivalent of the desired amine were used. Other suitable bases include but are not limited to pyridine, diisopropyl ethylamine or pyrrolidine, which may also be used in an appropriate organic solvent, including but not limited to THF, diethyl ether, DCM, DMF, DMSO, toluene or dioxane.

Method C is for the reduction of nitrile 3 to amine 5. 5 may be considered a primary amine ($NH_2$), a secondary amine (because of —$NH(R_3)$) or an amine (as it contains basic nitrogen). This method includes, but is not limited to $BH_3$ in appropriate organic solvent, such as THF, DCM, toluene, DMSO, diethyl ether or dioxane. Other suitable reduction reagents, include but are not limited to $NaBH_4$, LAR or DIBAL. Method C may require elevated temperatures (e.g., heating, refluxing or irradiating with microwave). Another example of the method is hydrogenation ($H_2$) in the presence of transition metals (e.g., Pd/C, Raney-Ni, $PdCl_2$).

Method D is for the cyclization of 5 to 6. This method requires the presence of a cyclization reagent (e.g., CDI, $COCl_2$, tri-phosgene, or phenyl chloroformate methyl chloroformate). Presence of a suitable base may help the reaction to go to completion and examples of the base include, but not limited to triethyl amine, diisopropylethylamine or pyrrolidine. Reaction solvent can be DCM, THF, toluene, DMSO, or DMF.

Compounds of Formula (VI) are represented by the formula:

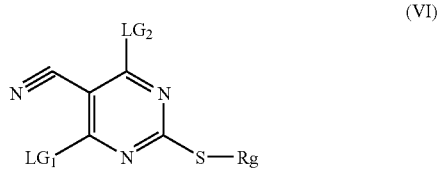

(VI)

wherein
LG2 is chloro, bromo, iodo, or O—$S(O)_2CF_3$;
LG1 is chloro, bromo, iodo, or O—$S(O)_2CF_3$; and
Rg is an optionally substituted $C_{1-10}$ alkyl.

In one embodiment, LG2 is chloro. IN a further embodimdnet, LG1 is chloro. In another embodiment, Rg is methyl.

Compounds of Formula (VII) are represented by the formula:

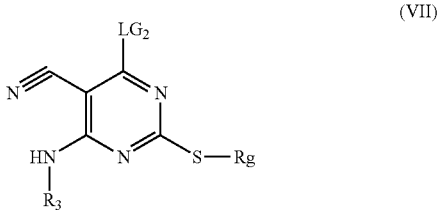

(VII)

wherein
LG2 is chloro, bromo, iodo, O—$S(O)_2CF_3$;
Rg is an optionally substituted $C_{1-10}$ alkyl;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted.

Suitably $R_3$ is substituted as defined herein for compounds of Formula (I).

In one embodiment, Rg is methyl. In another embodiment, LG2 is chloro.

Another aspect of the invention are compounds of Formula (VIII) represented by the formula:

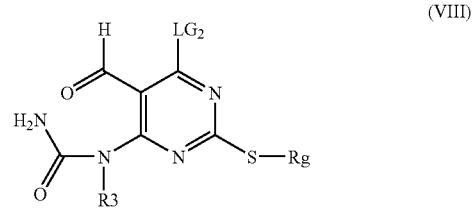

(VIII)

wherein
LG2 is chloro, bromo, iodo, O—$S(O)_2CF_3$;
Rg is an optionally substituted $C_{1-10}$ alkyl;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted.

Suitably $R_3$ is substituted as defined herein for compounds of Formula (I).

In an embodiment of the invention LG2 is chloro. In another embodiment, Rg is methyl. In another embodiment, LG2 is chloro, Rg is methyl, and $R_3$ is an optionally substituted phenyl.

Another aspect of the present invention is the novel process, shown in Scheme-6 below, to make the transformation of a compound of Formula (VIII) to a compound of Formula (II) wherein Rx is now defined as LG2, and m=0.

Scheme 6

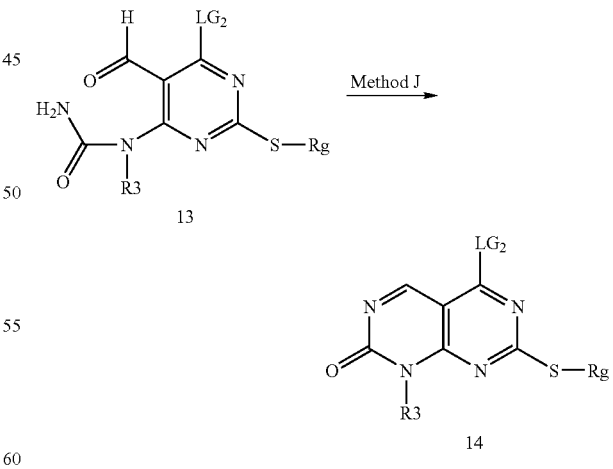

Method J is for imine formation to convert compound 13 to a compound of Formula (II) wherein m is 0, compound 14. This can be achieved by following various strategies known in the art. Strategies include, but are not limited to treatment with an acid including TFA, HOAc, HCl, $H_2SO_4$ or a Lewis acid (e.g., AlC13). This conversion may require elevated temperatures (e.g., heat, solvent reflux, microwave irradiation) in appropriate organic solvents (e.g., THF, CH$_2$Cl$_2$, toluene, DMSO, CH$_3$CN or dioxane).

Compounds of Formula (VIII) (compound 13—Scheme 7) may be made by reacting the compound 4 using Method I as described below. Compound 4 may be obtained from compound 1 using Method B as described above.

Scheme 7

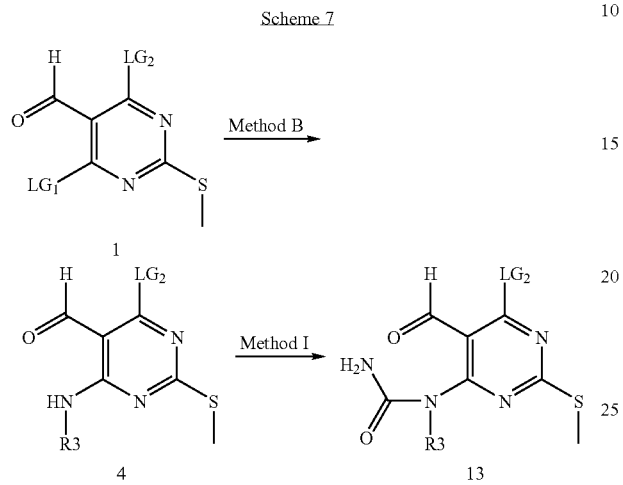

Method I is for urea formation to convert 4 to 13. This can be achieved by following strategies well-established in the art. Strategies include, but are not limited to reaction with suitably substituted isocyanate, such as ClSO$_2$NCO (or Me$_3$SiNCO) in a aprotic organic solvent, such as toluene, methylene chloride, chloroform, benzene, THF, hexane, optionally with a non-nucleophilic base, such as triethylamine, diisopropyl ethylamine, pyridine, followed by reaction with ammonia or H$_2$O; or by reaction with COCl$_2$ (CDI, or triphosgene) or methylchloroformate or other chloroformates in an aprotic organic solvent, such as toluene, methylene chloride, chloroform, benzene, THF, hexane, optionally with a non-nucleophilic base, such as triethylamine, diisopropyl ethylamine, pyridine, followed by treatment with NH$_3$ (or NH$_4$OH); or by reaction with ClCO$_2$Me (or ClCO$_2$Et) in a aprotic organic solvent, such as toluene, methylene chloride, chloroform, benzene, THF, hexane, optionally with a non-nucleophilic base, such as triethylamine, diisopropyl ethylamine, pyridine followed by treatment with NH$_3$ (or NH$_4$OH) or reaction with NH$_2$CO$_2$(t-Bu), followed by reaction with ammonia. This reaction may, or may not, require heating (e.g, temperature between r.t. and 250° C.). The heating can be carried out in any manner and may include the use of an oil bath or microwave irradiation.

Another aspect of the invention is a process for making a compound of Formula (III):

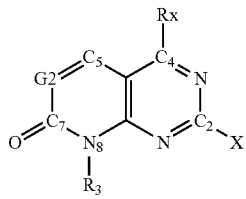

or

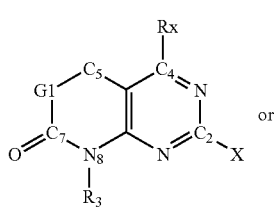

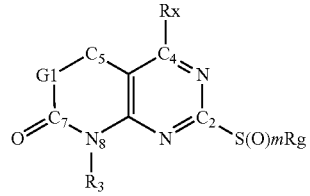

wherein
G1 is CH$_2$ or NH:
G2 is CH or nitrogen;
Rx is chloro, bromo, iodo, or O—S(O)$_2$CF$_3$;
and wherein X and R$_3$ are as defined above for compounds of Formula (I); comprising reacting a compound of the formula

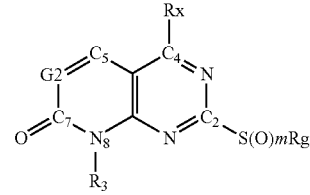

wherein
G1 is CH$_2$ or NH:
G2 is carbon or nitrogen;
Rx is chloro, bromo, iodo, or O—S(O)$_2$CF$_3$;
Rg is a C$_{1-10}$alkyl;
m is an integer having a value of 1, or 2;
R$_3$ is a C$_{1-10}$ alkyl, C$_{3-7}$ cycloalkyl, C$_{3-7}$ cycloalkyl C$_{1-10}$ alkyl, aryl, arylC$_{1-10}$ alkyl, heteroaryl, heteroarylC$_{1-10}$ alkyl, heterocyclic or a heterocyclylC$_{1-10}$ alkyl moiety, and wherein each of these moieties may be optionally substituted;
with X—Y wherein X is R$_2$, OR$_{2'}$, S(O)$_m$R$_{2'}$, (CH$_2$)$_n$N(R$_{11}$) S(O)$_m$R$_{2'}$, (CH$_2$)$_n$N(R$_{11}$)C(O)R$_{2'}$, (CH$_2$)$_n$NR$_4$R$_{14}$, or (CH$_2$)$_n$N(R$_{2'}$)(R$_{2''}$), or N(R$_{10'}$)—R$_h$—NH—C(=N—CN) NRqRq'; and R$_2$, R$_{2'}$, m, n', R$_{11}$, R$_{10'}$, R$_h$ and RqRq' are as defined according to Formula (I or III) herein; and
Y is hydrogen, a metal, a boronic acid derivative, or a trialkyl tin derivative, in an anhydrous organic solvent which does not contain a nucleophile to yield a compound of Formula (III).

In the transformation of (II) to (III), when Y is hydrogen then X is the following:
a) X=OR$_{2'}$, or X is S(O)$_m$R$_{2'}$ (and m=0); or
b) X is (CH$_2$)$_n$N(R$_{10'}$)S(O)$_m$R$_{2'}$, (CH$_2$)$_n$N(R$_{10'}$)C(O)R$_{2'}$, (CH$_2$)$_n$NR$_4$R$_{14}$, or (CH$_2$)$_n$N(R$_{2'}$)(R$_{2''}$) and n'=0; or
c) X=R$_2$ and R$_2$=(CR$_{10}$R$_{20}$)$_q$X$_1$(CR$_{10}$R$_{20}$)$_q$C(A$_1$)(A$_2$) (A$_3$), q'=0, and X$_1$ is N(R$_{10'}$), O, S(O)$_m$ and m=0.
d) when X is N(R$_{10'}$)—R$_h$—NH—C(=N—CN)NRqRq'.

In the transformation of (II) to (III), when Y is a metal, such as Li, Mg, or any other appropriate metal or metal complex; then X is the following:

a) X is $R_2$, and $R_2$ is $C_{1-10}$ alkyl, $C_{3-7}$ cycloalkyl, $C_{3-7}$ cycloalkyl$C_{1-10}$ alkyl, aryl, aryl$C_{1-10}$ alkyl, heteroaryl, heteroaryl $C_{1-10}$ alkyl, heterocyclic, or a heterocyclyl$C_{1-10}$ alkyl moiety.

In the transformnation of (II) to (III), when Y is a boronic acid, $(B(OH)_2)$ or boronic ester derivatives; then X is the following a) $X=R_2$, and $R_2$=aryl, or heteroaryl.

When Y is a trialkyl tin derivative, such as $(C_{1-4}$ alkyl$)_3$Sn, then a) $X=R_2$, and $R_2$=aryl, or heteroaryl.

It is recognized that for compounds of Formula (II) or (III) when G1 is NH, the nitrogen may need to be protected under standard conditions, and then deprotected after the transformation, as desired.

The anhydrous organic solvents include, but are not limited to $CH_2Cl_2$, chloroform, $CH_3CN$, benzene, THF, hexane, ethyl ether, tert-butyl methyl ether, DMSO, DMF and toluene.

This reaction may or may not require heating (e.g., temperature between r.t. and 300° C.) and the heating can be carried out with, but not limited to a regular oil bath or microwave irradiations;

This reaction may or may not require the presence of bases, and the bases include, but are not limited to triethyl amine, duisopropyl ethyl amine, NaH, n-Buli, tert-BuLi, tert-BuOK, $Li_2CO_3$, $Cs_2CO_3$ and pyridine. It is recognized that some of these bases will be incompatible with the organic solvents specified above.

This reaction may or may not be carried out in a sealed reaction vessel and the internal pressure may be higher than one atomosphere (e.g., between 1 and 100 atmospheres).

This reaction may or may not require the presence of catalytic amount of catalysts containing transition metals (e.g., Pd, Cu, Ni or W). These catalysts include but are not limited to Pd/C, Pd(PPh$_3$)$_4$ and PdCl$_2$.

Another aspect of the invention is a process for making a compound of Formula (III),

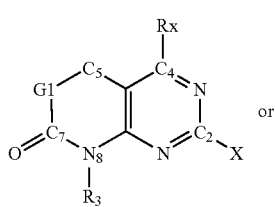

(III)

or

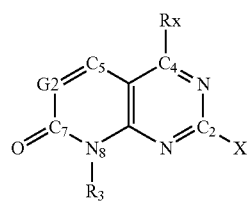

(IIIa)

wherein
G1 is $CH_2$ or NH:
G2 is CH or nitrogen;
Rx is chloro, bromo, iodo, or $O-S(O)_2CF_3$;

and wherein X and $R_3$ are as defined above for compounds of Formula (III); comprising reacting a compound of the formula

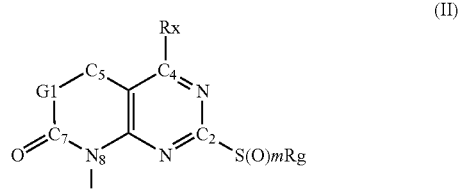

(II)

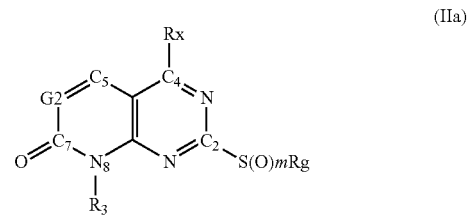

(IIa)

wherein
G1 is $CH_2$ or NH:
G2 is CH or nitrogen;
Rx is chloro, bromo, iodo, or $O-S(O)_2CF_3$;
Rg is a $C_{1-10}$ alkyl;
m is an integer having a value of 1, or 2;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;
with X—Y wherein X is $R_2$, $OR_{2'}$, $S(O)_mR_{2'}$, $(CH_2)_nN(R_{11})S(O)_mR_{2'}$, $(CH_2)_nN(R_{11})C(O)R_{2'}$, $(CH_2)_nNR_4R_{14}$, or $(CH_2)_nN(R_{2'})(R_{2''})$, or $N(R_{10'})$—$R_h$—NH—C(=N—CN)NRqRq'; and $R_2$, $R_{2'}$, m, n', $R_{11}$, $R_{10'}$, $R_h$ and RqRq' are as defined according to Formula (I or III) herein; and
Y is $NH_2$, $NH(R_{10})$, OH, or SH, in an anhydrous organic solvent to yield a compound of Formula (III), provided that
a) X is $R_2$ and $R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl $C_{1-10}$ alkyl; or
b) X is $(CH_2)_nN(R_{10'})S(O)_mR_{2'}$, $(CH_2)_nN(R_{10'})C(O)R_{2'}$, $(CH_2)_nNR_4R_{14}$, $(CH_2)_nN(R_{2'})(R_{2''})$, and n' is greater than 2.

The anhydrous organic solvents include, but are not limited to $CH_2Cl_2$, chloroform, $CH_3CN$, benzene, THF, hexane, ethyl ether, tert-butyl methyl ether, DMSO, DMF and toluene, DMF, acetone, toluene, n-methyl-pyrrolidine, or dioxane, or a combination or mixture thereof.

This reaction may or may not require heating (e.g., temperature between room temperature and 300° C.) and the heating can be carried out with, but not limited to a regular oil bath or microwave irradiations;

This reaction may or may not require the presence of bases, and the bases include, but are not limited to triethyl amine, diisopropyl ethyl amine, NaH, n-Buli, tert-BuLi, tert-BuOK, $Li_2CO_3$, $Cs_2CO_3$ and pyridine. It is recognized that some of these bases will be incompatible with the organic solvents specified above.

This reaction may or may not be carried out in a sealed reaction vessel and the internal pressure may be higher than one atomosphere (e.g., between 1 and 100 atmospheres).

This reaction may or may not require the presence of catalytic amount of catalysts containing transition metals (e.g., Pd, Cu, Ni or W). These catalysts include but are not limited to Pd/C, Pd(PPh$_3$)$_4$ and PdCl$_2$. It is recognized that use of these metals is generally not needed for simple transformations.

Exemplified Compounds of Formulas (II):
4-Chloro-8-(4-trifluoromethyl-phenyl)-2-methylsulfanyl-8H-pyrido[2,3-d]pyrimidin-7-one; 4-Chloro-8-(4-trifluoromethyl-phenyl)-2-methylsulfinyl-8H-pyrido[2,3-d]pyrimidin-7-one;
4-Chloro-8-(2,4-difluoro-phenyl)-2-methylsulfanyl-8H-pyrido[2,3-d]pyrimidin-7-one;
4-Chloro-8-(2,4-difluoro-phenyl)-2-methylsulfinyl-8H-pyrido[2,3-d]pyrimidin-7-one;
4-Chloro-8-(2,6-difluoro-phenyl)-2-methylsulfanyl-8H-pyrido[2,3-d]pyrimidin-7-one;
2-(Hydroxy-hydroxymethyl-ethylamino)-4-Chloro-8-(2,6-difluoro-phenyl)-8H-pyrido[2,3-d]pyrimidin-7-one; and
4-Chloro-8-(2,6-difluoro-phenyl)-2-methylsulfinyl-8H-pyrido[2,3-d]pyrimidin-7-one.

Exemplified Compounds of Formula (III):
2-(Hydroxy-hydroxymethyl-ethylamino)-4-Chloro-8-(4-trifluoromethyl-phenyl)-8H-pyrido[2,3-d]pyrimidin-7-one;
2-(Hydroxy-hydroxymethyl-ethylamino)-4-Chloro-8-(2,4-difluoro-phenyl)-8H-pyrido[2,3-d]pyrimidin-7-one.

Exemplified compounds of Formula (I) which may be produced using the processes described herein include:
2-(Hydroxy-hydroxymethyl-ethylamino)-4-(2-methylsulfanyl-phenyl)-8-(4-trifluoromethyl-phenyl)-8H-pyrido[2,3-d]pyrimidin-7-one
2-(Hydroxy-hydroxymethyl-ethylamino)-4-(3-methylsulfanyl-phenyl)-8-(4-trifluoromethyl-phenyl)-8H-pyrido[2,3-d]pyrimidin-7-one
2-(Hydroxy-hydroxymethyl-ethylamino)-4-phenyl-8-(4-trifluoromethyl-phenyl)-8H-pyrido[2,3-d]pyrimidin-7-one
2-(Hydroxy-hydroxymethyl-ethylamino)-4-(3-chlorophenyl)-8-(4-trifluoromethyl-phenyl)-8H-pyrido[2,3-d]pyrimidin-7-one
2-(Hydroxy-hydroxymethyl-ethylamino)-4-(4-chlorophenyl)-8-(4-trifluoromethyl-phenyl)-8H-pyrido [2,3-d]pyrimidin-7-one
2-(Hydroxy-hydroxymethyl-ethylamino)-4-(3,4-diflorophenyl)-8-(4-trifluoromethyl-phenyl)-8H-pyrido[2,3-d]pyrimidin-7-one
2-(Hydroxy-hydroxymethyl-ethylamino)-4-(2-chlorophenyl)-8-(4-trifluoromethyl-phenyl)-8H-pyrido[2,3-d]pyrimidin-7-one
2-(Hydroxy-hydroxymethyl-ethylamino)-4-(4-methoxyphenyl)-8-(4-trifluoromethyl-phenyl)-8H-pyrido[2,3-d]pyrimidin-7-one
2-(Hydroxy-hydroxymethyl-ethylamino)-4-(3-methoxyphenyl)-8-(4-trifluoromethyl-phenyl)-8H-pyrido[2,3-d]pyrimidin-7-one
2-(Hydroxy-hydroxymethyl-ethylamino)-4-(2-methoxyphenyl)-8-(4-trifluoromethyl-phenyl)-8H-pyrido[2,3-d]pyrimidin-7-one
8-(2,4-Difluoro-phenyl)-2-(2-hydroxy-1-hydroxymethyl-ethylamino)-4-(3-methylsulfanyl-phenyl)-8H-pyrido[2,3-d]pyrimidin-7-one
8-(2,4-Difluoro-phenyl)-2-(2-hydroxy-1-hydroxymethyl-ethylamino)-4-(4-methylsulfanyl-phenyl)-8H-pyrido[2,3-d]pyrimidin-7-one
8-(2,4-Difluoro-phenyl)-2-(2-hydroxy-1-hydroxymethyl-ethylamino)-4-(2-methylsulfanyl-phenyl)-8H-pyrido[2,3-d]pyrimidin-7-one
8-(2,4-Difluoro-phenyl)-2-(2-hydroxy-1-hydroxymethyl-ethylamino)-4-(3,4-difluorophenyl)-8H-pyrido[2,3-d]pyrimidin-7-one
8-(2,4-Difluoro-phenyl)-2-(2-hydroxy-1-hydroxymethyl-ethylamino)-4-(2-methoxyphenyl)-8H-pyrido[2,3-d]pyrimidin-7-one
8-(2,4-Difluoro-phenyl)-2-(2-hydroxy-1-hydroxymethyl-ethylamino)-4-(4-methoxyphenyl)-8H-pyrido[2,3-d]pyrimidin-7-one
8-(2,4-Difluoro-phenyl)-2-(2-hydroxy-1-hydroxymethyl-ethylamino)-4-(2-biphenyl)-8H-pyrido[2,3-d]pyrimidin-7-one
8-(2,4-Difluoro-phenyl)-2-(2-hydroxy-1-hydroxymethyl-ethylamino)-4-(3-biphenyl)-8H-pyrido[2,3-d]pyrimidin-7-one
8-(2,4-Difluoro-phenyl)-2-(2-hydroxy-1-hydroxymethyl-ethylamino)-4-(2-tolyl)-8H-pyrido[2,3-d]pyrimidin-7-one
8-(2,4-Difluoro-phenyl)-2-(2-hydroxy-1-hydroxymethyl-ethylamino)-4-(3-fluoro-4-biphenyl)-8H-pyrido[2,3-d]pyrimidin-7-one
8-(2,4-Difluoro-phenyl)-2-(2-hydroxy-1-hydroxymethyl-ethylamino)-4-(4-chlorophenyl)-8H-pyrido[2,3-d]pyrimidin-7-one
8-(2,4-Difluoro-phenyl)-2-(2-hydroxy-1-hydroxymethyl-ethylamino)-4-(3-chlorophenyl)-8H-pyrido[2,3-d]pyrimidin-7-one
8-(2,4-Difluoro-phenyl)-2-(2-hydroxy-1-hydroxymethyl-ethylamino)-4-(3-fluorophenyl)-8H-pyrido[2,3-d]pyrimidin-7-one
8-(2,4-Difluoro-phenyl)-2-(2-hydroxy-1-hydroxymethyl-ethylamino)-4-(3-methoxyphenyl)-8H-pyrido[2,3-d]pyrimidin-7-one
8-(2,4-Difluoro-phenyl)-2-(2-hydroxy-1-hydroxymethyl-ethylamino)-4-(3,5-difluorophenyl)-8H-pyrido[2,3-d]pyrimidin-7-one
8-(2,6-Difluoro-phenyl)-2-(2-hydroxy-1-hydroxymethyl-ethylamino)-4-(2-methylthiophenyl)-8H-pyrido[2,3-d]pyrimidin-7-one
8-(2,6-Difluoro-phenyl)-2-(2-hydroxy-1-hydroxymethyl-ethylamino)-4-(3-methylthiophenyl)-8H-pyrido[2,3-d]pyrimidin-7-one
8-(2,6-Difluoro-phenyl)-2-(2-hydroxy-1-hydroxymethyl-ethylamino)-4-(4-methoxyphenyl)-8H-pyrido[2,3-d]pyrimidin-7-one
8-(2,6-Difluoro-phenyl)-2-(2-hydroxy-1-hydroxymethyl-ethylamino)-4-(3-methoxyphenyl)-8H-pyrido[2,3-d]pyrimidin-7-one
8-(2,6-Difluoro-phenyl)-2-(2-hydroxy-1-hydroxymethyl-ethylamino)-4-phenyl-8H-pyrido[2,3-d]pyrimidin-7-one
8-(2,6-Difluoro-phenyl)-2-(2-hydroxy-1-hydroxymethyl-ethylamino)-4-(4-methylthiophenyl)-8H-pyrido[2,3-d]pyrimidin-7-one
8-(2,6-Difluoro-phenyl)-2-(2-hydroxy-1-hydroxymethyl-ethylamino)-4-(2-methoxyphenyl)-8H-pyrido[2,3-d]pyrimidin-7-one
8-(2,6-Difluoro-phenyl)-2-(2-hydroxy-1-hydroxymethyl-ethylamino)-4-(2-hydroxylphenyl)-8H-pyrido[2,3-d]pyrimidin-7-one
8-(2,6-Difluoro-phenyl)-2-(2-hydroxy-1-hydroxymethyl-ethylamino)-4-(3-hydroxylphenyl)-8H-pyrido[2,3-d]pyrimidin-7-one 8-(2,6-Difluoro-phenyl)-2-(2-hydroxy-1-hydroxymethyl-ethylamino)-4-(4-hydroxylphenyl)-8H-pyrido[2,3-d]pyrimidin-7-one 8-(2,6-Difluoro-phenyl)-2-(2-hydroxy-1-hydroxymethyl-ethylamino)-4-(4-methylsulfonylphenyl)-8H-pyrido[2,3-d]-pyrimidin-7-one 8-(2,6-Difluoro-phenyl)-2-(2-hydroxy-1-hydroxymethyl-ethylamino)-4-(3-methylsulfonylphenyl)-8H-pyrido[2,3-d]-pyrimidin-7-one 8-(2,6-Difluoro-phenyl)-2-(2-hydroxy-1-hydroxymethyl-ethylamino)-4-(2-methylsulfonylphenyl)-8H-pyrido[2,3-d]pyrimidin-7-one 8-(2,6-Difluoro-phenyl)-4-(4-fluoro-2-methyl-phenyl)-2-(2-hydroxy-1-hydroxymethyl-ethylamino)-8H-pyrido[2,3-d]pyrimidin-7-one 3-{8-(2,6-difluorophenyl)-2-[(1H-imidazol-2-ylmethyl)amino]-7-oxo-7,8-dihydropyrido[2,3-d]pyrimidin-4-yl}-4-methyl-N-1,3-thiazol-2-ylbenzamide 3-{2-{[3-(diethylamino)propyl]amino}-8-(2,6-difluorophenyl)-7-oxo-5,6,7,8-tetrahydropyrimido[4,5-d]pyrimidin-4-yl]-4-methyl-N-propylbenzamide; or a pharmaceutically acceptable salt, solvate or physiologically functional derivative thereof.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an Ar atmosphere where necessary.

| List of Abbreviations | |
|---|---|
| EDC: 1-(3-Dimethylaminopropyl)-3-ethylcarbodiimide hydrochloride | dppf: 1,1'-Bis(diphenylphosphino)-ferrocene |
| DMAP: 4-(Dimethylamino)pyridine | DMSO: Dimethylsulfoxide |
| m-CPBA: 3-Chlorobenzenecarboperoxoic acid | EtOAc: Ethyl acetate |
| THF: Tetrahydrofuran | DIPEA or DIEA: N,N-Diisopropylethylamine |
| DCM: Dichloromethane | SPE: Solid phase extraction |
| TFA: Trifluoroacetic anhydride | MDAP: Mass directed auto preparation |
| HATU: O-(7-Azabenzotriazol-1-yl)-N,N,N',N'-tetramethyluronium hexafluorophosphate | HBTU: O-Benzotriazol-1-yl-N,N,N',N'-tetramethyluronium hexafluorophosphate |
| NIS: N-Iodosuccinimide | HOBT: 1-Hydroxybenzotriazole hydrate |
| DMF: N,N-Dimethylformamide | HPLC: High Pressure Liquid Chromatography |
| IPA: isopropyl alcohol | M: molar |
| DSC: differential scanning calorimetry | mmol: millimoles |
| L: liters | mol: moles |
| mL: milliliters | aq: aqueous |
| mg: milligrams | eq: equivalents |
| g: grams | h: hours |
| rt: room temperature | mp: melting point |
| eq: equivalents | min: minutes |
| dppf = 1,1'-bis(diphenylphosphino)ferrocene | satd: saturated |
| NMP = 1-methyl-2-pyrrolidinone | |

LC-MS Experimental Conditions:

| Liquid Chromatograph | |
|---|---|
| System: | Shimadzu LC system with SCL-10A Controller and dual UV detector |
| Autosampler: | Leap CTC with a Valco six port injector |
| Column: | Aquasil/Aquasil (C18 40 × 1 mm) |
| Inj. Vol. (uL): | 2.0 |
| Solvent A: | H$_2$O, 0.02% TFA |
| Solvent B: | MeCN, 0.018% TFA |
| Gradient: | linear |
| Channel A: | UV 214 nm |
| Channel B: | ELS |

| Step | Time (min) | Dura. (min) | Flow (μL/min) | Sol. A | Sol. B |
|---|---|---|---|---|---|
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

| | |
|---|---|
| Mass Spectrometer: | PE Sciex Single Quadrupole LC/MS API-150 |
| Polarity: | Positive |
| Acquisition mode: | Profile |

General Procedures

Nuclear magnetic resonance spectra were recorded at 400 MHz using on a Bruker AC 400 spectrometer. CDCl$_3$ is deuteriochloroform, DMSO-d$_6$ is hexadeuteriodimethylsulfoxide, and CD$_3$OD (or MeOD) is tetradeuteriomethanol. Chemical shifts are reported in parts per million (δ) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on a instruments, using electrospray (ES) ionization techniques. All temperatures are reported in degrees Celsius. Other abbreviations are as described in the ACS Style Guide (American Chemical Society, Washington, D.C., 1986).

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative hplc were performed using a Gilson Preparative System using a Luna 5 u C18(2) 100A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a prepacked SiO$_2$ column, a detector with UV wavelength at 254 nm and mixed solvents.

Heating of reaction mixtures with microwave irradiations was carried out on either a Smith Creator (purchased from Personal Chemistry, Forboro/Mass., now owned by Biotage), a Emrys Optimizer (purchased from Personal Chemistry) or an Explorer (provided by CEM Discover, Matthews/N.C.) microwave.

Example 1

4-Chloro-2-methylsulfanyl-8-(4-trifluoromethyl-phenyl)-8H-pyrido[2,3-d]pyrimidin-7-one

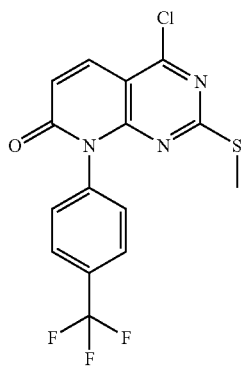

A solution of 4,6-dichloro-2-methylsulfanyl-pyrimidine-5-carbaldehyde (1.0 g, 4.5 mmol) and Et₃N (1.26 mL, 9.0 mmol) in THF (25 mL) was mixed with 4-trifluoromethylaniline (0.62 mL, 4.9 mmol). The resultant mixture was stirred at room temperature for 2 hours before bis(2,2,2-trifluoroethyl)(methoxycarbonylmethyl)-phosphonate (0.95 mL, 4.5 mmol) was added. After stirring at room temperature for additional 12 hours, the mixture was diluted with dichloromethane (50 mL) and washed with H$_2$O (2×25 mL). The organic layer was dried over Na$_2$SO$_4$, filtered and concentrated. This crude product was further purified by washing with a mixture of THF/Hexane (1:3, 2>10 mL) to provide the title compound (1.17 g, 70%): MS (ES) m/z 372 (M+H)$^+$; $^1$H-NMR(CDCl$_3$) δ 2.18 (s, 3H), 6.79 (d, J=9.8 Hz, 1H), 7.40 (d, J=8.4 Hz, 2H), 7.83 (d, J=8.4 Hz, 2H), 8.03 (d, J=9.8 Hz, 1H).

Example 2

4-Chloro-2-methylsulfanyl-8-(2,4-difluoro-phenyl)-8H-pyrido[2,3-d]pyrimidin-7-one

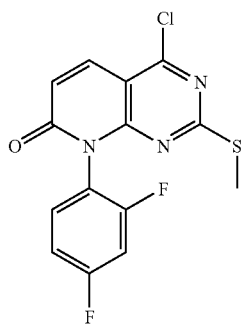

A solution of 4,6-dichloro-2-methylsulfanyl-pyrimidine-5-carbaldehyde (1.0 g, 4.5 mmol) and Et₃N (1.26 mL, 9.0 mmol) in THF (25 mL) was mixed with 2,4-difluoroaniline (0.50 mL, 4.9 mmol). The resultant mixture was stirred at room temperature for 2 hours before bis(2,2,2-trifluoroethyl)(methoxycarbonyl-methyl)phosphonate (0.95 mL, 4.5 mmol) was added. After stirring at room temperature for additional 48 hours, the mixture was diluted with dichloromethane (50 mL) and then washed with H$_2$O (2×25 mL). The organic layer was dried over Na$_2$SO$_4$, filtered and concentrated. This crude product was applied to flash chromatography (EtOAc/Hexane, 1:5) to provide the title compound (0.79 g, 52%): MS (ES) m/z 340 (M+H)$^+$; $^1$H-NMR(CDCl$_3$) δ 2.24 (s, 3H), 6.79 (d, J=9.8 Hz, 1H), 7.06 (m, 2H), 7.29 (m, 1H), 8.03 (d, J=9.8 Hz, 1H).

Example 3

4-Chloro-2-methylsulfanyl-8-(2,6-difluoro-phenyl)-8H-pyrido[2,3-d]pyrimidin-7-one

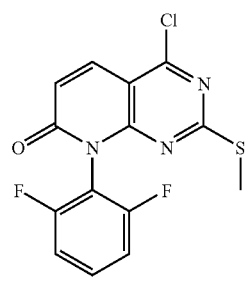

A solution of 4-Chloro-6-(2,6-difluoro-phenylamino)-2-methylsulfanyl-pyrimidine-5-carbaldehyde (200 mg, 0.63 mmol) in DMF (4.0 mL) and Ac$_2$O (2.0 mL) was heated with "Smith Creator" (microwave, 160° C.) for 30 minutes. The mixture was concentrate under vacuum. Flash chromatography (EtOAc/Hexane, 1:5) then provided the title compound (50%): MS (ES) m/z 340 (M+H)$^+$; $^1$H-NMR(CDCl$_3$) δ 2.24 (s, 3H), 6.80 (d, J=9.8 Hz, 1H), 7.12 (m, 2H), 7.49 (m, 1H), 8.04 (d, J=9.8 Hz, 1H).

Example 4

4-Chloro-2-methylsulfinyl-8-(4-trifluoromethyl-phenyl)-8H-pyrido[2,3-d]pyrimidin-7-one

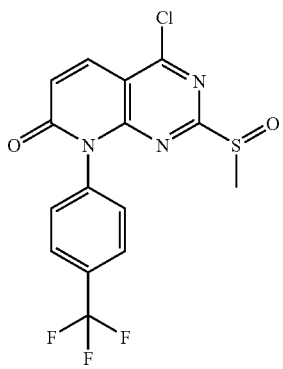

A solution of 4-Chloro-2-methylsulfanyl-8-(4-trifluoromethyl-phenyl)-8H-pyrido[2,3-d]pyrimidin-7-one (1.0 g, 2.7 mmol) in dichloromethane (50 mL) was mixed with m-CPBA (0.63 g, 4.0 mmol). The resultant mixture was stirred at room temperature for 10 minutes and concentrated under vacuum. Flash chromatography (EtOAc/Hexane, 3:1) then provided the title compound (0.86 g, 82%): MS (ES) m/z 388 (M+H)$^+$;

$^1$H-NMR(CDCl$_3$) δ 2.80 (s, 3H), 7.03 (d, J=9.9 Hz, 1H), 7.39 (d, J=8.0 Hz, 2H), 7.86 (d, J=8.0 Hz, 2H), 8.19 (d, J=9.9 Hz, 1H).

Example 5

4-Chloro-2-methylsulfinyl-8-(2,4-difluoro-phenyl)-8H-pyrido[2,3-d]pyrimidin-7-one

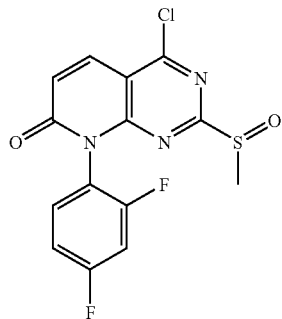

A solution of 4-Chloro-2-methylsulfanyl-8-(2,4-difluoro-phenyl)-8H-pyrido[2,3-d]pyrimidin-7-one (1.0 g, 2.9 mmol) in dichloromethane (50 mL) was mixed with m-CPBA (0.69 g, 4.4 mmol). The resultant mixture was stirred at room temperature for 10 minutes and concentrated under vacou. Flash chromatography (EtOAc/Hexane, 3:1) then provided the title compound (1.02 g, 97%): MS (ES) m/z 356 (M+H)$^+$; $^1$H-NMR(CDCl$_3$) δ 2.84 (m, 3H), 7.01 (d, J=9.9 Hz, 1H), 7.09 (m, 2H), 7.29 (m, 1H), 8.16 (d, J=9.9 Hz, 1H).

Example 6

4-Chloro-2-methylsulfinyl-8-(2,6-difluoro-phenyl)-8H-pyrido[2,3-d]pyrimidin-7-one

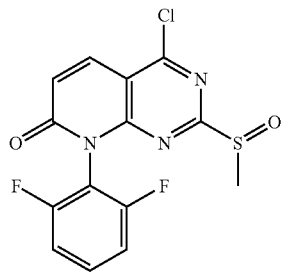

A solution of 4-Chloro-2-methylsulfanyl-8-(2,6-difluoro-phenyl)-8H-pyrido[2,3-d]pyrimidin-7-one (1.0 g, 2.9 mmol) in dichloromethane (50 mL) was mixed with m-CPBA (0.69 g, 4.4 mmol). The resultant mixture was stirred at room temperature for 10 minutes and concentrated under vacou. Flash chromatography (EtOAc/Hexane, 3:1) then provided the title compound (0.91 g, 87%): MS (ES) m/z 356 (M+H)$^+$; $^1$H-NMR(CDCl$_3$) δ 2.85 (s, 3H), 7.03 (d, J=9.6 Hz, 1H), 7.15 (m, 2H) 7.53 (m, 1H), 8.18 (d, J=9.6 Hz, 1H).

Example 7

4-Chloro-2-(2-hydroxy-1-hydroxymethyl-ethylamino)-8-(4-trifluoromethyl-phenyl)-8H-pyrido[2,3-d]pyrimidin-7-one

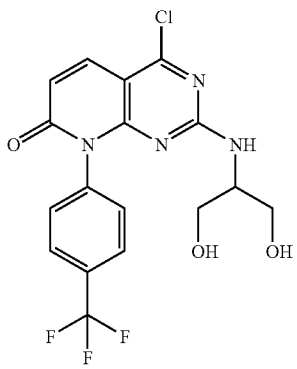

A solution of 4-Chloro-2-methylsulfinyl-8-(4-trifluoromethyl-phenyl)-8H-pyrido[2,3-d]pyrimidin-7-one (0.29 g, 0.75 mmol) in dichloromethane (30 mL) was mixed with a solution of serinol (0.075 g, 0.82 mmol) in DMF (0.75 mL). The resultant mixture was stirred at room temperature for 1 hour before concentrated under vacuum. Flash chromatography (EtOAc:Hexane, 3:1) then provided the title compound (0.14 g, 45%): MS (ES) m/z 415 (M+H)$^+$; $^1$H-NMR(CDCl$_3$) δ 2.25 (s, br, 2H), 3.66 (m, br, 5H), 6.15 (m, br, 1H), 6.55 (d, J=9.2 Hz, 1H), 7.36 (m, 2H), 7.81 (d, J=8.1 Hz, 2H), 7.92 (d, J=9.2 Hz, 1H).

Example 8

4-Chloro-2-(2-hydroxy-1-hydroxymethyl-ethylamino)-8-(2,4-difluoro-phenyl)-8H-pyrido[2,3-d]pyrimidin-7-one

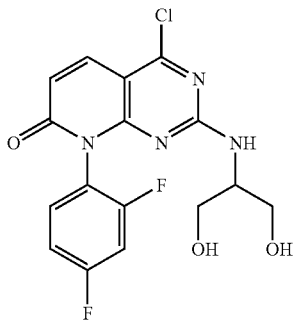

A solution of 4-Chloro-2-methylsulfinyl-8-(2,4-difluoro-phenyl)-8H-pyrido[2,3-d]pyrimidin-7-one (0.24 g, 0.67 mmol) in dichloromethane (24 mL) was mixed with a solution of serinol (0.065 g, 0.71 mmol) in DMF (0.65 mL). The resultant mixture was stirred at room temperature for 1 hour before concentrated under vacuum. Flash chromatography (EtOAc/Hexane, 3:1) then provided the title compound (0.12 g, 46%): MS (ES) m/z 383 (M+H)$^+$; $^1$H-NMR(CDCl$_3$) δ 2.15 (s, br, 2H), 3.75 (m, br, 5H), 6.10 (m, br, 1H), 6.55 (m, 1H), 7.04 (m, 2H), 7.28 (m, 1H), 7.90 (m, 1H).

Example 9

4-Chloro-2-(2-hydroxy-1-hydroxymethyl-ethylamino)-8-(2,6-difluoro-phenyl)-8H-pyrido[2,3-d]pyrimidin-7-one

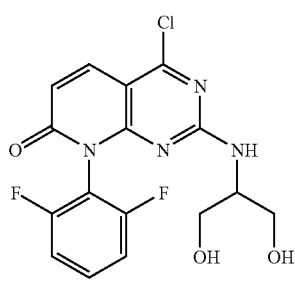

A solution of 4-Chloro-2-methylsulfinyl-8-(2,6-difluoro-phenyl)-8H-pyrido[2,3-d]pyrimidin-7-one (0.90 g, 2.53 mmol) in dichloromethane (90 mL) was mixed with a solution of serinol (0.24 g, 2.66 mmol) in DMF (2.0 mL). The resultant mixture was stirred at room temperature for 1 hour before concentrated under vacuum. Flash chromatography (EtOAc/Hexane, 3:1) then provided the title compound (0.40 g, 42%): MS (ES) m/z 383 (M+H)+; $^1$H-NMR(CDCl$_3$) δ 1.95 (s, br, 2H), 3.90 (m, br, 5H), 6.05 (m, br, 1H), 6.56 (d, J=9.6 Hz, 1H), 7.10 (m, 2H), 7.48 (d, J=8.1 Hz, 2H), 7.94 (d, J=9.6 Hz, 1H).

Example 10

4-(2-Methylsulfanyl-phenyl)-2-(2-hydroxy-1-hydroxymethyl-ethylamino)-8-(4-trifluoromethyl-phenyl)-8H-pyrido[2,3-d]pyrimidin-7-one

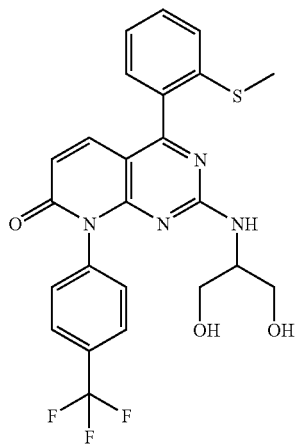

A solution of 4-Chloro-2-(2-hydroxy-1-hydroxymethyl-ethylamino)-8-(4-trifluoromethyl-phenyl)-8H-pyrido[2,3-d]pyrimidin-7-one (50 mg, 0.12 mmol) in dioxane/H$_2$O (3:1, 4.8 mL) was mixed with 2-methylthiophenyl boronic acid (30.4 mg, 0.18 mmol) and K$_2$CO$_3$ (50.1 mg, 0.36 mmol). The resultant mixture was bubbled with argon for 5 minutes, and added by Pd(PPh$_3$)$_4$ (2.8 mg, 0.0024 mmol). The reaction tube was sealed and heated with "Smith Creator" (microwave, 150° C.) for 15 minutes. The mixture was concentrated under vaco. Flash chromatography (EtOAc/Hexane, 3:1) then provided the title compound (88%): MS (ES) m/z 503 (M+H)+; $^1$H-NMR(CDCl$_3$) δ 2.48 (s, 3H), 2.65 (s, br, 2H), 3.70 (m, br, 5H), 6.20 (m, br, 1H), 6.45 (m, 1H), 7.43 (m, 6H), 7.68 (m, 1H), 7.83 (m, 2H).

Example 11

4-(3-Methylsulfanyl-phenyl)-2-(2-hydroxy-1-hydroxymethyl-ethylamino)-8-(4-trifluoromethyl-phenyl)-8H-pyrido[2,3-d]pyrimidin-7-one

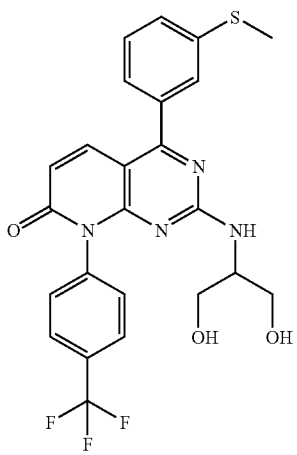

The title compound was prepared by following the procedure in Example 10 except 3-methylthiophenyl boronic acid was used in the coupling step (76%): MS (ES) m/z 503 (M+H)+; $^1$H-NMR(CDCl$_3$) δ 2.49 (s, br, 2H), 2.54 (s, 3H), 3.68 (m, br, 5H), 5.90 (s, br, 1H), 6.47 (s, b, 1H), 7.45 (m, 6H), 7.65 (m, 1H), 7.82 (m, 2H).

Example 12

4-(4-Methylsulfanyl-phenyl)-2-(2-hydroxy-1-hydroxymethyl-ethylamino)-8-(4-trifluoromethyl-phenyl)-8H-pyrido[2,3-d]pyrimidin-7-one

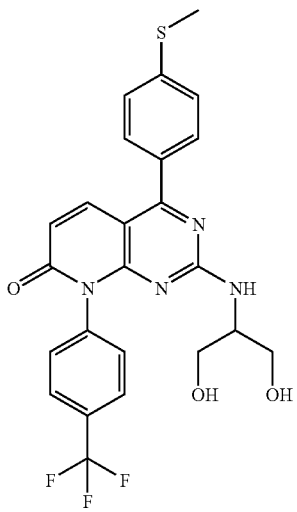

The title compound was prepared by following the procedure in Example 10 except 4-methylthiophenyl boronic acid was used in the coupling step (56%): MS (ES) m/z 503 (M+H)⁺; ¹H-NMR(CDCl₃) δ 2.40 (s, br, 2H), 2.58 (s, 3H), 3.69 (m, br, 5H), 5.85 (s, br, 1H), 6.48 (m, 1H), 7.40 (m, 2H), 7.48 (m, 2H), 7.56 (m, 2H), 7.67 (m, 1H), 7.83 (m, 2H).

Example 13

4-phenyl-2-(2-hydroxy-1-hydroxymethyl-ethylamino)-8-(4-trifluoromethyl-phenyl)-8H-pyrido[2,3-d]pyrimidin-7-one

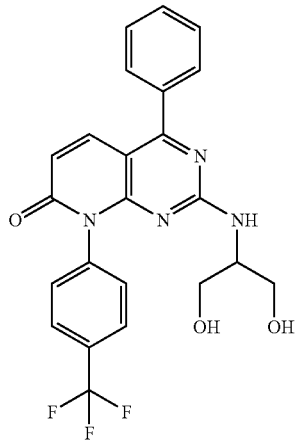

The title compound was prepared by following the procedure in Example 10 except phenyl boronic acid was used in the coupling step (82%): MS (ES) m/z 457 (M+H)⁺; ¹H-NMR (CDCl₃) δ 1.81 (s, br, 2H), 3.68 (m, br, 5H), 6.10 (m, br, 1H), 6.47 (m, 1H), 7.40 (m, 2H), 7.59 (m, 5H), 7.82 (m, 3H).

Example 14

4-(3-chlorophenyl)-2-(2-hydroxy-1-hydroxymethyl-ethylamino)-8-(4-trifluoromethyl-phenyl)-8H-pyrido[2,3-d]pyrimidin-7-one

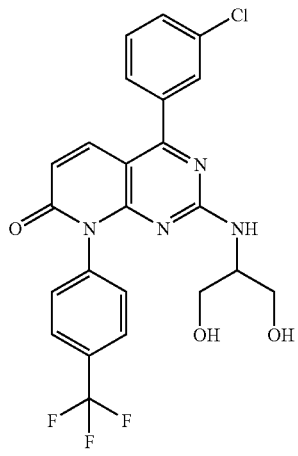

The title compound was prepared by following the procedure in Example 10 except 3-chlorohenyl boronic acid was used in the coupling step (76%): MS (ES) m/z 491 (M+H)⁺; ¹H-NMR(CDCl₃) δ 1.66 (s, br, 2H), 3.73 (m, br, 5H), 6.15 (m, br, 1H), 6.50 (m, 1H), 7.52 (m, 6H), 7.75 (m, 1H), 7.84 (m, 2H).

Example 15

4-(4-chlorophenyl)-2-(2-hydroxy-1-hydroxymethylethylamino)-8-(4-trifluoromethyl-phenyl)-8H-pyrido[2,3-d]pyrimidin-7-one

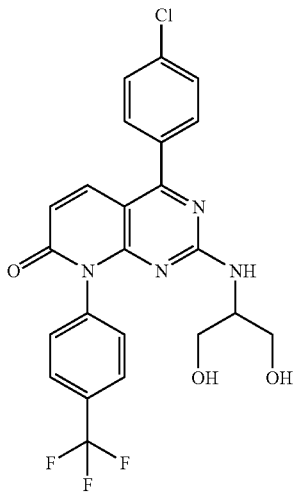

The title compound was prepared by following the procedure in Example 10 except 4-chlorohenyl boronic acid was used in the coupling step (72%): MS (ES) m/z 491 (M+H)⁺; ¹H-NMR(CDCl₃) δ 1.61 (s, br, 2H), 3.73 (m, br, 5H), 6.05 (m, br, 1H), 6.50 (m, 1H), 7.41 (m, 2H), 7.58 (m, 4H), 7.76 (m, 1H), 7.84 (m, 2H).

Example 16

4-(3,4-difluorophenyl)-2-(2-hydroxy-1-hydroxymethyl-ethylamino)-8-(4-trifluoromethyl-phenyl)-8H-pyrido[2,3-d]pyrimidin-7-one

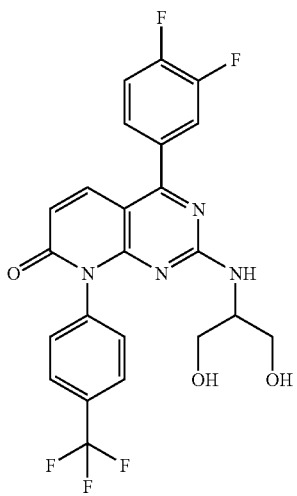

The title compound was prepared by following the procedure in Example 10 except 3,4-difluorophenyl boronic acid was used in the coupling step (65%): MS (ES) m/z 493 (M+H)+; 1H-NMR(CDCl3) δ 2.06 (s, br, 2H), 3.72 (m, br, 5H), 6.05 (m, br, 1H), 6.50 (m, 1H), 7.42 (m, 5H), 7.76 (m, 1H), 7.83 (m, 2H).

Example 17

4-(2-Chlorophenyl)-2-(2-hydroxy-1-hydroxymethyl-ethylamino)-8-(4-trifluoromethyl-phenyl)-8H-pyrido[2,3-d]pyrimidin-7-one

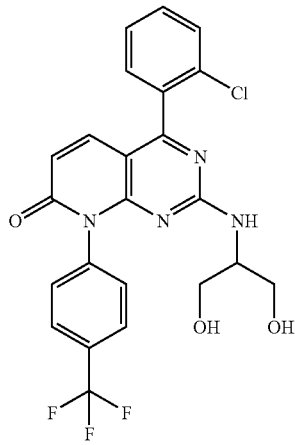

The title compound was prepared by following the procedure in Example 10 except 2-chlorohenyl boronic acid was used in the coupling step (72%). MS (ES) m/z 491 (M+H+; 1H-NMR(CDCl3) δ 3.60 (m, br, 5H), 6.10 (m, br, 1H), 6.45 (m, 1H), 7.32 (m, 2H), 7.50 (m, 5H), 7.80 (m, 2H).

Example 18

4-(4-Methoxyphenyl)-2-(2-hydroxy-1-hydroxymethyl-ethylamino)-8-(4-trifluoromethyl-phenyl)-8H-pyrido[2,3-d]pyrimidin-7-one

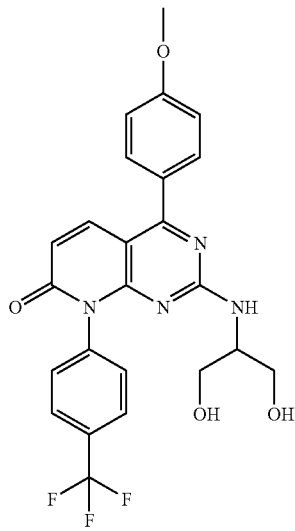

The title compound was prepared by following the procedure in Example 10 except [4-(methyloxy)phenyl]boronic acid was used in the coupling step (66%). MS (ES) m/z 487 (M+H)+; 1H-NMR(CDCl3) δ 1.85 (s, br, 2H), 3.69 (m, br, 5H), 3.92 (s, 3H), 6.10 (m, br, 1H), 6.47 (m, 1H), 7.07 (m, 2H), 7.40 (m, 2H), 7.60 (m, 2H), 7.84 (m, 3H).

Example 19

4-(3-Methoxyphenyl)-2-(2-hydroxy-1-hydroxymethyl-ethyl-ethylamino)-8-(4-trifluoromethyl-phenyl)-8H-pyrido[2,3-d]pyrimidin-7-one

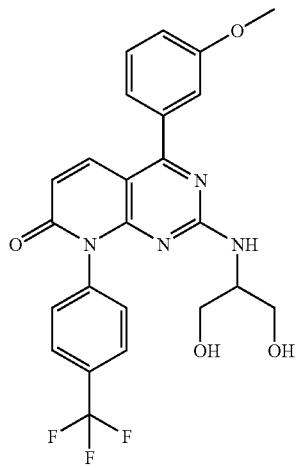

The title compound was prepared by following the procedure in Example 10 except [3-(methyloxy)phenyl]boronic acid was used in the coupling step (65%): MS (ES) m/z 487 (M+H)+; 1H-NMR(CDCl3) δ 2.90 (s, br, 2H), 3.61 (m, br, 5H), 3.88 (s, 3H), 6.05 (m, br, 1H), 6.45 (m, 1H), 7.09 (m, 2H), 7.45 (m, 4H), 7.80 (m, 3H).

Example 20

4-(2-Methoxyphenyl)-2-(2-hydroxy-1-hydroxymethyl-ethylamino)-8-(4-trifluoromethyl-phenyl)-8H-pyrido[2,3-d]pyrimidin-7-one

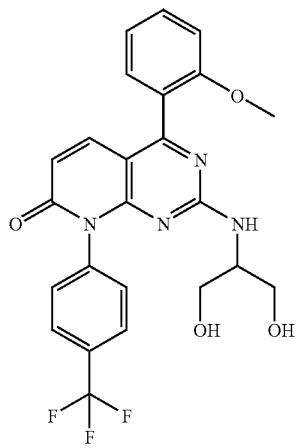

The title compound was prepared by following the procedure in Example 10 except [2-(methyloxy)phenyl]boronic acid was used in the coupling step (75%): MS (ES) m/z 487 (M+H)+; 1H-NMR(CDCl3) δ 2.20 (s, br, 2H), 3.69 (m, br, 5H), 3.84 (s, 3H), 6.05 (m, br, 1H), 6.41 (m, 1H), 7.12 (m, 2H), 7.47 (m, 5H), 7.83 (m, 2H).

Example 21

4-(3-Methylsulfanyl-phenyl)-2-(2-hydroxy-1-hydroxymethyl-ethylamino)-8-(2,4-difluorophenyl)-8H-pyrido[2,3-d]pyrimidin-7-one

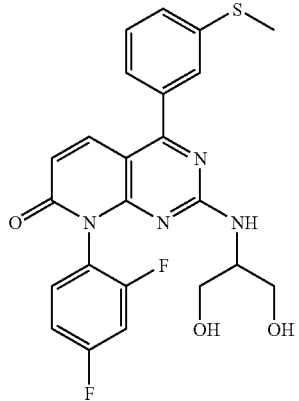

A solution of 4-Chloro-2-(2-hydroxy-1-hydroxymethyl-ethylamino)-8-(2, 4-difluoro-phenyl)-8H-pyrido[2,3-d]pyrimidin-7-one (50 mg, 0.13 mmol) in dioxane/H2O (3:1, 4.8 mL) was mixed with 3-methylthiophenyl boronic acid (33.8 mg, 0.20 mmol) and K2CO3 (54.3 mg, 0.39 mmol). The resultant mixture was bubbled with argon for 5 minutes followed by the addition of Pd(PPh3)4 (3.0 mg, 0.0026 mmol). The reaction tube was sealed and heated with "Smith Creator" (microwave, 150° C.) for 15 minutes. The mixture was concentrated under vaco. Flash chromatography (EtOAc/Hexane, 3:1) then provided the title compound (90%): MS (ES) m/z 471 (M+H)+; 1H-NMR(CDCl3) δ 2.40 (s, br, 2H), 2.40 (s, 3H), 3.90 (m, br, 5H), 6.00 (m, br, 1H), 6.45 (m, 1H), 7.15 (m, 2H), 7.40 (m, 5H), 7.85 (m, 1H).

Example 22

4-(4-Methylsulfanyl-phenyl)-2-(2-hydroxy-1-hydroxymethyl-ethylamino)-8-(2,4-difluorophenyl)-8H-pyrido[2,3-d]pyrimidin-7-one

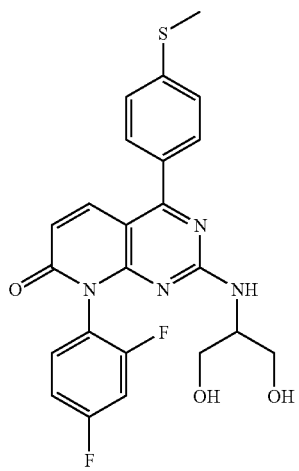

The title compound was prepared by following the procedure in Example 21 except 4-methylthiophenyl boronic acid was used in the coupling step (95%): MS (ES) m/z 471 (M+H)+; 1H-NMR(CDCl3) δ 2.35 (s, br, 2H), 2.57 (s, 3H), 3.76 (m, br, 5H), 6.05 (m, br, 1H), 6.46 (m, 1H), 7.05 (m, 2H), 7.27 (m, 1H), 7.39 (m, 2H), 7.55 (m, 2H), 7.81 (m, 1H).

Example 23

4-(2-Methylsulfanyl-phenyl)-2-(2-hydroxy-1-hydroxymethyl-ethylamino)-8-(2,4-difluorophenyl)-8H-pyrido[2,3-d]pyrimidin-7-one

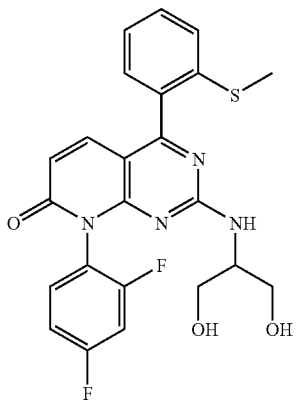

The title compound was prepared by following the procedure in Example 21 except 2-methylthiophenyl boronic acid was used in the coupling step (72%): MS (ES) m/z 471 (M+H)+; 1H-NMR(CDCl3) δ 2.45 (s, 3H), 2.55 (s, br, 2H), 3.72 (m, br, 5H), 6.05 (m, br, 1H), 6.40 (m, 1H), 7.05 (m, 2H), 7.40 (m, 6H).

Example 24

4-(3,4-difluorophenyl)-2-(2-hydroxy-1-hydroxymethyl-ethyl-ethylamino)-8-(2,4-difluorophenyl)-8H-pyrido[2,3-d]pyrimidin-7-one

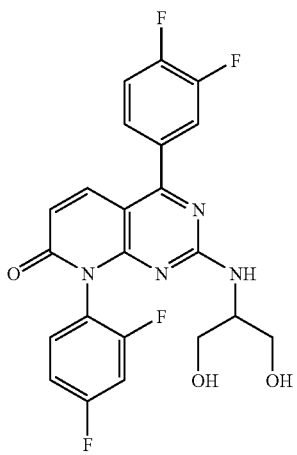

The title compound was prepared by following the procedure in Example 21 except 3,4-difluorophenyl boronic acid was used in the coupling step (56%): MS (ES) m/z 461 (M+H)⁺; ¹H-NMR(CDCl₃) δ 2.25 (s, br, 2H), 3.77 (m, br, 5H), 6.15 (m, br, 1H), 6.48 (m, 1H), 7.06 (m, 2H), 7.49 (m, 4H), 7.74 (m, 1H).

Example 25

4-(2-Methoxyphenyl)-2-(2-hydroxy-1-hydroxymethyl-ethylamino)-8-(2,4-difluorophenyl)-8H-pyrido[2,3-d]pyrimidin-7-one

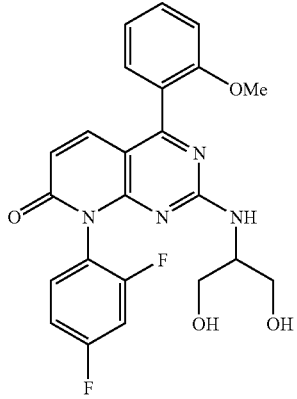

The title compound was prepared by following the procedure in Example 21 except 2-methoxyphenyl boronic acid was used in the coupling step (89%): MS (ES) m/z 455 (M+H)⁺; ¹H-NMR(CDCl₃) δ 2.85 (s, br, 2H), 3.67 (m, br, 5H), 3.81 (s, 3H), 6.10 (m, br, 1H), 6.38 (m, 1H), 7.07 (m, 5H), 7.30 (s, 1H), 7.38 (m, 1H), 7.50 (m, 1H).

Example 26

4-(4-Methoxyphenyl)-2-(2-hydroxy-1-hydroxymethyl-ethylamino)-8-(2,4-difluorophenyl)-8H-pyrido[2,3-d]pyrimidin-7-one

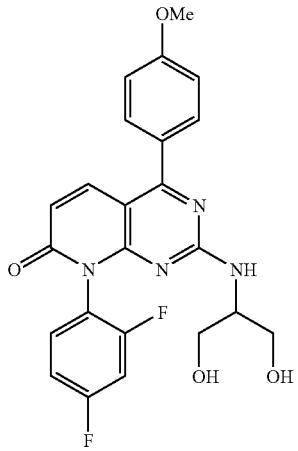

The title compound was prepared by following the procedure in Example 21 except 4-methoxyphenyl boronic acid was used in the coupling step (70%): MS (ES) m/z 455 (M+H)⁺; ¹H-NMR(CDCl₃) δ 2.60 (s, br, 2H), 3.73 (m, br, 5H), 3.91 (s, 3H), 6.15 (m, br, 1H), 6.45 (m, 1H), 7.05 (m, 4H), 7.38 (s, 1H), 7.58 (m, 2H), 7.83 (m, 1H).

Example 27

4-(2-Biphenyl)-2-(2-hydroxy-1-hydroxymethyl-ethylamino)-8-(2,4-difluorophenyl)-8H-pyrido[2,3-d]pyrimidin-7-one

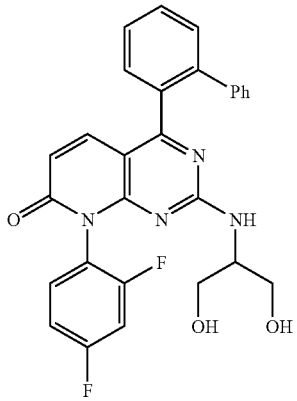

The title compound was prepared by following the procedure in Example 21 except 2-biphenyl boronic acid was used in the coupling step (89%): MS (ES) m/z 501 (M+H)⁺; ¹H-NMR(CDCl₃) δ 2.06 (s, br, 2H), 3.73 (m, br, 5H), 6.15 (m, br, 1H), 6.18 (s, br, 1H), 7.00 (m, 2H), 7.25 (m, 7H), 7.58 (m, 4H).

Example 28

4-(3-Biphenyl)-2-(2-hydroxy-1-hydroxymethyl-ethylamino)-8-(2,4-difluorophenyl)-8H-pyrido[2,3-d]pyrimidin-7-one

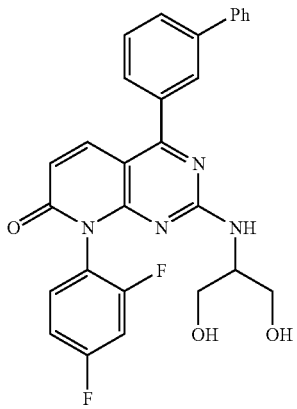

The title compound was prepared by following the procedure in Example 21 except 3-biphenyl boronic acid was used in the coupling step (92%): MS (ES) m/z 501 (M+H)⁺; ¹H-NMR(CDCl₃) δ 2.10 (s, br, 2H), 3.72 (m, br, 5H), 6.10 (m, br, 1H), 6.47 (m, 1H), 7.06 (m, 2H), 7.60 (m, 8H), 7.82 (m, 3H).

Example 29

4-(2-Tolyl)-2-(2-hydroxy-1-hydroxymethyl-ethylamino)-8-(2,4-difluorophenyl)-8H-pyrido[2,3-d]pyrimidin-7-one

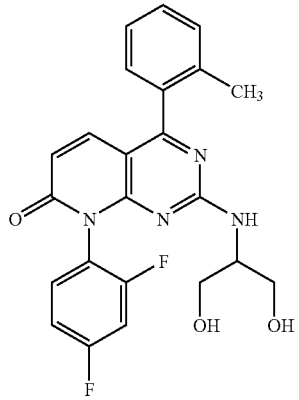

The title compound was prepared by following the procedure in Example 21 except 2-tolyl boronic acid was used in the coupling step (66%): MS (ES) m/z 439 (M+H)+; 1H-NMR (CDCl3) δ 2.24 (s, 3H), 2.96 (s, br, 2H), 3.68 (m, br, 5H), 6.10 (m, br, 1H), 6.39 (m, 1H), 7.04 (m, 2H), 7.40 (m, 6H).

Example 30

4-(3-Fluoro-4-biphenyl)-2-(2-hydroxy-1-hydroxymethyl-ethylamino)-8-(2,4-difluorophenyl)-8H-pyrido[2,3-d]pyrimidin-7-one

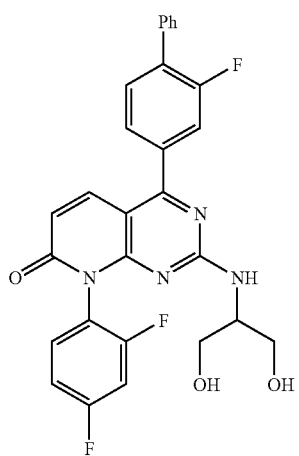

The title compound was prepared by following the procedure in Example 21 except 3-fluoro-4-biphenyl boronic acid was used in the coupling step (48%): MS (ES) m/z 519 (M+H)+; 1H-NMR(CDCl3) δ 2.15 (s, br, 2H), 3.78 (m, br, 5H), 6.05 (m, br, 1H), 6.50 (m, 1H), 7.06 (m, 2H), 7.28 (m, 1H), 7.52 (m, 8H), 7.86 (m, 1H).

Example 31

4-(4-Chlorophenyl)-2-(2-hydroxy-1-hydroxymethyl-ethylamino)-8-(2,4-difluorophenyl)-8H-pyrido[2,3-d]pyrimidin-7-one

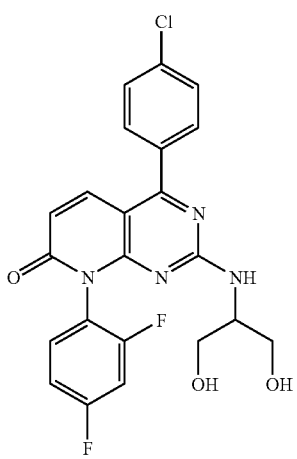

The title compound was prepared by following the procedure in Example 21 except 4-chlorophenyl boronic acid was used in the coupling step (70%): MS (ES) m/z 459 (M+H)+; 1H-NMR(CDCl3) δ 2.83 (s, br, 2H), 3.72 (m, br, 5H), 6.15 (m, br, 1H), 6.46 (m, 1H), 7.04 (m, 2H), 7.28 (m, 1H), 7.53 (m, 4H), 7.72 (m, 1H).

Example 32

4-(3-Chlorophenyl)-2-(2-hydroxy-1-hydroxymethyl-ethylamino)-8-(2,4-difluorophenyl)-8H-pyrido[2,3-d]pyrimidin-7-one

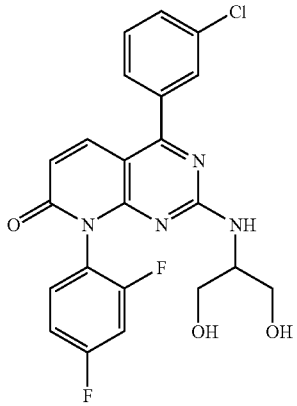

The title compound was prepared by following the procedure in Example 21 except 3-chlorophenyl boronic acid was used in the coupling step (49%). MS (ES) m/z 459 (M+H)+; 1H-NMR(CDCl3) δ 2.55 (s, br, 2H), 3.74 (m, br, 5H), 6.10 (m, br, 1H), 6.47 (m, 1H), 7.05 (m, 2H), 7.28 (m, 1H), 7.53 (m, 4H), 7.73 (m, 1H).

Example 33

4-(3-Fluorophenyl)-2-(2-hydroxy-1-hydroxymethyl-ethylamino)-8-(2,4-difluorophenyl)-8H-pyrido[2,3-d]pyrimidin-7-one

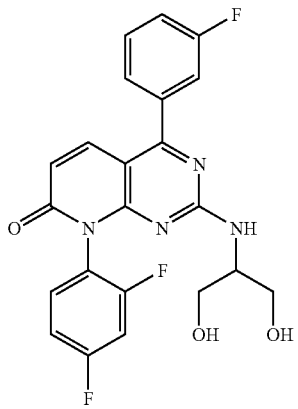

The title compound was prepared by following the procedure in Example 21 except 3-fluorophenyl boronic acid was used in the coupling step (64%): MS (ES) m/z 443 (M+H)$^+$; $^1$H-NMR(CDCl$_3$) δ 2.05 (s, br, 2H), 3.79 (m, br, 5H), 6.10 (m, br, 1H), 6.49 (m, 1H), 7.07 (m, 2H), 7.42 (m, 5H), 7.77 (m, 1H).

Example 34

4-(3-Methoxyphenyl)-2-(2-hydroxy-1-hydroxymethyl-ethylamino)-8-(2,4-difluorophenyl)-8H-pyrido[2,3-d]pyrimidin-7-one

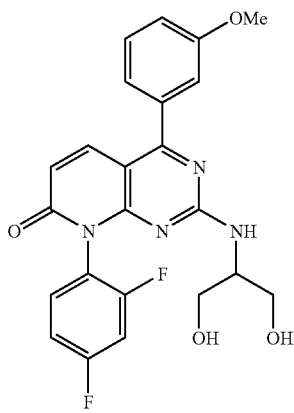

The title compound was prepared by following the procedure in Example 21 except 3-methoxyphenyl boronic acid was used in the coupling step (89%): MS (ES) m/z 455 (M+H)$^+$; $^1$H-NMR(CDCl$_3$) δ 2.07 (s, br, 2H), 3.83 (m, br, 5H), 3.91 (s, 3H), 6.15 (m, br, 1H), 6.47 (m, 1H), 7.10 (m, 5H), 7.28 (m, 1H), 7.47 (m, 1H), 7.82 (m, 1H).

Example 35

4-(3,5-Difluorophenyl)-2-(2-hydroxy-1-hydroxymethyl-ethyl-ethylamino)-8-(2,4-difluorophenyl)-8H-pyrido[2,3-d]pyrimidin-7-one

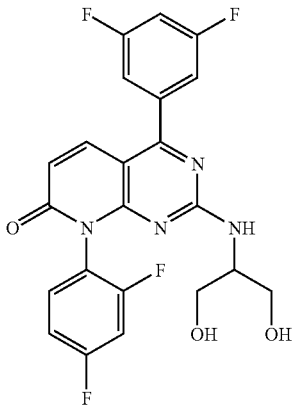

The title compound was prepared by following the procedure in Example 21 except 3,5-difluorophenyl boronic acid was used in the coupling step (89%): MS (ES) m/z 461 (M+H)$^+$; $^1$H-NMR(CDCl$_3$) δ 2.05 (s, br, 2H), 3.89 (m, br, 5H), 6.10 (m, br, 1H), 6.51 (m, 1H), 7.08 (m, 5H), 7.28 (m, 1H), 7.75 (m, 1H).

Example 36

4-(2-Methylsulfanyl-phenyl)-2-(2-hydroxy-1-hydroxymethyl-ethylamino)-8-(2,6-difluorophenyl)-8H-pyrido[2,3-d]pyrimidin-7-one

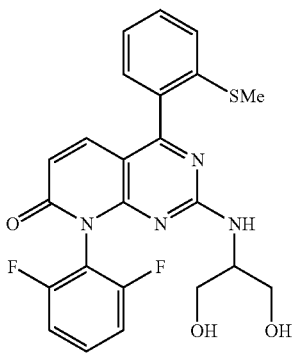

A solution of 4-Chloro-2-(2-hydroxy-1-hydroxymethyl-ethylamino)-8-(2,6-difluoro-phenyl)-8H-pyrido[2,3-d]pyrimidin-7-one (50 mg, 0.13 mmol) in dioxane/H$_2$O (3:1, 4.8 mL) was mixed with 2-methylthiophenyl boronic acid (33.8 mg, 0.20 mmol) and K$_2$CO$_3$ (54.3 mg, 0.39 mmol). The resultant mixture was bubbled with argon for 5 minutes, and added by Pd(PPh$_3$)$_4$ (3.0 mg, 0.0026 mmol). The reaction tube was sealed and heated with "Smith Creator" (microwave, 150° C.) for 15 minutes. The mixture was concentrated under vaco. Flash chromatography (EtOAc/Hexane, 3:1) then provided the title compound (89%): MS (ES) m/z 471 (M+H)$^+$; $^1$H-NMR(CDCl$_3$) δ 2.45 (s, 3H), 2.55 (s, br, 2H), 3.72 (m, br, 5H), 6.25 (m, br, 1H), 6.41 (m, 1H), 7.11 (m, 2H), 7.30 (m, 2H), 7.45 (m, 2H), 7.51 (m, 2H).

Example 37

4-(3-Methylsulfanyl-phenyl)-2-(2-hydroxy-1-hydroxymethyl-ethylamino)-8-(2,6-difluorophenyl)-8H-pyrido[2,3-d]pyrimidin-7-one

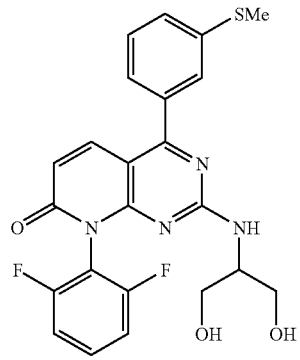

The title compound was prepared by following the procedure in Example 36 except 3-methylthiophenyl boronic acid was used in the coupling step (71%): MS (ES) m/z 471 (M+H)+; 1H-NMR(CDCl3) δ 2.50 (s, br, 2H), 2.55 (s, 3H), 3.72 (m, br, 5H), 6.25 (m, br, 1H), 6.47 (m, 1H), 7.11 (m, 2H), 7.35 (m, 1H), 7.46 (m, 4H), 7.77 (m, 1H).

Example 38

4-(4-Methoxyphenyl)-2-(2-hydroxy-1-hydroxymethyl-ethylamino)-8-(2,6-difluorophenyl)-8H-pyrido[2,3-d]pyrimidin-7-one

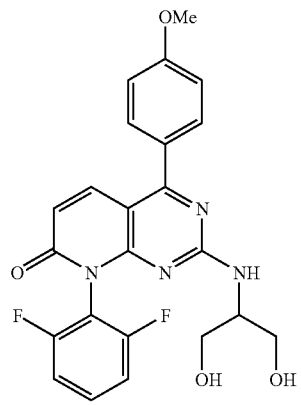

The title compound was prepared by following the procedure in Example 36 except 4-methoxyphenyl boronic acid was used in the coupling step (70%): MS (ES) m/z 455 (M+H)+; 1H-NMR(CDCl3) δ 1.80 (s, br, 2H), 3.77 (m, br, 5H), 3.92 (s, 3H), 6.10 (m, br, 1H), 6.47 (m, 1H), 7.12 (m, 4H), 7.50 (m, 1H), 7.62 (m, 2H), 7.86 (m, 1H).

Example 39

4-(3-Methoxyphenyl)-2-(2-hydroxy-1-hydroxymethyl-ethylamino)-8-(2,6-difluorophenyl)-8H-pyrido[2,3-d]pyrimidin-7-one

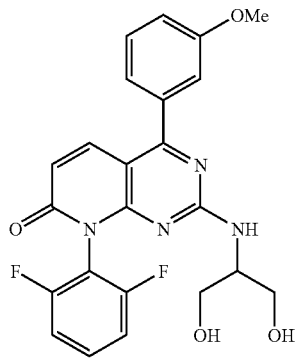

The title compound was prepared by following the procedure in Example 36 except 3-methoxyphenyl boronic acid was used in the coupling step (79%): MS (ES) m/z 455 (M+H)+; 1H-NMR(CDCl3) δ 2.25 (s, br, 2H), 3.75 (m, br, 5H), 3.90 (s, 3H), 6.15 (m, br, 1H), 6.46 (m, 1H), 7.15 (m, 5H), 7.47 (m, 2H), 7.82 (m, 1H).

Example 40

4-phenyl-2-(2-hydroxy-1-hydroxymethyl-ethylamino)-8-(2,6-difluorophenyl)-8H-pyrido[2,3-d]pyrimidin-7-one

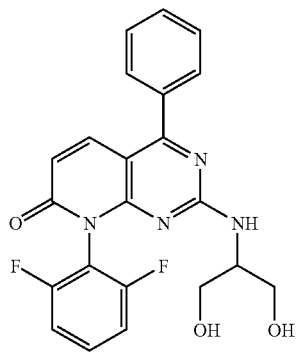

The title compound was prepared by following the procedure in Example 36 except phenyl boronic acid was used in the coupling step (89%): MS (ES) m/z 425 (M+H)+; 1H-NMR (CDCl3) δ 2.16 (s, br, 2H), 3.83 (m, br, 5H), 6.15 (m, br, 1H), 6.47 (m, 1H), 7.13 (m, 2H), 7.55 (m, 6H), 7.80 (m, 1H).

Example 41

4-(4-Methylsulfanyl-phenyl)-2-(2-hydroxy-1-hydroxymethyl-ethylamino)-8-(2,6-difluorophenyl)-8H-pyrido[2,3-d]pyrimidin-7-one

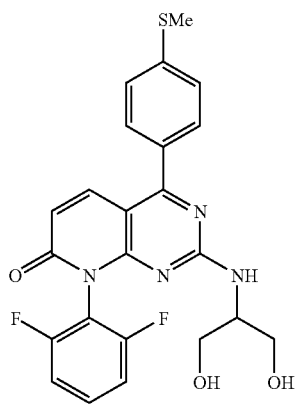

The title compound was prepared by following the procedure in Example 36 except 4-methylthiophenyl boronic acid was used in the coupling step (67%): MS (ES) m/z 471 (M+H)$^+$; $^1$H-NMR(CDCl$_3$) δ 2.50 (s, 3H), 2.57 (s, br, 2H), 3.72 (m, br, 5H), 6.20 (m, br, 1H), 6.46 (m, 1H), 7.11 (m, 2H), 7.39 (m, 2H), 7.45 (m, 1H), 7.56 (m, 2H), 7.81 (m, 1H).

Example 42

4-(2-Methoxyphenyl)-2-(2-hydroxy-1-hydroxymethyl-ethylamino)-8-(2,6-difluorophenyl)-8H-pyrido[2,3-d]pyrimidin-7-one

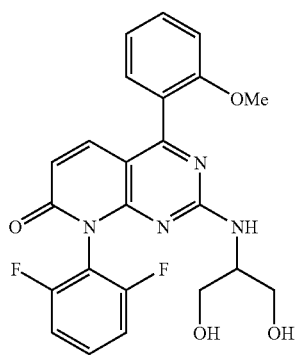

The title compound was prepared by following the procedure in Example 36 except 2-methoxyphenyl boronic acid was used in the coupling step (91%): MS (ES) m/z 455 (M+H)$^+$; $^1$H-NMR(CDCl$_3$) δ 2.70 (s, br, 2H), 3.68 (m, br, 5H), 3.82 (s, 3H), 6.20 (m, br, 1H), 6.40 (m, 1H), 7.08 (m, 4H), 7.48 (m, 4H).

Example 43

4-(2-Hydroxyphenyl)-2-(2-hydroxy-1-hydroxymethyl-ethyl-ethylamino)-8-(2,6-difluorophenyl)-8H-pyrido[2,3-d]pyrimidin-7-one

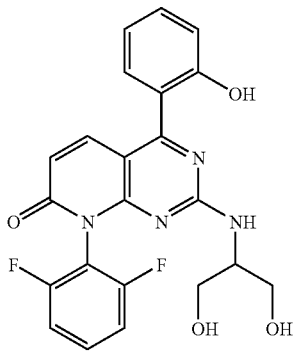

A solution of 4-Chloro-2-(2-hydroxy-1-hydroxymethyl-ethylamino)-8-(2,6-difluoro-phenyl)-8H-pyrido[2,3-d]pyrimidin-7-one (50 mg, 0.13 mmol) in dioxane/H$_2$O (3:1, 4.8 mL) was mixed with 2-(4,4,5,5-tetramethyl-1,3,2-dioxaborolan-2-yl)phenol (44.0 mg, 0.20 mmol) and K$_2$CO$_3$ (71.9 mg, 0.52 mmol). The resultant mixture was bubbled with argon for 5 minutes, and added by Pd(PPh$_3$)$_4$ (3.0 mg, 0.0026 mmol). The reaction tube was sealed and heated with "Smith Creator" (microwave, 150° C.) for 15 minutes. The mixture was concentrated under vaco. Flash chromatography (EtOAc/Hexane, 3:1) then afforded the title compound (82%): MS (ES) m/z 441 (M+H)$^+$; $^1$H-NMR(CDCl$_3$) δ 1.65 (s, br, 2H), 3.80 (m, br, 5H), 6.05 (m, br, 1H), 6.54 (m, 1H), 7.15 (m, 4H), 7.48 (m, 3H), 7.98 (m, 1H).

Example 44

4-(3-Hydroxyphenyl)-2-(2-hydroxy-1-hydroxymethyl-ethyl-ethylamino)-8-(2,6-difluorophenyl)-8H-pyrido[2,3-d]pyrimidin-7-one

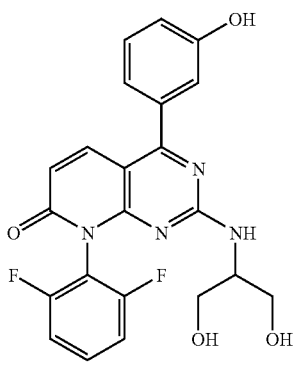

The title compound was prepared by following the procedure in Example 43 except 3-(4,4,5,5-tetramethyl-1,3,2-dioxaborolan-2-yl)phenol was used in the coupling step (13%): MS (ES) m/z 441 (M+H)$^+$; $^1$H-NMR-(CD$_3$OD) δ 2.18 (m, br, 5H), 4.92 (m, 1H), 5.50 (m, 1H), 5.65 (m, 4H), 5.86 (m, 1H), 6.08 (m, 1H), 6.44 (m, 1H).

Example 45

4-(4-Hydroxyphenyl)-2-(2-hydroxy-1-hydroxymethyl-ethylamino)-8-(2,6-difluorophenyl)-8H-pyrido[2,3-d]pyrimidin-7one

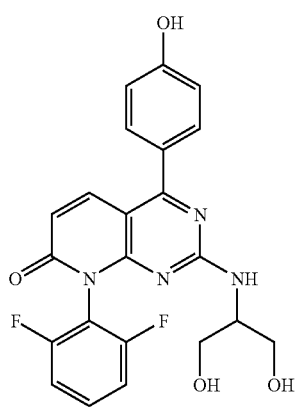

The title compound was prepared by following the procedure in Example 43 except 4-(4,4,5,5-tetramethyl-1,3,2-dioxaborolan-2-yl)phenol was used in the coupling step (56%): MS (ES) m/z 441 (M+H)+; 1H-NMR(CD3OD) δ 2.18 (m, br, 5H), 4.91 (m, 1H), 5.48 (m, 2H), 5.71 (m, 2H), 6.07 (m, 3H), 6.51 (m, 1H).

Example 46

4-(4-Methylsulfonyl-phenyl)-2-(2-hydroxy-1-hydroxymethyl-ethylamino)-8-(2,6-difluorophenyl)-8H-pyrido[2,3-d]pyrimidin-7-one

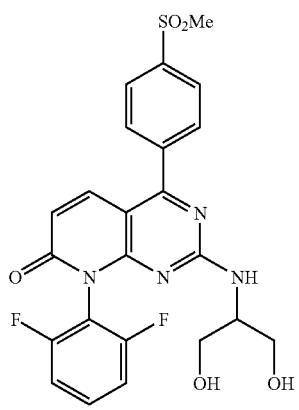

A solution of 4-(4-Methylsulfanyl-phenyl)-2-(2-hydroxy-1-hydroxymethyl-ethylamino)-8-(2,6-difluorophenyl)-8H-pyrido[2,3-d]pyrimidin-7-one (50 mg, 0.11 mmol) in methylene chloride (3 mL) was mixed with mCPBA (80.0 mg, 0.33 mmol). After stirring at room temperature for 30 minutes, the mixture was concentrated under vaco. Flash chromatography (EtOAc/Hexane, 10:1) then provided the title compound (61%): MS (ES) m/z 502 (M+H)+; 1H-NMR (CDCl3) δ 2.06 (s, br, 2H), 3.16 (s, 3H), 3.77 (m, br, 5H), 6.20 (m, br, 1H), 6.51 (m, 1H), 7.13 (m, 2H), 7.51 (m, 1H), 7.68 (m, 1H), 7.85 (m, 2H), 8.15 (m, 2H).

Example 47

4-(3-Methylsulfonyl-phenyl)-2-(2-hydroxy-1-hydroxymethyl-ethylamino)-8-(2,6-difluorophenyl)-8H-pyrido[2,3-d]pyrimidin-7-one

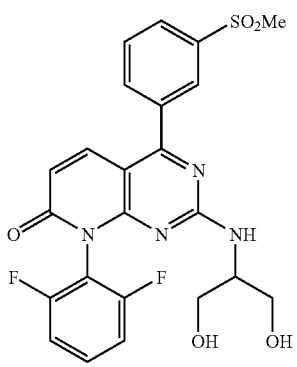

A The title compound was prepared from 4-(3-methylsulfanyl-phenyl)-2-(2-hydroxy-1-hydroxymethyl-ethylamino)-8-(2,6-difluorophenyl)-8H-pyrido[2,3-d]pyrimidin-7-one by following the procedure in Example 46 (64%): MS (ES) m/z 503 (M+H)+; 1H-NMR(CDCl3) δ 2.09 (s, br, 2H), 3.16 (s, 3H), 3.78 (m, br, 5H), 6.35 (m, br, 1H), 6.55 (m, 1H), 7.14 (m, 2H), 7.50 (m, 1H), 7.70 (m, 1H), 7.81 (m, 1H), 7.95 (m, 1H), 8.17 (m, 1H), 8.30 (s, br, 1H).

Example 48

4-(2-Methylsulfonyl-phenyl)-2-(2-hydroxy-1-hydroxymethyl-ethylamino)-8-(2,6-difluorophenyl)-8H-pyrido[2,3-d]pyrimidin-7-one

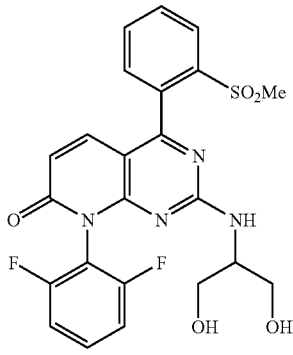

The title compound was prepared from 4-(2-methylsulfanyl-phenyl)-2-(2-hydroxy-1-hydroxymethyl-ethylamino)-8-(2,6-difluorophenyl)-8H-pyrido[2,3-d]pyrimidin-7-one by following the procedure in Example 46 (62%): MS (ES) m/z 503 (M+H)+; 1H-NMR(CDCl3) δ 2.27 (s, br, 2H), 3.28 (s, 3H), 3.77 (m, br, 5H), 6.20 (s, br, 1H), 6.41 (m, 1H), 7.13 (m, 2H), 7.25 (m, 1H), 7.48 (m, 2H), 7.81 (m, 2H), 8.26 (m, 1H).

Example 49

N-cyclopropyl-3-(8-(2,6-difluorophenyl)-2-{[2-hydroxy-1-(hydroxymethyl)ethyl]amino}-7-oxo-7,8-dihydropyrido[2,3-d]pyrimidin-4-yl)-5-fluoro-4-methylbenzamide

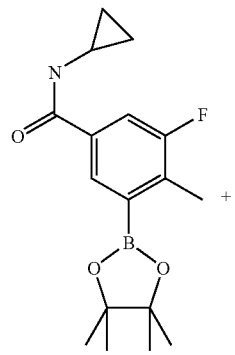

+

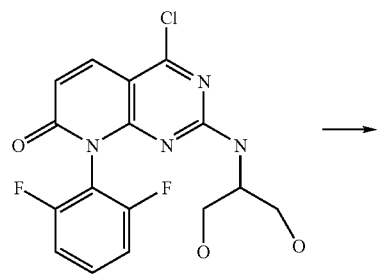

→

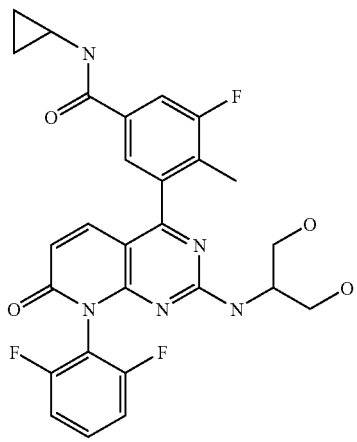

3-Fluoro-4-methylbenzoic acid (1.54 g, 0.01 mol) is dissolved in trifluoromethanesulfonic acid (10 mL) and cooled to about 0° C. NIS (2.25 g. 0.01 mol) is added in several portions over a 6 h period while maintaining the reaction temperature at about 0° C. The mixture is allowed to warm to rt. overnight. The reaction mixture is then poured over ice and extracted with ethyl acetate (3×). The organic layers are washed ($Na_2S_2O_5$) and concentrated. The material is carried on crude.

The crude acid from above (~1.5 g) is dissolved in thionyl chloride (75 mL) and heated to 80° C. for about 2 h. The mixture is then cooled to room temperature and stirred under $N_2$ overnight. The mixture is concentrated in vacuo and dissolved in 15 mL DCM. $Na_2CO_3$ (3 g) is added along with the cyclopropyl amine (0.69 mL, 0.01 moles (hereinafter "mol")). The mixture is allowed to stir overnight and purified via flash chromatography (5% $MeOH/CH_2Cl_2$) to afford 0.904 g of N-cyclopropyl-3-fluoro-5-iodo-4-methylbenzamide N-cyclopropyl-3-fluoro-5-iodo-4-methylbenzamide (0.904 g, 2.83 mmol) is dissolved in DMF (30 mL). Bis-pinicalato-diborane (1.44 g, 2.83 mmol) is added followed by $PdCl_2$.dppf (55 mg) and potassium acetate (1.38 g, 14.15 mmol). The mixture are stirred for about 18 h, concentrated in vacuo and purified via flash chromatography to afford N-cyclopropyl-3-fluoro-4-methyl-5-(4,4,5,5-tetramethyl-1,3,2-dioxaborolan-2-yl)benzamide (60 mg).

4-Chloro-8-(2,6-difluorophenyl)-2-{[2-hydroxy-1-(hydroxymethyl)ethyl]-amino}pyrido[2,3-d]pyrimidin-7(8H)-one (0.056 g, 0.17 mmol), N-cyclopropyl-3-fluoro-4-methyl-5-(4,4,5,5-tetramethyl-1,3,2-dioxaborolan-2-yl)benzamide (0.065 g, 0.17 mmol), $K_2CO_3$ (0.07 g, 0.51 mmol) and tetrakis triphenyl phosphine palladium (10 mg, 0.05 eq) are dissolved in dioxane/water (3:1, 10 mL) and heated to about 100° C. for about 3 h. The mixture is concentrated and purified via reverse phase HPLC to afford the title compound (9 mg, yellow powder, mp 214.2-217.5): LC-MS m/z 540 (M+H)$^+$, 1.69 min (ret time). HPLC indicates 96% pure.

Example 50

4-chloro-2-{[3-(diethylamino)propyl]amino}-8-(2,6-difluorophenyl)pyrido[2,3-d]pyrimidin-7(8H)-one

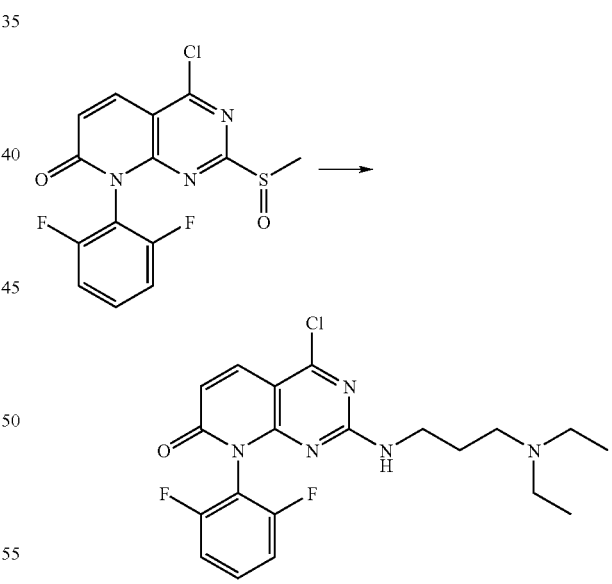

To the compound 4-chloro-8-(2,6-difluorophenyl)-2-(methylsulfinyl)-pyrido[2,3-d]pyrimidin-7(8H)-one (1.59 g, 4.47 mmol) in dichloromethane (89.4 mL) were added N,N-diethyl-1,3-propanediamine (0.845 mL, 5.36 mol) and triethylamine (1.26 uL, 8.94 mmol). The mixture was stirred at rt overnight. Some white precipitate was formed during the reaction. Filtration followed by wash with ethyl acetate/dichoromethane/methnol afforded the title compound (1.028 g, 60%). LC-MS m/z 383 (M+H)$^+$.

Example 51

4-chloro-8-(2,6-difluorophenyl)-2-(4-methyl-1,4'-bipiperidin-1'-yl)pyrido[2,3-d]pyrimidin-7(8H)-one

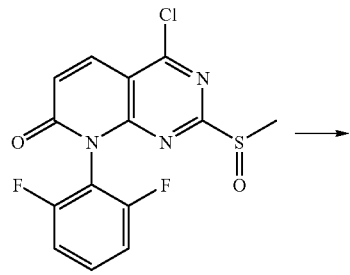

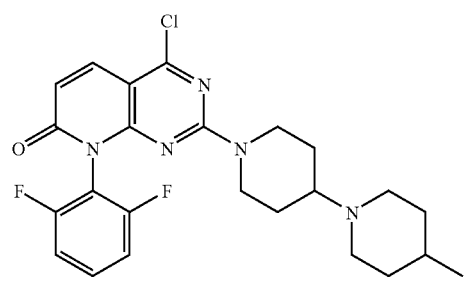

To the compound 4-chloro-8-(2,6-difluorophenyl)-2-(methylsulfinyl)pyrido[2,3-d]pyrimidin-7(8H)-one (1.39 g, 3.9 mmol) in dichloromethane (80 mL) were added 4-methyl-1,4'-bipiperidine (0.75 g, 5.85 mol) and triethylamine (1.03 mL, 11.7 mmol). The mixture was stirred at about −20° C. overnight. Filtration followed by concentration, the crude was purified with flash chromatography to afford the title compound (0.904 g, 51%). LC-MS m/z 474 (M+H)$^+$.

Example 52

3-[8-(2,6-difluorophenyl)-2-(4-methyl-1,4'-bipiperidin-1'-yl)-7-oxo-7,8-dihydropyrido[2,3-d]pyrimidin-4-yl]-4-methylbenzoic acid

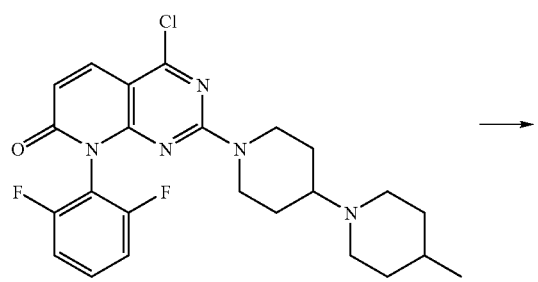

-continued

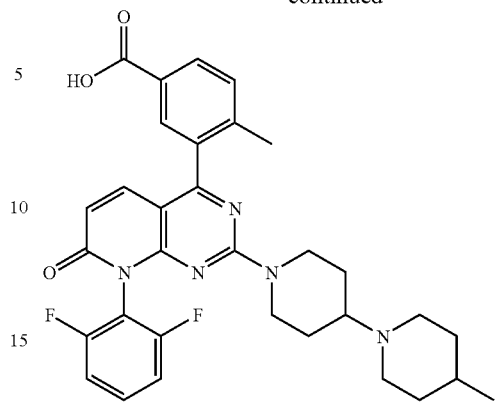

To a stirring solution of 3-iodo-4-methylbenzoic acid (60 g, 0.22 mol, 1 eq) in degassed DMF (1400 mL, 23.3 vol.) was charged 4,4,4',4',5,5,5',5'-octamethyl-2,2'-bi-1,3,2-dioxaborolane (81.4 g, 0.32 mol, 1.4 eq) followed by potassium acetate (112 g, 1.14 mole, 5eq) and [1,1'-bis(diphenylphosphino)ferrocene]-dichloropalladium(II) (18.7 g, 0.02 mole, 0.1 eq). The resulting mixture was placed under a nitrogen atmosphere and was heated to 80° C. with the exclusion of light overnight. The mixture was then concentrated under high vacuum and the residue partitioned between EtOAc and 2M HCl. The mixture was then filtered and the layers separated. The aqueous phase was re-extracted with EtOAc. The combined organics were then washed with brine, dried and evaporated to yield a brown solid that was applied to a silica plug then eluted with 2:1 cyclohexane: ethyl acetate. Fractions were then combined and evaporated to yield a brown foam that was triturated with cyclohexane, collected by filtration then dried in vacuo to yield 4-methyl-3-(4,4,5,5-tetramethyl-1,3,2-dioxaborolan-2-yl)benzoic acid. δ (CDCl$_3$) 8.50-8.49 (1H, d), 8.04-8.02 (1H, dd), 7.27-7.25 (1H, d), 2.61 (3H, s), 1.36 (12H, s).

To the compound 4-chloro-8-(2,6-difluorophenyl)-2-(4-methyl-1,4'-bipiperidin-1'-yl)pyrido[2,3-d]pyrimidin-7(8H)-one (47.5 mg, 0.1 mmol) in dioxane (3 mL) and water (1 mL) were added 4-methyl-3-(4,4,5,5-tetramethyl-1,3,2-dioxaborolan-2-yl)benzoic acid (38.4 mg, 0.15 mol), potassium carbonate (83 mg, 0.6 mmol) and tetrakis(triphenylphosphine)palladium(0) (4.6 mL, 0.005 mmol). The mixture was heated with microwave at about 150° C. for about 15 min. The mixture was concentrated & then mixed with DMSO (0.75 mL) and water (0.25 mL). Separation by HPLC afforded the title compound (39 mg, 68%). LC-MS m/z 574 (M+H)$^+$.

Example 53

3-[2-{[3-(diethylamino)propyl]amino}-8-(2,6-difluorophenyl)-7-oxo-7,8-dihydropyrido[2,3-d]pyrimidin-4-yl]-2-methylbenzoic acid

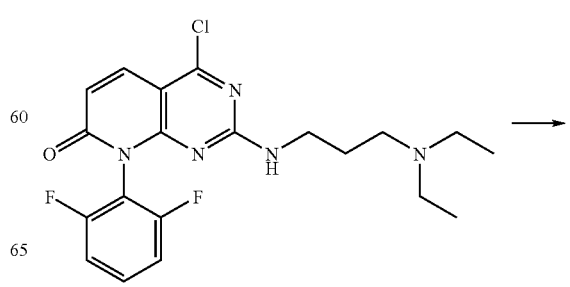

-continued

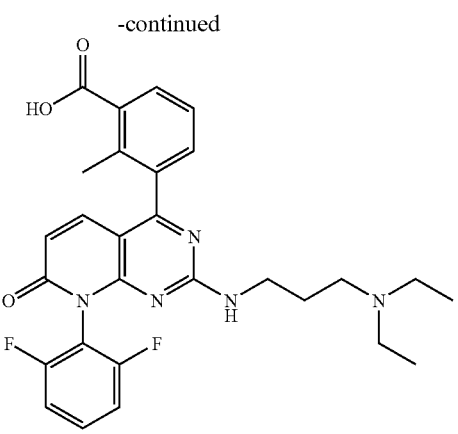

To the compound 4-chloro-2-{[3-(diethylamino)propyl]amino}-8-(2,6-difluorophenyl)pyrido[2,3-d]pyrimidin-7(8H)-one (176 mg, 0.418 mmol) in dioxane (4.5 mL) and water (1.5 mL) was added 2-methyl-3-(4,4,5,5-tetramethyl-1,3,2-dioxaborolan-2-yl)benzoic acid (173 mg, 0.626 mol), potassium carbonate (289 mg, 2.09 mmol) and tetrakis(triphenylphosphine)palladium(0) (24.2 mg, 0.0259 mmol). The mixture was heated with microwave at about 150° C. for about 15 min. The mixture was filtered. Separation by HPLC with TFA afforded the title compound (238 mg, 99%). LC-MS m/z 522 (M+H)⁺.

Example 54

1,1-dimethylethyl 3-[2-{[3-(diethylamino)propyl]amino}-8-(2,6-difluorophenyl)-7-oxo-7,8-dihydropyrido[2,3-d]pyrimidin-4-yl]-5-fluoro-4-methylbenzoate trifluoroacetate

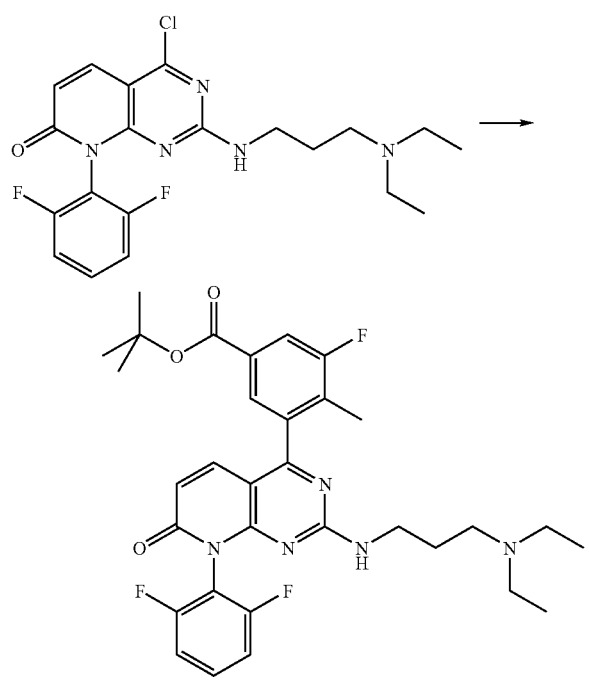

To the compound 4-chloro-2-{[3-(diethylamino)propyl]amino}-8-(2,6-difluorophenyl)pyrido[2,3-d]pyrimidin-7(8H)-one (600 mg, 1.422 mmol) in dioxane (15 mL) and water (5 mL) were added 1,1-dimethylethyl 3-fluoro-4-methyl-5-(4,4,5,5-tetramethyl-1,3,2-dioxaborolan-2-yl)benzoate (542 mg, 2.132 mol), potassium carbonate (590 mg, 4.26 mmol) and tetrakis(triphenylphosphine)-palladium(0) (82 mg, 0.071 mmol). The mixture was heated with microwave at 150° C. for 15 minutes. The mixture was filtered. Separation by HPLC with TFA afforded the crude title compound.

Example 55

4-[2-{[3-(diethylamino)propyl]amino}-8-(2,6-difluorophenyl)-7-oxo-7,8-dihydropyrido[2,3-d]pyrimidin-4-yl]benzoic acid

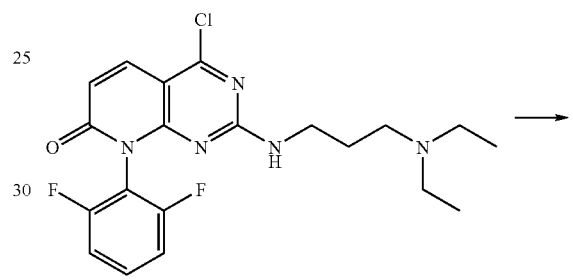

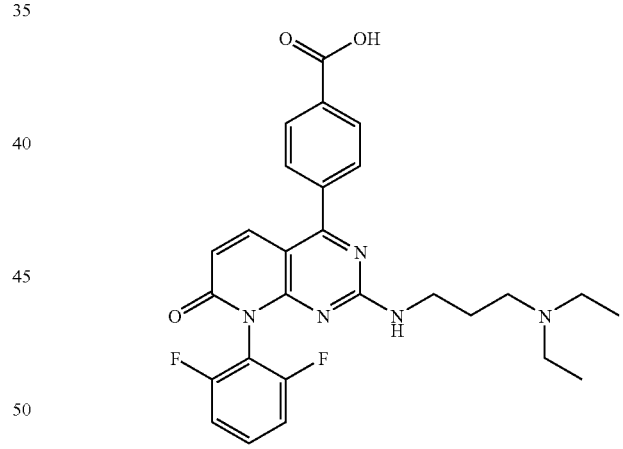

To the compound 4-chloro-2-{[3-(diethylamino)propyl]amino}-8-(2,6-difluorophenyl)pyrido[2,3-d]pyrimidin-7(8H)-one (168.75 mg, 0.40 mmol) in dioxane (12 mL) and water (4 mL) were added 4-(4,4,5,5-tetramethyl-1,3,2-dioxaborolan-2-yl)benzoic acid (148.85 mg, 0.60 mol), potassium carbonate (208 mg, 1.20 mmol) and tetrakis(triphenylphosphine)palladium(0) (23 mg, 0.02 mmol). The mixture was heated with microwave at 150° C. for 15 min. The mixture was concentrated. It was mixed with DMSO (0.75 mL) and water (0.25 mL). Separation by HPLC afforded the title compound (147 mg, 72%). LC-MS m/z 508 (M+H)⁺.

Example 56

3-[2-{[3-(diethylamino)propyl]amino}-8-(2,6-difluorophenyl)-7-oxo-7,8-dihydropyrido[2,3-d]pyrimidin-4-yl]benzoic acid

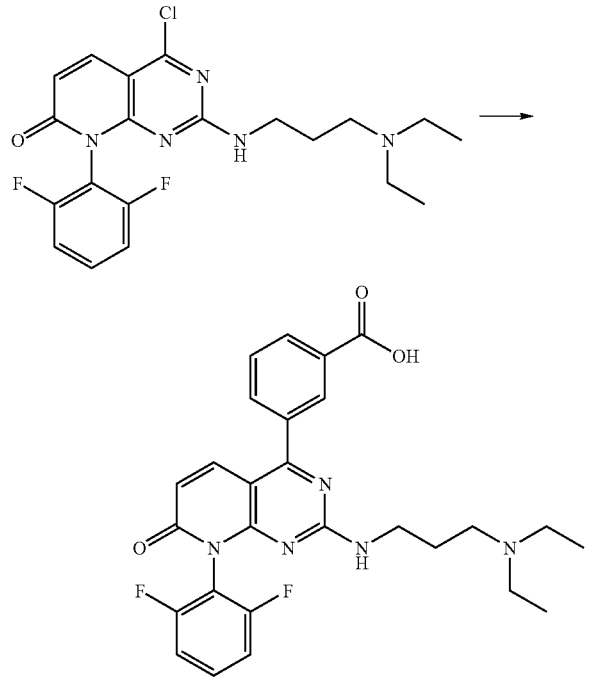

To the compound 4-chloro-2-{[3-(diethylamino)propyl]amino}-8-(2,6-difluorophenyl)pyrido[2,3-d]pyrimidin-7(8H)-one (210.5 mg, 0.50 mmol) in dioxane (15 mL) and water (5 mL) were added 3-(4,4,5,5-tetramethyl-1,3,2-dioxaborolan-2-yl)benzoic acid (125 mg, 0.75 mol), potassium carbonate (210 mg, 1.20 mmol) and tetrakis(triphenylphosphine)palladium(0) (29 mg, 0.025 mmol). The mixture was heated with microwave at about 150° C. for about 15 min. The mixture was concentrated, then mixed with DMSO (0.75 mL) and water (0.25 mL). Separation by HPLC afforded the title compound (467 mg, 32%). LC-MS m/z 508 (M+H)$^+$.

Example 57

5-Chloro-1-(2,6-difluorophenyl)-7-(methylthio)-3,4-dihydropyrimido[4,5-d]pyrimidin-2(1H)-one 57a) 4-chloro-6-[(2,6-difluorophenyl)amino]-2-(methylthio)-5-pyrimidinecarbonitrile

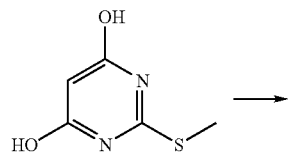

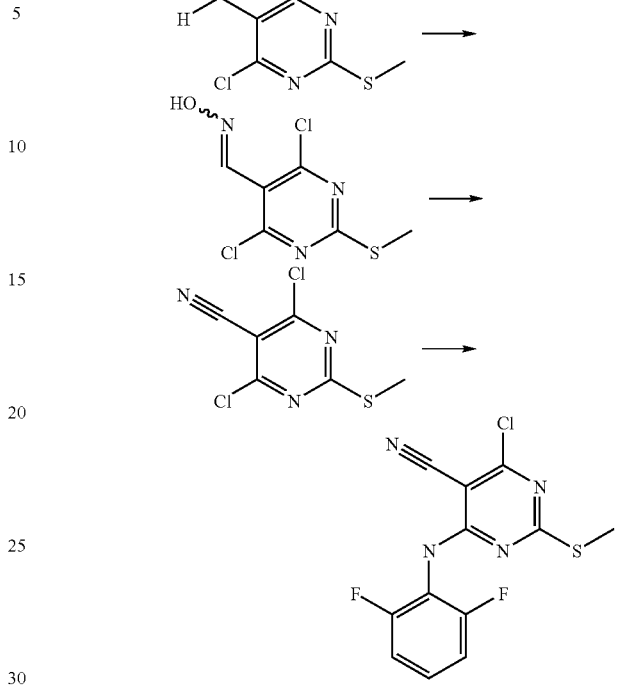

To the solution of phosphorus oxychloride (65 mL, 0.70 mol) in trichloroethylene (46.5 mL) was added DMF (25 mL, 0.32 mol) slowly to keep the temperature between 5° C. to 10° C. The solution was then warmed up to room temperature before 6-hydroxy-2-(methylthio)-4(1H)-pyrimidinone (25 g, 0.16 mol) was added in portions. The resultant reaction mixture was heated at 80° C. overnight followed by concentration under vacuum. The resulting slurry like residue was poured into ice, stirred for about 2 hours then filtered to afford the crude product. The crude product was further purified by recrystalization with hexane to afford 4,6-dichloro-2-(methylthio)-5-pyrimidinecarbaldehyde (21.3 g, 61%). $^1$H-NMR (CDCl$_3$) δ 2.66 (s, 3 H), 10.4 (s, 1 H).

To the mixture of hydroxylamine hydrochloride (139 mg, 2.0 mmol), HOAc (0.113 mL, 2.0 mmol) and EtOH (5 mL) was added 4,6-dichloro-2-(methylthio)-5-pyrimidinecarbaldehyde (223 mg, 1.0 mol) to room temperature. The solution was then heated at 50° C. for about 1 hour, 60° C. for about 30 minutes and 70° C. for about 30 minutes before it was concentrated under vacuum and washed with H$_2$O (10-20 mL) to afford 4,6-dichloro-2-(methylthio)-5-pyrimidinecarbaldehyde oxime (190 mg, 80%). LC-MS m/z 238 (M+H)$^+$1.57 minute, 1.65 minute; $^1$H-NMR (CDCl$_3$) δ 2.62, 2.65 (3 H), 7.53, 8.30 (1 H).

To 4,6-dichloro-2-(methylthio)-5-pyrimidinecarbaldehyde oxime (2.38 g, 10 mmol) was added SOCl$_2$ (21.8 mL, 0.30 mol) slowly at room temperature. The solution was then heated at 75° C. for about 3 hours before it was concentrated under vacuum. The residue SOCl$_2$ was removed by evaporation with toluene (5 mL) under vacuum. The resulting solid was washed with EtOH/H$_2$O (10 mL, 1:1) to afford 4,6-dichloro-2-(methylthio)-5-pyrimidinecarbonitrile (2.04 g, 93%). LC-MS m/z 220 (M+H)$^+$1.99 minute; $^1$H-NMR (CDCl$_3$) δ 2.64(3 H).

To the solution of 4,6-dichloro-2-(methylthio)-5-pyrimidinecarbonitrile (2.20 g, 10.0 mmol) in DMF (10 mL) was added 2,6-difluoroaniline (2.17 mL, 20.0 mmol). The solution was stirred at 50° C. for about 60 minutes. The mixture was slowly added into a solution of MeOH (20 mL) and water (30 mL). The resultant solid was filtered and washed with MeOH/H$_2$O (20 mL, 1:1) to give 4-chloro-6-[(2,6-difluorophenyl)amino]-2-(methylthio)-5-pyrimidinecarbonitrile as a white solid (2.82 g, 90%). LC-MS m/z 313 (M+H)$^+$; $^1$H-NMR (CDCl$_3$) δ 2.33 (s, 3 H), 6.94 (s, 1 H), 7.04 (m, 2 H), 7.35 (m, 1 H).

57b) 5-(Aminomethyl)-6-chloro-N-(2,6-difluorophenyl)-2-(methylthio)-4-pyrmidinamine

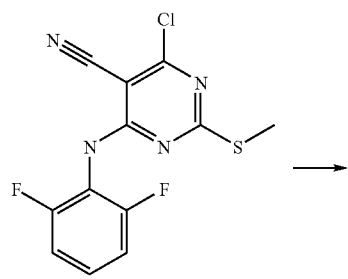

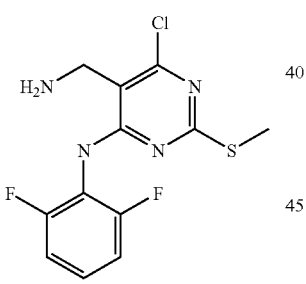

To the solution of 4-chloro-6-[(2,6-difluorophenyl)amino]-2-(methylthio)-5-pyrimidinecarbonitrile (0.938 g) was added borane●THF complex (1.0 M, 15 mL). The reaction mixture was then heated at reflux for about 4 h until all the starting material disappeared. The solution was cooled to r.t., mixed with HCl solution (6 M, 5 mL), and stirred at room temperature for about 30 minutes. The solution was then mixed with NaOH solution (3 M) to pH 9.0-10.0. The organic phase was separated and the aqueous layer was extracted with EtOAc (3×30 mL). The combined organic layers were washed with brine (50 mL), collected, dried over Na$_2$SO$_4$ and concentrated to afford the title compound 0.97 g (quantative). LC-MS m/z 317 (M+H)$^+$, 1.5 min (ret. time).

57c) 5-Chloro-1-(2,6-difluorophenyl)-7-(methylthio)-3,4-dihydropyrimido[4,5-d]pyrimidin-2(1H)-one

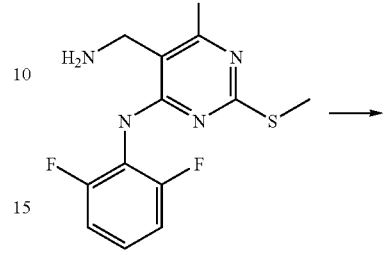

To the solution of 5-(aminomethyl)-6-chloro-N-(2,6-difluorophenyl)-2-(methylthio)-4-pyrimidinamine (0.317 g) in CH$_2$Cl$_2$ (5 mL) was added the mixture of carbonyl diimidazole (0.178 g) in CH$_2$Cl$_2$ (5 mL). The resultant mixture was stirred for about 3 hours at r.t., mixed with CH$_2$Cl$_2$ (10 mL) and washed with HCl (1 N, 2×10 mL) and H$_2$O (20 mL). The organic layers were collected, dried over Na$_2$SO$_4$, filtered and concentrated to provide the title compound (0.279 g, 81%). LC-MS m/z 343 (M+H)$^+$, 1.75 min (ret. time); $^1$H-NMR (400 MHz, CDCl$_3$) δ 7.44-7.40 (m, 1H), 7.07-7.03 (m, 2H), 5.84 (br, 1H), 4.62 (s, 2H), 2.19 (s, 3H).

Example 58

5-chloro-1-(2,6-difluorophenyl)-7-(methylsulfinyl)-3,4-dihydropyrimido[4,5-d]pyrimidin-2(1H)-one

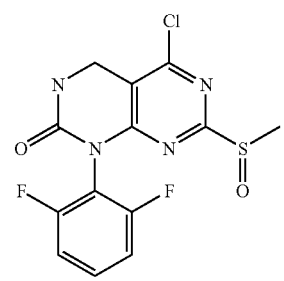

To a solution of 5-chloro-1-(2,6-difluorophenyl)-7-(methylthio)-3,4-dihydropyrimido[4,5-d]pyrimidin-2(1H)-one (1.71 g, 5 mmol) in CH$_2$Cl$_2$ (60 mL) was added m-CPBA (1.17 g, 5.2 mmol). The mixture was stirred at room temperature for 10 minutes, then directly loaded onto a column. Flash chromatography (mobile phase EtOAc/Hexane) afforded the title compound as a white solid 1.58 g (88%). LC-MS m/z 358 (M+H)$^+$.

Example 59

5-chloro-1-(2,6-difluorophenyl)-7-[4-(1-pyrrolidinyl)-1-piperidinyl]-3,4-dihydropyrimido[4,5-d]pyrimidin-2(1H)-one

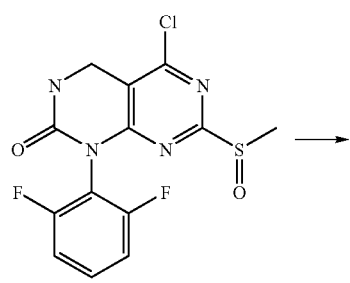

To a solution of 5-chloro-1-(2,6-difluorophenyl)-7-(methylsulfinyl)-3,4-dihydropyrimido[4,5-d]pyrimidin-2(1H)-one (250 mg, 0.70 mmol) in DCM (10 mL) were added 4-(1-pyrrolidinyl)piperidine (323 mg, 2.1 mmol) and N,N-diisopropylethylamine (0.3 mL, 1.7 mmol). The resultant solution was stirred at room temperature overnight. The result mixture was concentrated. CombiFlash chromatography (mobile phase DCM/DCM[90]+MeOH[7]+NH$_4$OH[3]) provided the title compound as a white solid (253 mg, 81%). LC-MS m/z 449 (M+H)$^+$ Example 60

3-{8-(2,6-difluorophenyl)-7-oxo-2-[4-(1-pyrrolidinyl)-1-piperidinyl]-5,6,7,8-tetrahydropyrimido[4,5-d]pyrimidin-4-yl}-N-(4-fluorophenyl)-4-methylbenzamide

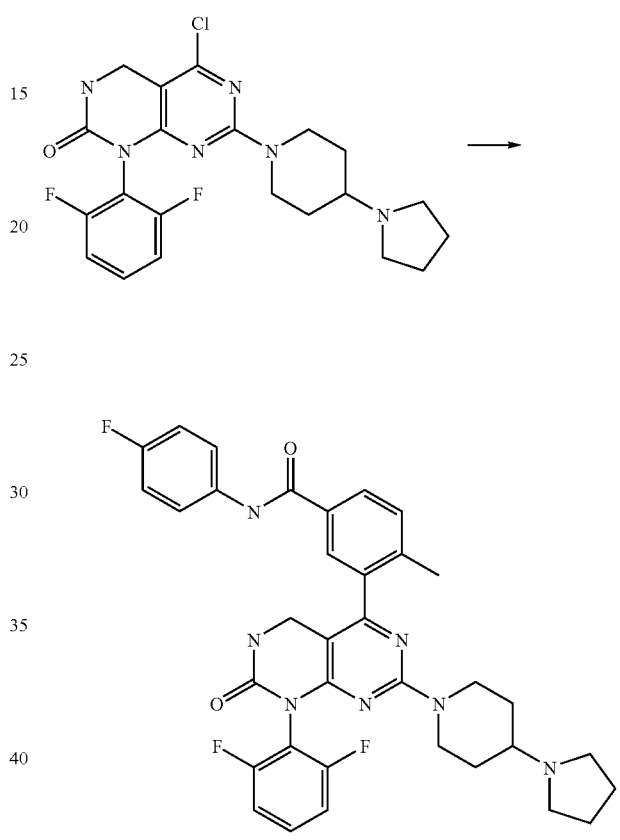

To a solution of 5-chloro-1-(2,6-difluorophenyl)-7-[4-(1-pyrrolidinyl)-1-piperidinyl]-3,4-dihydropyrimido[4,5-d]pyrimidin-2(1H)-one (18 mg, 0.04 mmol) in dioxane (1.5 mL)/water (0.5 mL) were added potassium carbonate (34 mg, 0.25 mmol), tetrakis(triphenylphosphine)palladium(0) (2.3 mg, 0.002 mmol) and N-(4-fluorophenyl)-4-methyl-3-(4,4,5,5-tetramethyl-1,3,2-dioxaborolan-2-yl)benzamide (22 mg, 0.062 mmol). The reaction mixture was bubbled with N$_2$ for 5 mins, then microwaved at about 150° C. for about 30 mins. The reaction mixture was concentrated. CombiFlash chromatography (mobile phase DCM/DCM[90]+MeOH[7]+NH$_4$OH[3]) provided the title compound as a white solid (14 mg, 54%).

LC-MS m/z 642 (M+H)$^+$; $^1$H-NMR (CD$_3$OD) δ 1.32 (m, 2 H), 1.80 (m, 4 H), 1.88 (m, 2 H), 2.24 (m, 1 H), 2.33 (s, 3 H), 2.62 (m, 4 H), 2.74 (t, 2 H), 4.17 (m, 2 H), 4.40 (m, 2 H), 7.12 (m, 4 H), 7.52 (m, 2 H), 7.72 (m, 2 H), 7.82 (s, 1 H), 7.98 (d, 1 H).

Example 61

7-(1,4'-bipiperidin-1'-yl)-5-chloro-1-(2,6-difluorophenyl)-3,4-dihydropyrimido[4,5-d]pyrimidin-2(1H)-one

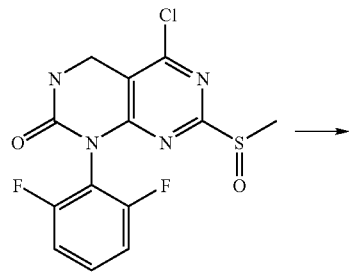

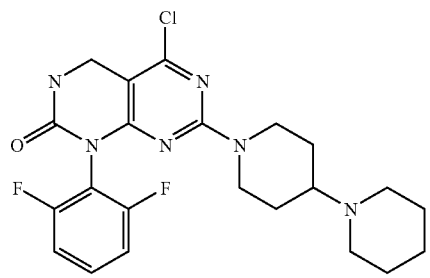

To a solution of 5-chloro-1-(2,6-difluorophenyl)-7-(methylsulfinyl)-3,4-dihydropyrimido[4,5-d]pyrimidin-2(1H)-one (200 mg, 0.56 mmol) in DCM (10 mL) were added 1,4'-bipiperidine (270 mg, 1.61 mmol) and N,N-diisopropylethylamine (0.3 mL, 1.7 mmol). The resultant solution was stirred at room temperature over night. The result mixture was concentrated. CombiFlash chromatography (mobile phase DCM/DCM[90]+MeOH[7]+NH$_4$OH[3]) provided the title compound as a white solid (298 mg, 83%). LC-MS m/z 463 (M+H)$^+$.

Example 62

3-[2-(1,4'-bipiperidin-1'-yl)-8-(2,6-difluorophenyl)-7-oxo-5,6,7,8-tetrahydropyrimido[4,5-d]pyrimidin-4-yl]-N-(4-fluorophenyl)-4-methylbenzamide

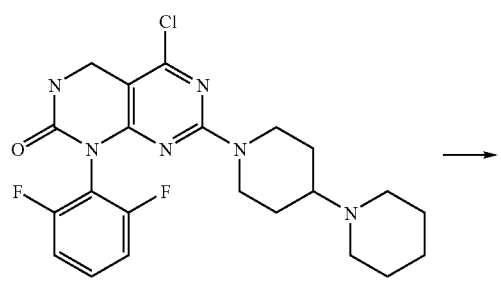

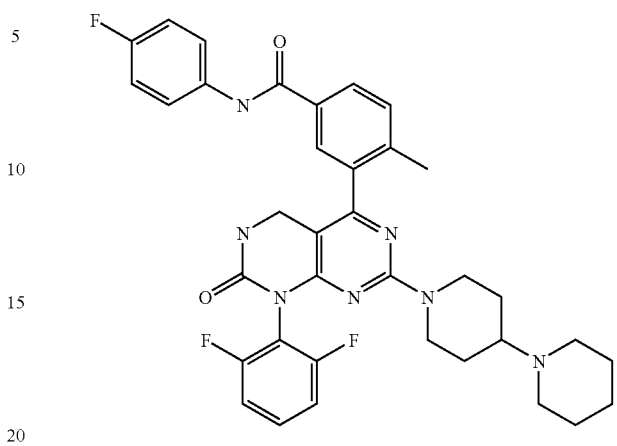

To a solution of compound 7-(1,4'-bipiperidin-1'-yl)-5-chloro-1-(2,6-difluorophenyl)-3,4-dihydropyrimido[4,5-d]pyrimidin-2(1H)-one (18 mg, 0.04 mmol) in dioxane (1.5 mL)/water (0.5 mL) were added potassium carbonate (34 mg, 0.25 mmol), tetrakis(triphenylphosphine)palladium(0) (2.3 mg, 0.002 mmol) and N-(4-fluorophenyl)-4-methyl-3-(4,4,5,5-tetramethyl-1,3,2-dioxaborolan-2-yl)benzamide (22 mg, 0.062 mmol). The reaction mixture was bubbled with N$_2$ for 5 mins, then microwaved at about 150° C. for about 30 mins. The reaction mixture was concentrated. CombiFlash chromatography (mobile phase DCM/DCM[90]+MeOH [7]+NH$_4$OH[3]) provided the title compound as a white solid (13 mg, 51%). LC-MS m/z 656 (M+H)$^+$; $^1$H-NMR (CD$_3$OD) δ 1.37 (m, 2 H), 1.48 (m, 2 H), 1.60 (m, 4 H), 1.80 (m, 2 H), 2.33 (s, 3 H), 2.56 (m, 5 H), 2.72 (t, 2 H), 4.17 (m, 2 H), 4.46 (m, 2 H), 7.12 (m, 4 H), 7.52 (m, 2 H), 7.72 (m, 2 H), 7.82 (s, 1 H), 7.98 (d, 1 H).

Example 63

5-chloro-1-(2,6-difluorophenyl)-7-{[2-(dimethylamino)ethyl]amino}-3,4-dihydropyrimido[4,5-d]pyrimidin-2(1H)-one

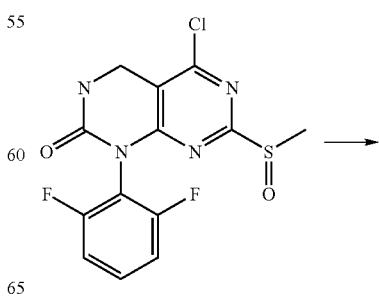

-continued

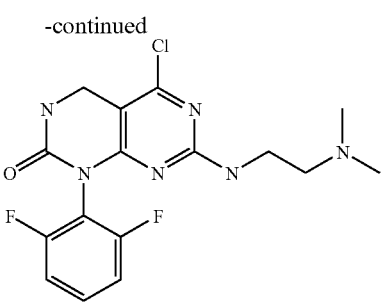

To a solution of 5-chloro-1-(2,6-difluorophenyl)-7-(methylsulfinyl)-3,4-dihydropyrimido[4,5-d]pyrimidin-2(1H)-one (800 mg, 2.23 mmol) in DCM (45 mL) were added N,N-dimethylethylenediamine (0.36 mL, 3.23 mmol) and triethylamine (0.63 mL, 4.5 mmol). The resultant solution was stirred at room temperature overnight. The result mixture was concentrated. CombiFlash chromatography (mobile phase DCM/DCM[90]+MeOH[7]+NH₄OH[3]) provided the title compound as a white solid (730 mg, 85%). LC-MS m/z 383 (M+H)⁺.

Example 64

3-(8-(2,6-difluorophenyl)-2-{[2-(dimethylamino)ethyl]amino}-7-oxo-5,6,7,8-tetrahydropyrimido[4,5-d]pyrimidin-4-yl)benzoic acid

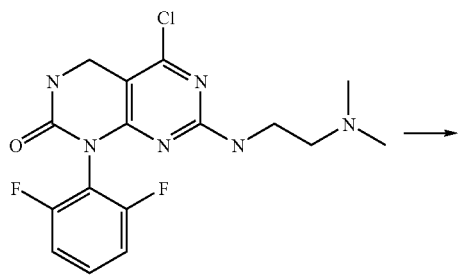

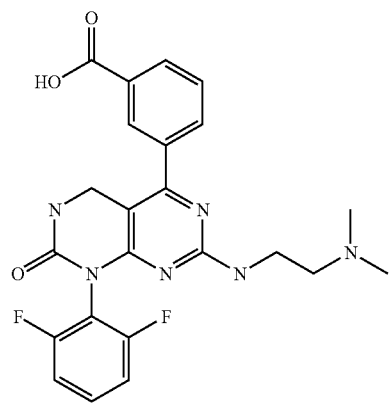

To a solution of 5-chloro-1-(2,6-difluorophenyl)-7-{[2-(dimethylamino)-ethyl]amino}-3,4-dihydropyrimido[4,5-d]pyrimidin-2(1H)-one (100 mg, 0.26 mmol) in dioxane (9 mL)/water (3 mL) were added potassium carbonate (217 mg, 1.57 mmol), tetrakis(triphenylphosphine)palladium(0) (15 mg, 0.013 mmol) and 3-(4,4,5,5-tetramethyl-1,3,2-dioxaborolan-2-yl)benzoic acid (65 mg, 0.39 mmol). The reaction mixture was bubbled with N₂ for 5 mins, then microwaved at about 150° C. for about 30 mins. The reaction mixture was concentrated. To the concentrated mixture were added DMSO (2 mL), H₂O (0.5 mL) and AcOH (0.05 mL). Separation via a HPLC then provided the title compound as a white solid (120 mg, 98%). LC-MS m/z 469 (M+H)⁺.

Example 65

4-(8-(2,6-difluorophenyl)-2-{[2-(dimethylamino)ethyl]amino}-7-oxo-5,6,7,8-tetrahydropyrimido[4,5-d]pyrimidin-4-yl)benzoic acid

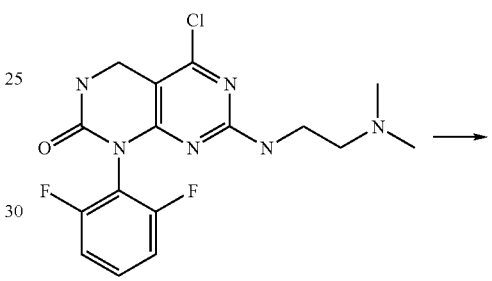

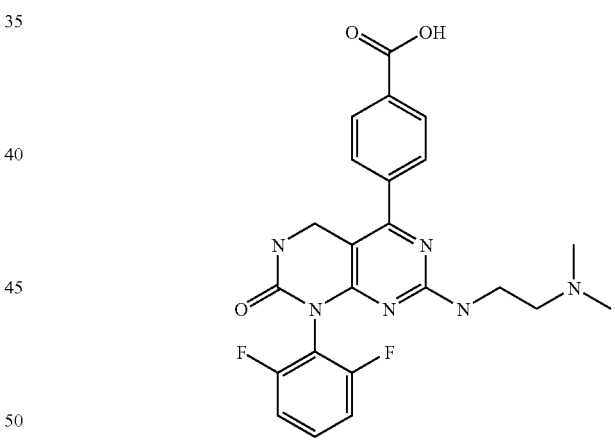

To a solution of 5-chloro-1-(2,6-difluorophenyl)-7-{[2-(dimethylamino)-ethyl]-amino}-3,4-dihydropyrimido[4,5-d]pyrimidin-2(1H)-one (150 mg, 0.39 mmol) in dioxane (12 mL)/water (4 mL) were added potassium carbonate (325 mg, 2.36 mmol), tetrakis(triphenylphosphine)palladium(0) (23 mg, 0.019 mmol) and 4-(4,4,5,5-tetramethyl-1,3,2-dioxaborolan-2-yl)benzoic acid (146 mg, 0.59 mmol). The reaction mixture was bubbled with N₂ for about 5 mins, then microwaved at about 150° C. for about 30 mins. The reaction mixture was concentrated. To the concentrated mixture were added DMSO (2 mL), H₂O (0.5 mL) and AcOH (0.05 mL). Separation via a HPLC then provided the title compound as a white solid (142 mg, 77%). LC-MS m/z 469 (M+H)⁺.

Example 66

4-(8-(2,6-difluorophenyl)-2-{[2-(dimethylamino)ethyl]amino}-7-oxo-5,6,7,8-tetrahydropyrimido[4,5-d]pyrimidin-4-yl)-3-methylbenzoic acid

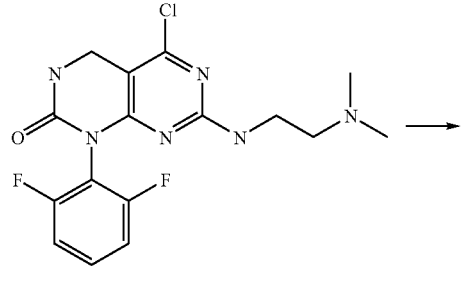

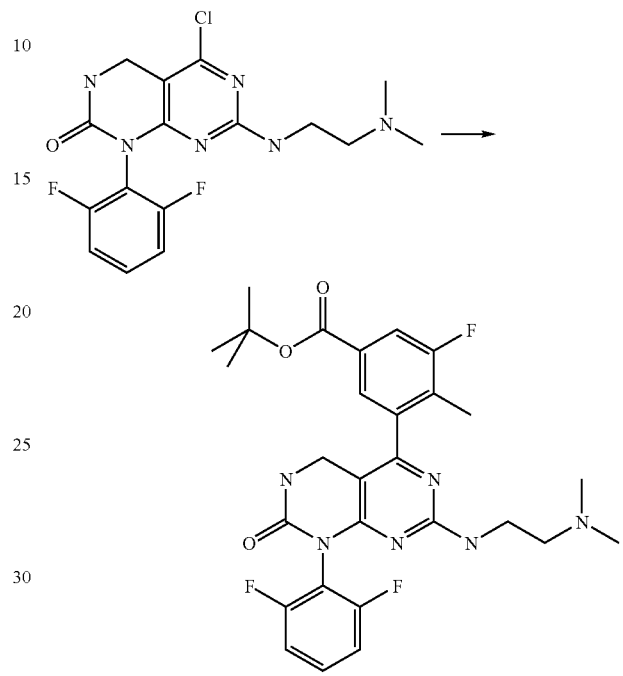

To a solution of 5-chloro-1-(2,6-difluorophenyl)-7-{[2-(dimethylamino)ethyl]-amino}-3,4-dihydropyrimido[4,5-d]pyrimidin-2(1H)-one (200 mg, 0.52 mmol) in dioxane (15 mL)/water (5 mL) were added potassium carbonate (433 mg, 3.14 mmol), tetrakis(triphenylphosphine)palladium(0) (31 mg, 0.027 mmol) and 3-methyl-4-(4,4,5,5-tetramethyl-1,3,2-dioxaborolan-2-yl)benzoic acid (205 mg, 0.78 mmol). The reaction mixture was bubbled with $N_2$ for about 10 mins, then microwaved at 150° C. for about 30 mins. The reaction mixture was concentrated. To the concentrated mixture were added DMSO (2 mL), $H_2O$ (0.5 mL) and AcOH (0.05 mL). Gilson with TFA provided the title compound as a white solid (310 mg, 99%). LC-MS m/z 483 (M+H)$^+$.

Example 67

1,1-dimethylethyl 3-(8-(2,6-difluorophenyl)-2-{[2-(dimethylamino)ethyl]amino}-7-oxo-5,6,7,8-tetrahydropyrimido[4,5-d]pyrimidin-4-yl)-5-fluoro-4-methylbenzoate To a solution of 5-chloro-1-(2,6-difluorophenyl)-7-{[2-(dimethylamino)ethyl]amino}-3,4-dihydropyrimido[4,5-d]pyrimidin-2(1H)-one (200 mg, 0.52 mmol) in dioxane (15 mL)/water (5 mL) were added potassium carbonate (433 mg, 3.14 mmol), tetrakis(triphenylphosphine)palladium(0) (31 mg, 0.027 mmol) and (5-{[(1,1-dimethylethyl)oxy]carbonyl}-3-fluoro-2-methylphenyl)boronic acid (159 mg, 0.63 mmol). The reaction mixture was bubbled with $N_2$ for 10 mins, then microwaved at 150° C. for 30 mins. The reaction mixture was concentrated. To the concentrated mixture were added DMSO (2 mL), $H_2O$ (0.5 mL) and AcOH (0.05 mL). Separation via a HPLC then provided the title compound as a white solid (270 mg, 88%). LC-MS m/z 587 (M+H)$^+$.

Example 68

3-(8-(2,6-difluorophenyl)-2-{[2-(dimethylamino)ethyl]amino}-7-oxo-5,6,7,8-tetrahydropyrimido[4,5-d]pyrimidin-4-yl)-4-methylbenzoic acid

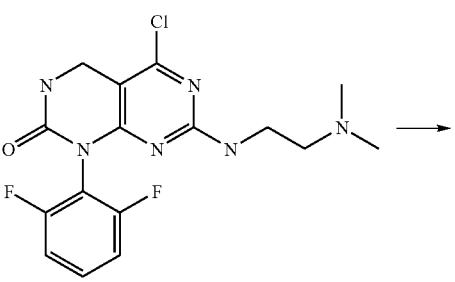

-continued

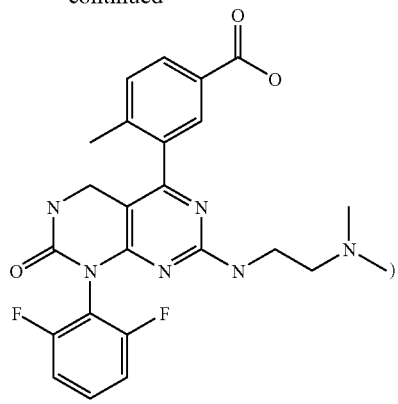

To the solution of 5-chloro-1-(2,6-difluorophenyl)-7-{[2-(dimethylamino)ethyl]amino}-3,4-dihydropyrimido[4,5-d]pyrimidin-2(1H)-one (191 mg, 0.50 mmol) in dioxane (15 mL) and water (5 mL) were added 4-methyl-3-(4,4,5,5-tetramethyl-1,3,2-dioxaborolan-2-yl)benzoic acid (197 mg, 0.75 mmol), $K_2CO_3$ (415 mg, 3.0 mmol) and tetrakis(triphenyl-phosphine)palladium(0) (23 mg, 0.025 mmol). The reaction mixture was heated to 150° C. for about 15 minutes with microwave. The reaction mixture was concentrated to dry then was added DMSO (2 mL), water (0.5 mL) and HOAc (1 drop). The solution was filtered and applied to the reverse phase HPLC to afford the titled compound 0.24 g (quantitative). LC-MS m/z 483 (M+H)$^+$; $^1$H-NMR (CD$_3$OD) 2.36 (s, 3 H), 2.76 (s, 6H), 3.16 (s, 2 H), 3.56 (s, 2 H), 4.13 (s, 2 H), 7.21 (m, 1 H), 7.53 (m, 2 H), 7.95 (s, 1 H), 8.09 (d, J=7.6 Hz, 1 H).

Example 69

3-(8-(2,6-difluorophenyl)-2-{[2-(dimethylamino)ethyl]amino}-7-oxo-5,6,7,8-tetrahydropyrimido[4,5-d]pyrimidin-4-yl)-4-ethylbenzoic acid

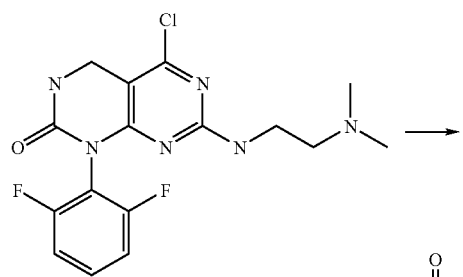

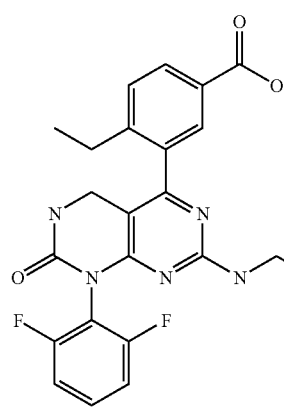

The title compound was prepared by following the procedure in Example 68 except 3-(dihydroxyboranyl)-4-ethylbenzoic acid was used in the coupling reaction (yield: 38%). LC-MS m/z 497 (M+H)$^+$; $^1$H-NMR (CD$_3$OD) 1.22 (t, J=7.6 Hz, 3 H), 2.68 (s, 2 H), 2.77 (s, 6 H), 3.16 (m, 2 H), 3.53 (m, 2 H), 4.13 (m, 2 H), 7.18 (m, 2 H), 7.55 (m, 2 H), 7.86 (s, 1 H), 8.10 (m 1 H).

Example 70

5-chloro-7-{[3-(diethylamino)propyl]amino}-1-(2,6-difluorophenyl)-3,4-dihydropyrimido[4,5-d]pyrimidin-2(1H)-one trifluoroacetate

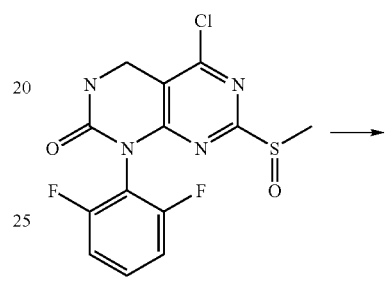

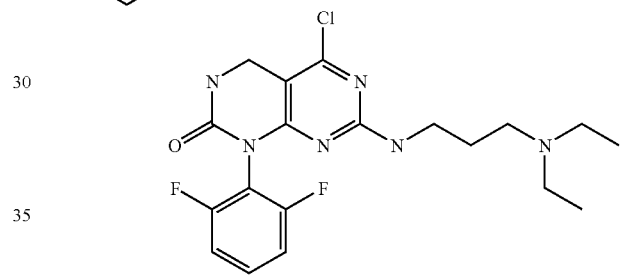

To 5-chloro-1-(2,6-difluorophenyl)-7-(methylsulfinyl)-3,4-dihydropyrimido[4,5-d]pyrimidin-2(1H)-one (275 mg, 0.767 mmol) in dichloromethane (15 mL) was added N,N-diethyl-1,3-propyldiamine (0.181 mL, 1.15 mmol) and triethylamine (0.215 mL, 1.53 mmol). The mixture was stirred over night. The mixture was concentrated and separated by Gilson HPLC (with 0.1% TFA) to afford the title compound (207 mg, 64%).

Example 71

3-[2-{[3-(diethylamino)propyl]amino}-8-(2,6-difluorophenyl)-7-oxo-5,6,7,8-tetrahydropyrimido[4,5-d]pyrimidin-4-yl]-4-methylbenzoic acid

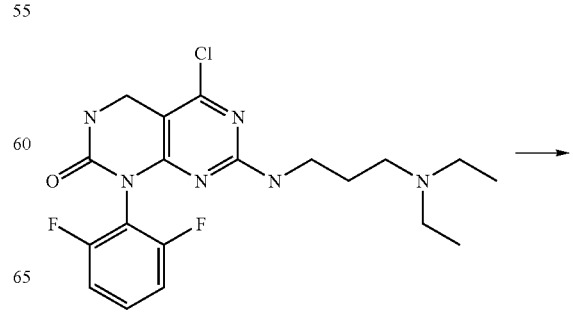

-continued

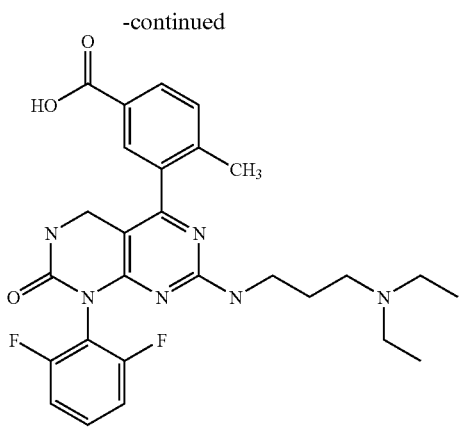

To 5-chloro-7-{[3-(diethylamino)propyl]amino}-1-(2,6-difluorophenyl)-3,4-dihydropyrimido[4,5-d]pyrimidin-2(1H)-one (207 mg, 0.488 mmol) in 1,4-dioxane (7.5 mL) and water (2.5 mL) was added 4-methyl-3-(4,4,5,5-tetramethyl-1,3,2-dioxaborolan-2-yl)benzoic acid (0.192 g, 0.733 mmol), tetrakis(triphenylphosphine)-palladium(0) (28.3 mg, 0.024 mmol), and potassium carbonate (270 mg, 1.95 mmol). The mixture was heated with microwave for about 15 min at 150° C., and then allowed to cool to room temperature. The mixture was concentrated and separated by HPLC to afford the title compound (66 mg, 26%). LC-MS m/z 525 (M+H)$^+$.

Example 72

3-[8-(2,6-difluorophenyl)-2-(methylthio)-7-oxo-7,8-dihydropyrido[2,3-d]pyrimidin-4-yl]-4-methylbenzoic acid

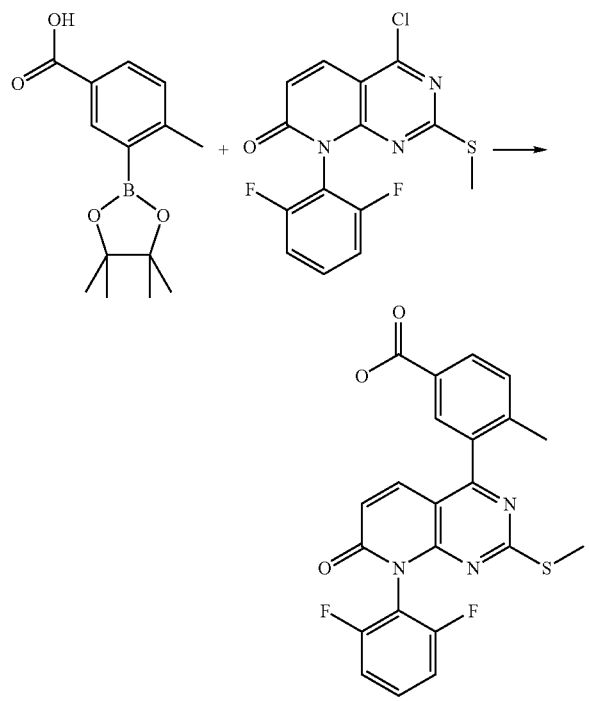

The solution of 4-chloro-8-(2,6-difluorophenyl)-2-(methylthio)pyrido[2,3-d]pyrimidin-7(8H)-one (1.70 g, 5.00 mmol) in DME (150 mL) and H$_2$O (50 mL), in a pressure flask (500 mL, Chemglass), was added 4-methyl-3-(4,4,5,5-tetramethyl-1,3,2-dioxa borolan-2-yl) benzoic acid (1.97 g, 7.50 mmol) and K$_2$CO$_3$ (4.15 g, 30.0 mmol). The resulting mixture was degassed with Argon for 5 minutes, mixed with Pd(PPh$_3$)$_4$ (0.232 g, 0.20 mmol) and heated with a preheated oil bath (160° C.) under vigorous stirring for 30 minutes. The reaction mixture was filtered through celite, concentrated under vaccum to remove DME. It was then mixed with EtOAc (200 mL) and AcOH (2.5 mL), and shaked. The layers were separated. The organic layer was collected, further washed with brine (70 mL), dried over Na$_2$SO$_4$, filtered, concentrated and purified via a flash chromatography (load column with DCM, mobile phase EtOAc/Hexane) to afford the title compound as a white solid 2.15 g (98%). LC-MS (ES) m/z 440 (M+H)$^+$; $^1$H-NMR (CD$_3$OD) δ 2.27 (s, 3 H), 2.31 (s, 3 H), 6.71 (d, J=9.6 Hz, 1 H), 7.28 (t, J=8.2 Hz, 2 H), 7.57 (d, J=8.4 Hz, 1 H), 7.64 (m, 2 H), 8.00 (d, J=1.6 Hz, 1 H), 8.14 (dd, J$_1$=7.6 Hz, J$_2$=1.6 Hz, 1 H).

Example 73

3-[8-(2,6-difluorophenyl)-2-(methylthio)-7-oxo-5,6,7,8-tetrahydropyrimido[4,5-d]pyrimidin-4-yl]-N,N,4-trimethylbenzamide

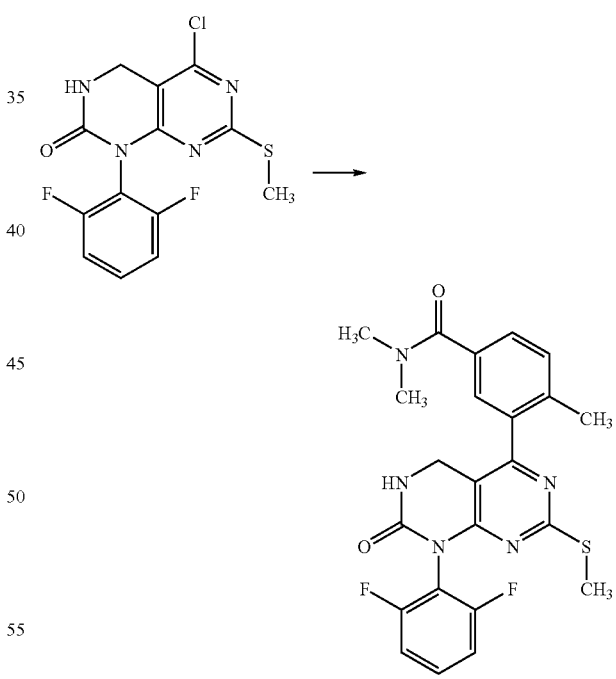

4-methyl-3-(4,4,5,5-tetramethyl-1,3,2-dioxaborolan-2-yl) benzoic acid (1 g, 3.8 mmoles) was taken up in CH$_2$Cl$_2$ (200 mL) and was treated with oxalyl chloride (0.44 mL, 5 mmol) and DMF (1 drop). One hour after gas evolution had ceased, the solvents were pumped off in vacuo, and the residue stripped from toluene. This was again taken up in CH$_2$Cl$_2$ (200 mL), and excess dimethyl amine was bubbled into the mixture, which was then sealed off and stirred overnight at room temperature. The solvents were pumped off to give the crude N,N,4-trimethyl-3-(4,4,5,5-tetramethyl-1,3,2-dioxaborolan-2-yl)benzamide, which was used without further purification in the next step.

5-chloro-1-(2,6-difluorophenyl)-7-(methylthio)-3,4-dihydropyrimido[4,5-d]pyrimidin-2(1H)-one (0.102 g, 0.298 mmol), N,N,4-trimethyl-3-(4,4,5,5-tetramethyl-1,3,2-dioxaborolan-2-yl)benzamide from above, (0.129 g, 0.447 mmol), and $K_2CO_3$ (0.123 g, 0.894 mmol), were taken up in dioxane (6 mL) and water (1.2 mL). The mixture was degassed with argon for 30 min and tetrakis(triphenyl-phosphine)palladium(0) (0.026 g, 0.022 mmol) was added. The mixture was then heated under argon at 95° C. for 18 h. The solvents were pumped off, and after aqueous workup, the crude material was flashed on silica gel (15 g), eluted with a EtOAc/$CH_2Cl_2$ gradient to give the title compound as a white amorphous solid. mp 144-147° C. LC-MS m/z 470 (M+H)$^+$, 2.02 min (ret time).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following Claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is Claimed are defined as follows.

What is claimed is:

1. A compound of the formula (II):

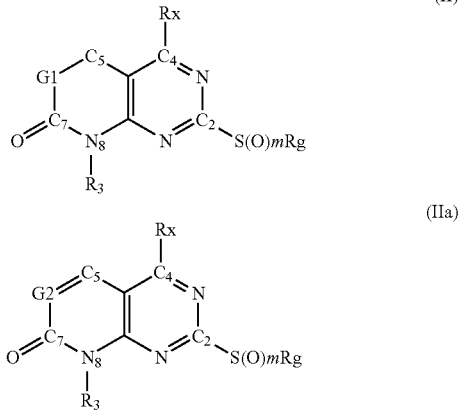

wherein
G1 is NH;
G2 is nitrogen;
Rx is chloro, bromo, iodo, or O—S(O)$_2$CF$_3$;
$R_g$ is a $C_{1-10}$ alkyl;
m is 0, or an integer having a value of 1, or 2;
$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety; and wherein each of these moieties may be optionally substituted.

2. The compound according to claim 1 which is Formula (II).
3. The compound according to claim 1 which is Formula (IIa).
4. The compound according to claim 1 wherein Rg is methyl.
5. The compound according to claim 4 wherein m is 0.
6. The compound according to claim 4 wherein m is 2.
7. The compound according to claim 1 wherein Rx is chloro.
8. The compound according to claim 1 wherein $R_3$ is an optionally substituted aryl.
9. The compound according to claim 8 wherein $R_3$ is optionally substituted, one or more times, independently at each occurrence by halogen, $C_{1-10}$ alkyl, hydroxy, $C_{1-10}$ alkoxy, cyano, nitro, amino, or halosubstituted $C_{1-10}$ alkyl.
10. The compound according to claim 9 wherein $R_3$ is a phenyl substituted one or more times independently by fluorine, chlorine, or methyl.
11. The compound according to claim 8 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2, 6-dimethylphenyl.
12. The compound according to claim 1 which is: 5-chloro-1-(2,6-difluorophenyl)-7-(methylsulfinyl)-3,4-dihydropyrimido[4,5-$d$]pyrimidin-2(1$H$)-one; or 5-chloro-1-(2,6-difluorophenyl)-7-(methylthio)-3,4-dihydropyrimido[4,5-$d$]pyrimidin-2(1$H$)-one.
13. A compound of the formula:

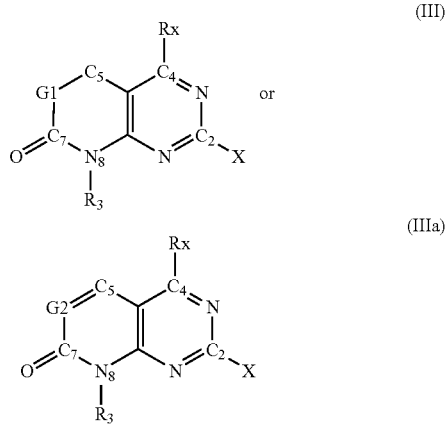

wherein
G1 is NH;
G2 is nitrogen;
Rx is chloro, bromo, iodo, or O—S(O)$_2$CF$_3$;
X is $R_2$, OR$_{2'}$, S(O)$_m$R$_{2'}$, (CH$_2$)$_n$N(R$_{11}$)S(O)$_m$R$_{2'}$, (CH$_2$)$_n$N(R$_{11}$)C(O)R$_{2'}$, (CH$_2$)$_n$NR$_4$R$_{14}$ or (CH$_2$)$_n$N(R$_{2'}$)(R$_{2''}$), or N(R$_{10'}$)—R$_h$—NH—C(=N—CN)NRqRq';
$X_1$ is N(R$_{11}$), O, S(O)$_m$, or CR$_{10}$R$_{20}$;
$R_h$ is selected from an optionally substituted $C_{1-10}$ alkyl, —CH$_2$—C(O)—CH$_2$—, —CH$_2$CH$_2$—O—CH$_2$—CH$_2$—, —CH$_2$—C(O)N(R$_{10'}$)CH$_2$—CH$_2$—, —CH$_2$—N(R$_{10'}$)C(O)CH$_2$—, —CH$_2$—CH(OR$_{10'}$)—CH$_2$, —CH$_2$—C(O)O—CH$_2$—CH$_2$—, or —CH$_2$—CH$_2$—O—C(O)CH$_2$—;
$R_q$ and $R_{q'}$ are independently selected at each occurrence from hydrogen, $C_{1-10}$ alkyl, $C_{3-7}$cycloalkyl, $C_{3-7}$cycloalkylC$_{1-10}$alkyl, $C_{5-7}$ cycloalkenyl, $C_{5-7}$ cycloalkenyl-C$_{1-10}$alkyl, aryl, arylC$_{1-10}$ alkyl, heteroaryl, heteroaryl$C_{1-10}$ alkyl, heterocyclic, or a heterocyclyl$C_{1-10}$ alkyl moiety, wherein all of the moieties, excluding hydrogen, are optionally substituted, or $R_q$ and $R_{q'}$ together with the nitrogen to which they are attached form a 5 to 7 membered optionally substituted ring, which ring may contain an additional heteroatom selected from oxygen, nitrogen or sulfur;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted; or $R_2$ is the moiety $(CR_{10}R_{20})_qX_1(CR_{10}R_{20})_qC(A_1)(A_2)(A_3)$, or $C(A_1)(A_2)(A_3)$;

$R_{2'}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties, excluding hydrogen, may be optionally substituted;

$R_{2''}$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein these moieties, excluding hydrogen, may be optionally substituted; or wherein $R_{2''}$ is the moiety $(CR_{10}R_{20})_tX_1(CR_{10}R_{20})_qC(A_1)(A_2)(A_3)$;

$A_1$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_2$ is an optionally substituted $C_{1-10}$ alkyl, heterocyclic, heterocyclic $C_{1-10}$ alkyl, heteroaryl, heteroaryl $C_{1-10}$ alkyl, aryl, or aryl $C_{1-10}$ alkyl;

$A_3$ is hydrogen or is an optionally substituted $C_{1-10}$ alkyl;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic or a heterocyclyl$C_{1-10}$ alkyl moiety, and wherein each of these moieties may be optionally substituted;

$R_4$ and $R_{14}$ are each independently selected from hydrogen, $C_{1-10}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety, and wherein each of these moieties, excluding hydrogen, may be optionally substituted; or the $R_4$ and $R_{14}$ together with the nitrogen which they are attached form an optionally substituted heterocyclic ring of 4 to 7 members, which ring optionally contains an additional heteroatom selected from oxygen, sulfur or nitrogen;

$R_{10}$ and $R_{20}$ are independently selected from hydrogen or $C_{1-4}$alkyl;

$R_{10'}$ is independently selected at each occurrence from hydrogen or $C_{1-4}$alkyl;

$R_{11}$ is independently selected from hydrogen or $C_{1-4}$alkyl;

n' is independently selected at each occurrence from 0 or an integer having a value of 1 to 10;

m is independently selected at each occurrence from 0 or an integer having a value of 1 or 2;

q is 0 or an integer having a value of 1 to 10;

q' is 0, or an integer having a value of 1 to 6; or t is an integer having a value of 2 to 6.

14. The compound according to claim 13 which is Formula (III).

15. The compound according to claim 13 which is Formula (IIIa).

16. The compound according to claim 13 wherein Rx is chloro.

17. The compound according to claim 13 wherein $R_3$ is an optionally substituted aryl.

18. The compound according to claim 17 wherein $R_3$ is optionally substituted independently, one or more times, independently at each occurrence by halogen, $C_{1-10}$ alkyl, hydroxy, $C_{1-10}$ alkoxy, cyano, nitro, amino, or halosubstituted $C_{1-10}$ alkyl.

19. The compound according to claim 18 wherein $R_3$ is phenyl substituted one or more times independently by fluorine, chlorine or methyl.

20. The compound according to claim 13 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2, 6-dimethylphenyl.

21. The compound according to claim 13 wherein X is $R_2$, and $R_2$ is $(CR_{10}R_{20})_qX_1(CR_{10}R_{20})_qC(A_1)(A_2)(A_3)$, or $C(A_1)(A_2)(A_3)$.

22. The compound according to claim 21 wherein at least one of $A_1$, $A_2$ or $A_3$ is a $C_{1-10}$ alkyl substituted by $(CR_{10}R_{20})_n$ $OR_6$; and wherein n is 0, or an integer having a value of 1 to 10;

m is 0 or an integer having a value of 1 or 2;

$R_6$ is independently selected from hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or a heteroaryl$C_{1-10}$ alkyl moiety, and wherein these moieties, excluding hydrogen may be optionally substituted independently at each occurrence, one or more times, by halogen; hydroxy; hydroxy substituted $C_{1-10}$alkyl; $C_{1-10}$ alkoxy; halosubstituted $C_{1-10}$ alkoxy; S(O)m alkyl; C(O); $NR_{4'}R_{14'}$; $C_{1-10}$ alkyl; $C_{3-7}$cycloalkyl; $C_{3-7}$cycloalkyl $C_{1-10}$ alkyl; halosubstituted $C_{1-10}$ alkyl; an unsubstituted aryl or arylalkyl, or an aryl or arylalkyl substituted one or two times by halogen, hydroxy, hydroxy substituted alkyl, $C_{1-10}$ alkoxy, $S(O)_m$alkyl, amino, mono & di-substituted $C_{1-4}$ alkyl amino, $C_{1-4}$ alkyl, or $CF_3$;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form an optionally substituted 5 to 7 membered ring which optionally contains an additional heteroatom selected from oxygen, sulfur or $NR_{9'}$; and $R_{9'}$ is independently selected at each occurrence from hydrogen, or $C_{1-4}$ alkyl.

23. The compound according to claim 22 wherein $R_2$ is $(CR_{10}R_{20})_{q'}X_1(CR_{10}R_{20})_qC(A_1)(A_2)(A_3)$ and $X_1$ is $N(R_{10'})$, q is 0 or 1, q' is 0, and $R_6$ is hydrogen.

24. The compound according to claim 13 wherein X is $(CH_2)_nNR_4R_{14}$, or $(CH_2)_nN(R_{2'})(R_{2''})$.

25. The compound according to claim 24 wherein X is $(CH_2)_nNR_4R_{14}$, and $R_4$ and $R_{14}$ are independently selected from hydrogen, optionally substituted $C_{1-10}$ alkyl, optionally substituted aryl, optionally substituted aryl-$C_{1-4}$ alkyl, optionally substituted heterocyclic, optionally substituted heterocylic $C_{1-4}$ alkyl, optionally substituted heteroaryl or optionally substituted heteroaryl $C_{1-4}$ alkyl.

26. The compound according to claim 25 wherein the $C_{1-10}$ alkyl maybe substituted one or more times, independently at each occurrence with $NR_{4'}R_{14'}$; halogen, hydroxy, alkoxy, $C(O)NR_{4'}R_{14'}$; or $NR_{4'}C(O)C_{1-10}$ alkyl; and wherein $R_{4'}$ and $R_{14'}$ are independently selected at each occurrence from hydrogen or $C_{1-4}$ alkyl, or $R_{4'}$ and $R_{14'}$ together with the nitrogen to which they are attached form a heterocyclic ring of 5 to 7 members, which ring optionally contains an additional heteroatom selected from $NR_{9'}$; and $R_{9'}$ is independently selected at each occurrence from hydrogen, or $C_{1-4}$ alkyl.

27. The compound according to claim 24 wherein X is $(CH_2)_nN(R_{2'})(R_{2''})$, and $R_{2'}$ is an optionally substituted $C_{1-10}$ alkyl, cycloalkyl, heterocyclic, heterocyclyl $C_{1-10}$ alkyl, or heteroarylalkyl.

28. The compound according to claim 27 wherein the $R_{2'}$ moieties, excluding hydrogen, are optionally substituted 1 to 4 times, independently, at each occurrence, by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl$C_{1-10}$ alkyl, halogen, —C(O), cyano, nitro, aryl, aryl $C_{1-10}$ alkyl, aryl, aryl $C_{1-10}$ alkyl, heterocyclic, heterocyclic $C_{1-10}$ alkyl, heteroaryl, heteroaryl $C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_eR_{e'}$, $(CR_{10}R_{20})_n NR_eR_{e'}C_{1-4}$alkyl$NR_eR_{e'}$, $(CR_{10}R_{20})_nCN$, $(CR_{10}R_{20})_nS(O)_2NR_eR_{e'}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_eR_{e'}$, $(CR_{10}R_{20})_nN(R_{10'})C(Z)R_6$, $(CR_{10}R_{20})_nN(R_{10'})C(=N(R_{10'}))NR_eR_{e'}$, $(CR_{10}R_{20})_nC(=NOR_6)NR_eR_{e'}$, $(CR_{10}R_{20})_nOC(Z)NR_eR_{e'}$, $(CR_{10}R_{20})_nN(R_{10'})C(Z)NR_eR_{e'}$, or $(CR_{10}R_{20})_nN(R_{10'})C(Z)OR_7$; and wherein $R_6$ is independently selected at each occurrence from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties, excluding hydrogen are optionally substituted;

$R_7$ is independently selected at each occurrence from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety, and wherein each of these moieties may be optionally substituted;

$R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety; or $R_e$ and $R_{e'}$ together with the nitrogen which they are attached form an optionally substituted heterocyclic ring of 4 to 7 members, which ring optionally contains an additional heteroatom selected from oxygen, sulfur or nitrogen; and wherein each of these moieties, excluding hydrogen, may be substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; amino, mono & di-substituted $C_{1-4}$ alkyl amino, $S(O)_mR_f$; $C(O)R_j$; $C(O)OR_j$; $(CR_{10}R_{20})_nN(R_{10'})C(Z)OR_7$; $(CR_{10}R_{20})_nN(R_{10'})C(Z)NR_dR_{d'}$; $C(O)NR_4R_{14'}$; $NR_4C(O)C_{1-10}$alkyl; $NR_4C(O)$aryl; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl $C_{1-4}$ alkyl, heterocyclic, heterocyclic$C_{1-4}$ alkyl, heteroaryl, or heteroaryl$C_{1-4}$alkyl, and wherein these aryl, heterocyclic, and heteroaryl containing moieties may be optionally substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$;

$R_d$ and $R_{d'}$ are each independently selected from hydrogen, $C_{1-4}$ alkyl, $C_{3-5}$ cycloalkyl, $C_{3-5}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$; and wherein the $R_d$ and $R_{d'}$ moieties which are $C_{1-4}$ alkyl, $C_{3-5}$cycloalkyl, $C_{3-5}$cycloalkyl$C_{1-4}$ alkyl, and the $R_4$ and $R_{14}$ cyclized ring are optionally substituted, 1 to 4 times, independently by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; $S(O)mR_f$; $C(O)R_j$; $C(O)OR_j$; $C(O)NR_4R_{14'}$, $NR_4C(O)C_{1-4}$alkyl; $S(O)_2NR_4R_{14'}C_{1-4}$ alkyl; $NR_4R_{14'}S(O)_2C_{1-4}$ alkyl; or $NR_4R_{14'}$;

$R_f$ is independently selected at each occurrence from $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties may all be optionally substituted;

$R_{f'}$is independently selected at each occurrence from hydrogen, $C_{1-10}$alkyl, aryl, aryl $C_{1-10}$alkyl, heteroaryl, heteroaryl $C_{1-10}$alkyl, heterocyclic, heterocyclic $C_{1-10}$alkyl, or $NR_4R_{14'}$and wherein these moieties may all be optionally substituted;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form a 5 to 7 membered ring which optionally contains an additional heteroatom selected from oxygen, sulfur or $NR_{9'}$;

$R_{9'}$is independently selected at each occurrence from hydrogen, or $C_{1-4}$ alkyl;

$R_j$ is independently selected at each occurrence from hydrogen, $C_{1-4}$alkyl, aryl, aryl $C_{1-4}$ alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted; and n is independently selected at each occurrence from 0 or an integer having a value of 1 to 10.

29. The compound according to claim 28 wherein $R_{2'}$ is a heterocyclic or a heterocyclic alkyl substituted one or more times, independently by $C_{1-10}$ alkyl, aryl, arylalkyl, $(CR_{10}R_{20})_nNR_eR_{e'}$, or $(CR_{10}R_{20})_nN(R_{10'})C(Z)OR_7$.

30. The compound according to claim 13 wherein the $(CH_2)_nN(R_{2'})(R_{2''})$ moiety is 1-(phenylmethyl)-4-piperidinamine, 2-[4-(phenylmethyl)-1-piperazinyl]ethylamine, 2-(1-piperidinyl)ethylamine, 2-(1-methyl-2-pyrrolidinyl) ethylamine, 1-[(phenylmethyl)-3-pyrrolidinyl]amine, 3-[(1-pyrrolidinyl)propyl]amine, 3-[(hexahydro-1H-azepin-1-yl) propyl]amine, (1-methyl-4-piperidinyl)amine, 3-[(4-morpholinyl)propyl]amine, 3-[(2-oxo-1-pyrrolidinyl) propyl]amine, 2-[(4-morpholinyl)ethyl]amine, 2-[(1-pyrrolidinyl)ethyl]amine, or [(1-ethyl-2-pyrrolidinyl) methyl]amine.

31. The compound according to claim 13 wherein $R_{2'}$ is a $C_{1-10}$ alkyl substituted by $(CR_{10}R_{20})_nNR_eR_{e'}$ or $(CR_{10}R_{20})_n NR_eR_{e'}C_{1-4}$alkyl$NR_eR_{e'}$and wherein $R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety; or $R_e$ and $R_{e'}$together with the nitrogen which they are attached form an optionally substituted heterocyclic ring of 4 to 7 members, which ring optionally contains an additional heteroatom selected from oxygen, sulfur or nitrogen; and wherein each of these moieties, excluding hydrogen, may be substituted 1 to 4 times, independently at each occurrence by halogen; hydroxy; hydroxy substituted $C_{1-10}$alkyl; $C_{1-10}$ alkoxy; halosubstituted $C_{1-10}$ alkoxy; amino, mono & di-substituted $C_{1-4}$ alkyl amino, $S(O)mR_f$; $C(O)R_j$; $C(O)OR_j$; $(CR_{10}R_{20})_nN$ $(R_{10'})C(Z)OR_7$; $(CR_{10}R_{20})_nN(R_{10'})C(Z)NR_dR_{d'}$; $C(O)NR_{4'}R_{14'}$; $NR_{4'}C(O)C_{1-10}$alkyl; $NR_{4'}C(O)$aryl; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl $C_{1-4}$ alkyl, heterocyclic, heterocyclic $C_{1-4}$ alkyl, heteroaryl, or heteroaryl $C_{1-4}$alkyl, and wherein these aryl, heterocyclic, and heteroaryl containing moieties may be optionally substituted one to two times independently at each occurrence by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$;

$R_d$ and $R_{d'}$ are each independently selected from hydrogen, $C_{1-4}$ alkyl, $C_{3-5}$ cycloalkyl, $C_{3-5}$ cycloalkyl $C_{1-4}$ alkyl or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$; and wherein the $R_d$ and $R_{d'}$ moieties which are $C_{1-4}$ alkyl, $C_{3-5}$cycloalkyl, $C_{3-5}$cycloalkyl $C_{1-4}$ alkyl, and the $R_4$ and $R_{14}$ cyclized ring are optionally substituted, 1 to 4 times, independently by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; $S(O)mRf$; $C(O)R_j$; $C(O)O\ R_j$; $C(O)NR_{4'}R_{14'}$, $NR_{4'}C(O)C_{1-4}$ alkyl; $S(O)_2NR_{4'}R_{14'}C_{1-4}$ alkyl; $NR_{4'}R_{14'}S(O)_2C_{1-4}$ alkyl; or $NR_{4'}R_{14'}$;

$R_f$ is independently selected at each occurrence from $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties may all be optionally substituted;

$R_{f'}$ is independently selected at each occurrence from hydrogen, $C_{1-10}$alkyl, aryl, aryl $C_{1-10}$alkyl, heteroaryl, heteroaryl $C_{1-10}$alkyl, heterocyclic, heterocyclic $C_{1-10}$alkyl, or $NR_{4'}R_{14'}$ and wherein these moieties may all be optionally substituted;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form a 5 to 7 membered ring which optionally contains an additional heteroatom selected from oxygen, sulfur or $NR_{9'}$;

$R_{9'}$ is independently selected at each occurrence from hydrogen, or $C_{1-4}$ alkyl;

$R_j$ is independently selected at each occurrence from hydrogen, $C_{1-4}$ alkyl, aryl, aryl $C_{1-4}$alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted; and n is independently selected at each occurrence from 0 or an integer having a value of 1 to 10.

32. The compound according to claim 31 wherein $R_e$ and $R_{e'}$ are independently selected from methyl, ethyl, isopropyl, n-butyl, or t-butyl.

33. The compound according to claim 13 wherein $(CH_2)_{n'}N(R_{2'})(R_{2''})$ is 3-(dimethylamino)propyl(methyl)amine, 3-(diethylamino)propylamine, propylamine, (2,2-dimethylpropyl)amine, (2-hydroxypropyl)amino, 2-(dimethylamino) ethylamine, 2-(dimethylamino)ethyl(methyl)amine, 3-(dimethylamino)propylamine, 2-(dimethylamino)ethyl(methyl) amine, 3-(diethylamino)propylamine, 2-(methylamino) ethylamine, [(1-methylethyl)amino]ethylamine, 3-(diethylamino)propylamine, 3-(dibutylamino)propylamine, 3-[(1-methylethyl)amino]propylamine, 3-(1,1-dimethylethyl)aminopropylamine, 3-(dimethylamino)-2,2-dimethylpropylamine, 4-(diethylamino)-1-methylbutylamine, or 3-[[3-(dimethylamino)propyl]-(methyl)amino]propyl(methyl)amine.

34. The compound according to claim 13 wherein $R_3$ is an aryl optionally substituted one or more times independently at each occurrence with halogen, nitro, $C_{1-10}$ alkyl, halosubstituted $C_{1-10}$ alkyl, $C_{2-10}$ alkenyl, $C_{2-10}$alkynyl, $C_{3-7}$cycloalkyl, $C_{3-7}$cycloalkyl $C_{1-10}$alkyl, $C_{5-7}$cycloalkenyl, $C_{5-7}$cycloalkenyl $C_{1-10}$ alkyl, $(CR_{10}R_{20})_nOR_6$, $(CR_{10}R_{20})_n$SH, $(CR_{10}R_{20})_nS(O)_mR_7$, $(CR_{10}R_{20})_nN(R_{10'})S(O)_2R_7$, $(CR_{10}R_{20})_nNR_{16}R_{26}$, $(CR_{10}R_{20})_nCN$, $(CR_{10}R_{20})_nS(O)_2NR_{16}R_{26}$, $(CR_{10}R20)_nC(Z)R_6$, $(CR_{10}R_{20})_nOC(Z)R_6$, $(CR_{10}R_{20})_nC(Z)OR_6$, $(CR_{10}R_{20})_nC(Z)NR_{16}R_{26}$, $(CR_{10}R_{20})_nN(R_{10'})C(Z)R_6$, $(CR_{10}R_{20})_nN(R_{10'})C(=N(R_{10'}))NR_{16}R_{26}$, $(CR_{10}R_{20})_nOC(Z)NR_{16}R_{26}$, $(CR_{10}R_{20})_nN(R_{10'})C(Z)NR_{16}R_{26}$, or $(CR_{10}R_{20})_nN(R_{10'})C(Z)OR_7$; and wherein $R_6$ is independently selected from hydrogen, $C_{1-10}$ alkyl, $C_{3-7}$ cycloalkyl, heterocyclyl, heterocyclyl $C_{1-10}$alkyl, aryl, aryl $C_{1-10}$ alkyl, heteroaryl or a heteroaryl $C_{1-10}$ alkyl moiety, and wherein these moieties, excluding hydrogen may be optionally substituted;

$R_7$ is $C_{1-6}$alkyl, aryl, aryl $C_{1-6}$alkyl, heterocyclic, heterocyclyl $C_{1-6}$ alkyl, heteroaryl, or heteroaryl $C_{1-6}$alkyl; and wherein each of these moieties may be optionally substituted;

$R_{10'}$ is independently selected at each occurrence from hydrogen or $C_{1-4}$ alkyl;

$R_{10}$ and $R_{20}$ are independently selected at each occurrence from hydrogen or $C_{1-4}$ alkyl;

$R_{16}$ and $R_{26}$ are each independently selected from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_{9'}$;

$R_{9'}$ is independently selected at each occurrence from hydrogen, or $C_{1-4}$ alkyl;

n is independently selected at each occurrence from 0 or an integer having a value of 1 to 10;

m is independently selected from 0 or an integer having a value of 1 or 2;

Z is independently at each occurrence selected from oxygen or sulfur.

35. The compound according to claim 33 wherein $R_3$ is an optionally substituted phenyl.

36. The compound according to claim 35 wherein the optional substituents on the phenyl ring are independently selected at each occurrence from halogen, $C_{1-10}$alkyl, $(CR_{10}R_{20})_nOR_6$, cyano, nitro, $(CR_{10}R_{20})_nNR_{16}R_{26}$, or halosubstituted $C_{1-10}$ alkyl.

37. The compound according claim 24 wherein the phenyl is substituted one or more times by halogen, hydroxy, alkoxy, amino or $CF_3$.

38. The compound according to claim 36 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2,6-dimethylphenyl.

39. The compound according to claim 13 which is:
7(1,4'-bipiperidin-1'-yl)-5-chloro-1-(2,6-difluorophenyl)-3,4-dihydropyrimido[4,5-d]pyrimidin-2(1H)-one; or
5-chloro-1-(2,6-difluorophenyl)-7-[4-(1-pyrrolidinyl)-1-piperidinyl]-3,4-dihydropyrimido]4,5-d]pyrimidin-2(1H)-one 40. The compound according to claim 13 which is:
5-chloro-7-{[3-(diethylamino)propyl]amino}-1-(2,6-difluorophenyl)-3,4-dihydropyrimido[4,5-d]pyrimidin-2(1H)-one;

5-chloro-1-(2,6-difluorophenyl)-7-{[2-(dimethylamino)ethyl]amino}-3,4-dihydropyrimido[4,5-d]pyrimidin-2(1H)-one.

41. The compound according to claim 2 wherein Rg is methyl.
42. The compound according to claim 3 wherein Rg is methyl.
43. The compound according to claim 41 wherein m is 0.
44. The compound according to claim 42 wherein m is 0.
45. The compound according to claim 41 wherein m is 2.
46. The compound according to claim 42 wherein m is 2.
47. The compound according claim 43 wherein Rx is chloro.
48. The compound according to claim 44 wherein Rx is chloro.
49. The compound according to claim 47 wherein $R_3$ is phenyl or a phenyl substituted one or more times independently by fluorine, chlorine, or methyl.
50. The compound according to claim 49 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2, 6-dimethylphenyl.
51. The compound according to claim 48 wherein $R_3$ is phenyl or a phenyl substituted one or more times independently by fluorine, chlorine, or methyl.
52. The compound according to claim 51 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2, 6-dimethylphenyl.
53. The compound according to claim 14 wherein Rx is chloro.
54. The compound according to claim 15 wherein Rx is chloro.
55. The compound according to claim 54 wherein $R_3$ is an optionally substituted aryl.
56. The compound according to claim 55 wherein $R_3$ is optionally substituted independently, one or more times, independently at each occurrence by halogen, $C_{1-10}$ alkyl, hydroxy, $C_{1-10}$ alkoxy, cyano, nitro, amino, or halosubstituted $C_{1-10}$ alkyl.
57. The compound according to claim 54 wherein $R_3$ is phenyl, or phenyl substituted one or more times independently by fluorine, chlorine or methyl.
58. The compound according to claim 54 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2, 6-dimethylphenyl.
59. The compound according to claim 33 wherein Rx is chioro.
60. The compound according to claim 59 which is Formula (III).
61. The compound according to claim 59 wherein $R_3$ is a phenyl substituted one or more times independently by fluorine, chlorine or methyl.
62. The compound according to claim 61 wherein X is 2-(dimethylamino)ethylamino.
63. The compound according to claim 13 wherein X is $R_2$.
64. The compound according to claim 63 wherein $R_2$ is an optionally substituted heterocyclic selected from the group consisting of tetrahydropyrrole, tetrahydropyran, tetrahydrofuran, tetrahydrothiophene, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino.
65. The compound according to claim 64 wherein $R_2$ is an optionally substituted one or mores times independently by an optionally substituted heterocyclic, heterocyclic alkyl, aryl, arylalkyl, alkyl, $(CR_{10}R_{20})_nNR_eR_{e'}$, or $(CR_{10}R_{20})_nN(R_{10'})C(Z)OR_7$ and wherein $R_e$ are $R_{e'}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, aryl-$C_{1-4}$ alkyl, heterocyclic, heterocyclic $C_{1-4}$ alkyl, heteroaryl or a heteroaryl $C_{1-4}$ alkyl moiety; or $R_e$ and $R_{e'}$ together with the nitrogen which they are attached form an optionally substituted heterocyclic ring of 4 to 7 members, which ring optionally contains an additional heteroatom selected from oxygen, sulfur or nitrogen; and wherein each of these moieties, excluding hydrogen, may be substituted 1 to 4 times, independently at each occurrence by halogen hydroxy; hydroxy substituted $C_{1-10}$alkyl; $C_{1-10}$ alkoxy; halosubstituted $C_{1-10}$ alkoxy; amino, mono & di-substituted $C_{1-4}$ alkyl amino, $S(O)mR_f$; $C(O)R_j$; $C(O)OR_j$; $(CR_{10}R_{20})_nN(R_{10'})C(Z)OR_7$; $(CR_{10}R_{20})_nN(R_{10'})C(Z)NR_dR_{d'}$; $C(O)NR_4R_{14}$; $NR_4C(O)C_{1-10}$alkyl; $NR_4C(O)$aryl; cyano; nitro; $C_{1-0\ alkyl}$; $C_{3-7}$cycloalkyl; $C_{3-7}$cycloalkyl $C_{1-10}$alkyl halosubstituted $C_{1-10}$ alkyl; aryl, aryl $C_{1-4}$alkyl, heterocyclic, heterocyclic$C_{1-4}$ alkyl, heteroaryl, or heteroaryl$C_{1-4}$alkyl, and wherein these aryl, heterocyclic, and heteroaryl containing moieties may be optionally substituted one to two times independently at each occurrence by halogen, $C_{1-4}$alkyl, hydroxy, hydroxy substituted $C_{1-4}$ alkyl, $C_{1-0}$ alkoxy, $S(O)_m$alkyl, amino, mono & di-substituted $C_{1-4}$ alkyl amino, $C_{1-4}$ alkyl, or $CF_3$;

$R_d$ and $R_{d'}$ are each independently selected from hydrogen, $C_{1-4}$ alkyl, $C_{3-5}$ cycloalkyl, $C_{3-5}$ cycloalkyl$C_{1-4}$alkyl or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_{9'}$; and wherein the $R_d$ and $R_{d'}$ moieties which are $C_{1-4}$ alkyl, $C_{3-5}$cycloalkyl, $C_{3-5}$cycloalkyl$C_{1-4}$ alkyl, and the $R_4$ and $R_{14}$ cyclized ring are optionally substituted, 1 to 4 times, independently by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; $S(O)mRf$; $C(O)R_j$; $C(O)O R_j$; $C(O)NR_4R_{14}$; $NR_4C(O)C_{1-4}$ alkyl; $S(O)_2NR_4R_{14}C_{1-4}$ alkyl; $NR_4R_{14}S(O)_2C_{1-4}$ alkyl; or $NR_4R_{14}$;

$R_f$ is independently selected at each occurrence from $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties may all be optionally substituted;

$R_j$ is independently selected at each occurrence from hydrogen, $C_{1-10}$alkyl, aryl, aryl $C_{1-10}$alkyl, heteroaryl, heteroaryl $C_{1-10}$alkyl, heterocyclic, heterocyclic $C_{1-10}$alkyl, or $NR_4R_{14}$ and wherein these moieties may all be optionally substituted;

$R_{4'}$ and $R_{14'}$ are each independently selected at each occurrence from hydrogen or $C_{1-4}$alkyl, or $R_{4'}$ and $R_{14'}$ can cyclize together with the nitrogen to which they are attached to form a 5 to 7 membered ring which optionally contains an additional heteroatom selected from oxygen, sulfur or $NR_{9'}$;

$R_{9'}$ is independently selected at each occurrence from hydrogen, or $C_{1-4}$ alkyl;

$R_j$ is independently selected at each occurrence from hydrogen, $C_{1-4}$alkyl, aryl, aryl $C_{1-4}$alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted; and n is independently selected at each occurrence from 0 or an integer having a value of 1 to 10.

66. The compound according to claim 65 wherein the optionally substituted heterocyclic is selected from an optionally substituted morpholino, piperidine, or pyrrolidinyl.

67. The compound according to claim 64 wherein $R_2$ is an optionally substituted piperidinyl or piperazinyl ring.

68. The compound according to claim 63 wherein $R_2$ is a 4-amino-1-piperidinyl, 1,1-dimethylethyl)oxy]-carbonyl}amino)-1-piperidinyl, 4-methyl-1-piperazinyl, 4-ethyl-1-piperazinyl, 4-propyl-1-piperazinyl, 4-butyl-1-piperazinyl, 4-(methylamino)-1-piperidinyl, 1,1-dimethylethyl-4-piperidinyl}methylcarbamate, 4-phenyl-1-piperazinyl, 1,4'-bipiperidin-1'-yl, 4-(1-pyrrolidinyl)-1-piperidinyl, 4-methyl-1,4'-bipiperidin-1'-yl, 4-(4-morpholinyl)-1-piperidinyl, 4-(diphenylmethyl)-1-piperazinyl, or 4-methyl-hexahydro-1H-1,4-diazepin-1-yl.

69. The compound according to claim 68 wherein $R_2$ is 4-methyl-1,4'- bipiperidin-1'-yl, or (1-pyrrolidinyl)-1-piperidinyl.

* * * * *